(12) United States Patent
Gao et al.

(10) Patent No.: US 7,838,277 B2
(45) Date of Patent: Nov. 23, 2010

(54) METHOD FOR RAPID SCREENING OF BACTERIAL TRANSFORMANTS AND NOVEL SIMIAN ADENOVIRUS PROTEINS

(75) Inventors: Guangping Gao, Rosemont, PA (US); James M Wilson, Gladwyne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/011,377

(22) Filed: Jan. 25, 2008

(65) Prior Publication Data

US 2008/0219954 A1 Sep. 11, 2008

Related U.S. Application Data

(62) Division of application No. 10/477,527, filed as application No. PCT/US02/19735 on Jun. 20, 2002, now Pat. No. 7,344,872.

(60) Provisional application No. 60/385,632, filed on Jun. 4, 2002, provisional application No. 60/300,501, filed on Jun. 22, 2001.

(51) Int. Cl.
*C12N 7/01* (2006.01)
*A61K 39/235* (2006.01)

(52) U.S. Cl. ............... 435/235.1; 424/199.1; 424/93.2; 435/320.1

(58) Field of Classification Search ............. None
See application file for complete search history.

(56) References Cited

U.S. PATENT DOCUMENTS

| | | | |
|---|---|---|---|
| 5,770,442 | A | 6/1998 | Wickham et al. |
| 5,922,315 | A | 7/1999 | Roy |
| 6,083,716 | A | 7/2000 | Wilson et al. |
| 7,291,498 | B2 | 11/2007 | Roy |
| 7,491,508 | B2 | 2/2009 | Roy |
| 2003/0092161 | A1 | 5/2003 | Gao et al. |
| 2004/0171807 | A1 | 9/2004 | Gao et al. |
| 2009/0074810 | A1 | 3/2009 | Roy |

FOREIGN PATENT DOCUMENTS

| | | |
|---|---|---|
| WO | WO 98/10087 A1 | 3/1998 |
| WO | WO 98/32842 A1 | 7/1998 |
| WO | WO 99/41359 A1 | 8/1999 |
| WO | WO 0003029 A2 | 1/2000 |
| WO | WO 03/046124 A2 | 6/2003 |
| WO | WO 2005/026337 | 3/2005 |

OTHER PUBLICATIONS

Stevenson et al (Journal of Virology 71:4782-4790, 1997).*
Farina, S.F., et al, Simian Adenovirus 25, complete genome, Sequence Revision History, uploaded online Nov. 27, 2001, NCBI, www.ncbi.nlm.nih.gov/entrez/viewer.fcgi, NCBI:2777951 retrieved from internet Mar. 3, 2008, www.ncbi.nlu.nih.gov/entrez/sutils/girevhist.cgi/val.
Russell, Update on Adenovirus and its Vectors, Journal of Virology, 81, pp. 2573-2604, (Nov. 2000).
Farina et al, Replication-Defective Vector Based on a Chimpanzee Adenovirus, Journal of Virology, vol. 75, No. 23, pp. 11603-11613, (Dec. 2001).
Farina et al, Simian Adenovirus 25 PIII, Database EMBL, Database accession No. Q8UY83, (Mar. 1, 2002), XP002313001.
Farina et al, Simian Adenovirus 25 PII, Database EMBL, Database Accession No. Q8UY79, (Mar. 1, 2002), XP002313002.
Farina et al, Simian Adenovirus 25 PIV (fiber), Database EMBL, Database Accession No. Q8UY68, (Mar. 1 2002), XP002313003.
Farina et al, Simian Adenovirus 25 E2A, Database EMBL, Database Accession No. Q8UY78, (Mar. 1, 2002), XP002313004.
Cuzange et al, The Penton Base of Human Adenovirus Type 3 has the RGD Motif, Gene, vol. 146, No. 2, pp. 257-259, (Apr. 1994).
Gruber et al, Fiber Gene and Genomic Origin of Human Adenovirus Type 4, Virology, vol. 196, No. 2, pp. 603-611, (Oct. 1993).
Pring-Akerblom et al, Hexon Sequence of Adenovirus type 7 and Comparison with Other Serotypes of Subgenus B, Research in Virology, vol. 146, No. 6, pp. 383-388, (Aug. 1995).
Roy, Characterization of a Family of Chimpanzee Adenoviruses and Development of Molecular Clones for Gene Transfer Vectors, Human Gene Therapy, 15:519-530 (May 2004).
Gall et al, Construction and Characterization of Hexon-Chimeric Adenoviruses: Specification of Adenovirus Serotype, Journal of Virology, vol. 72, pp. 10260-10264, XP002327347, (Dec. 1998).
Gall et al, Adenovirus Type 5 and 7 Capsid Chimera: Fiber Replacement Alters Receptor Tropism Without Affecting Primary Immune Neutralization Epitopes, Journal of Virology, vol. 70, pp. 2116-2123, XP000653519, (Apr. 1996).
Krasnykh et al, Generation of Recombinant Adenovirus Vectors with Modified Fibers for altering Viral Tropism, Journal of Virology, vol. 70, No. 10, pp. 6839-6846, (Oct. 1996).
Wickham et al, Increased in vitro and in Vivo Gene Transfer by Adenovirus Vectors Containing Chimeric Fiber Proteins, Journal of Virology, vol. 71, No. 11, (Nov. 1997).
STIC Sequence/fragment search results 14, 15.
Printout of Wilson et al. SEQ ID No. 2 from SCORE, pp. 10-11.
Printout of Translated Amino Acid SEQ ID No. 2 from http://ca.expasy.org.
Applicant's Response dated Oct. 15, 2007 in EPO Patent Application No. 02756264.4.
Communication dated Mar. 25, 2008 in EPO Patent Application No. 02756264.4.
Applicant's Response dated Oct. 6, 2008 in EPO Patent Application No. 02756264.4.
Vigne et al, RGD inclusion in the hexon monomer provides adenovirus type-5 based vectors with a fiber knob-independent pathway for infection, Journal of Virology, 73(6):5156-5161 (Jun. 1999).
Rux et al, Structural and phylogenetic analysis of adenovirus hexons by use of high-resolution x-ray crystallographic, molecular modeling, and sequence-based methods, Journal of Virology, 77(17):9553-9566 (Sep. 2003).

(Continued)

*Primary Examiner*—Mary E Mosher
(74) *Attorney, Agent, or Firm*—Howson & Howson LLP

(57) ABSTRACT

Chimpanzee serotype C68 proteins, peptides, and polypeptide are provided. Also provided are novel adenoviruses derived from these proteins, as well as compositions containing these proteins and methods of using same for immunization and therapy. Further, a rapid method for screening recombinant transformants using a visually detectable method is described.

5 Claims, 4 Drawing Sheets

OTHER PUBLICATIONS

Crawford-Miksza et al, Analysis of 15 adenovirus hexon proteins reveals the location and structure of seven hypervariable regions containing serotype-specific residues, Journal of Virology, 70(3):1836-1844 (Mar. 1996).

Worgall et al, Protection against *P. aeruginosa* with an adenovirus vector containing an OprF epitope in the capsid, Journal of Clinical Investigation, 115(5):1281-1289 (May 2005).

* cited by examiner

| | | |
|---|---|---|
| Pan-9 fiber knob | (1) | TLWTTPDPSPNCQILAENDAKLTLCLTKCGSQILATVSVLVVGSG-NLNP |
| Ad 2 fiber knob | (1) | TLWTTPDPSPNCRIHSDNDCKFTLVLTKCGSQVLATVAALAVSG--DLSS |
| Ad 5 fiber knob | (1) | TLWTTPAPSPNCRLNAEKDAKLTLVLTKCGSQILATVSVLAVKG--SLAP |
| | | |
| Pan-9 fiber knob | (50) | ITGTVSSAQVFLRFDANGVLLTEHSTLKKYWGYRQGDSIDGTPYTNAVGF |
| Ad 2 fiber knob | (49) | MTGTVASVSIFLRFDQNGVLMENSSLKKHYWNFRNGNSTNANPYTNAVGF |
| Ad 5 fiber knob | (49) | ISGTVQSAHLIIRFDENGVLLNNSFLDPEYWNFRNGDLTEGTAYTNAVGF |
| | | |
| Pan-9 fiber knob | (100) | MPNLKAYPKSQSSTTKNNIVGQVYMNGDVSKPMLLTITLNGTDDS------ |
| Ad 2 fiber knob | (99) | MPNLLAYPKTQSQTAKNNIVSQVYLHGDKTKPMILTITLNGTSESTETSE |
| Ad 5 fiber knob | (99) | MPNLSAYPKSHGKTAKSNIVSQVYLNGDKTKPVTLTITLNGTQET-GDTT |
| | | |
| Pan-9 fiber knob | (145) | NSTYSMSFSYTWT-NGSYVGATFGANSYTFSYIAQE |
| Ad 2 fiber knob | (149) | VSTYSMSFTWSWE-SGKYTTETFATNSYTFSYIAQE |
| Ad 5 fiber knob | (148) | PSAYSMSFSWDWS-GHNYINEIFATSSYTFSYIAQE |

```
Hu5   APKGAPNPCEWDEAATALEINLEEEDDDNEDEVDEQAEQQKTHVFGQAPYSGINITKEGIQIGVEGQT--
Pan-9 APKGAPNTCQWTYKADG--------------------ETATEKTYTYGNAPVQGINITKDGIQLGTDTDD--

Hu5   --PKYADKTFQPEPQIGESQWYETEIN--HAAGRVLKKTTPMKPCYGSYAKPTNENGGQGILVKQQN---G
Pan-9 -QPIYADKTYQPEPQVGDAEWHDITGTDEKYGGRALKPDTKMKPCYGSFAKPTNKEGGQANVKTGTG---T

Hu5   KLESQVEMQFFSTTEATAGNGDNLTPKVVLYSEDVDIETPDTHISYMPTIKEGNSRELMGQQSMPNRPNY
Pan-9 TKEYDIDMAFFDNRSAAAAG----LAPEIVLYTENVDLETPDTHIVYKAGTDDSSSSINLGQQAMPNRPNY

Hu5   IAFRDNFIGLMYYNSTGNMGVLAGQASQLNAVVDLQDRNTELSYQLLLDSIGDRTRYFSMWNQAVDSYDP
Pan-9 IGFRDNFIGLMYYNSTGNMGVLAGQASQLNAVVDLQDRNTELSYQLLLDSLGDRTRYFSMWNQAVDSYDP

Hu5   DVRIIENHGTEDELPNYCFPLGGVINTETLTKVKPKTG----QENGWEKDATEFSDKNEIRVGNNFAMEI
Pan-9 DVRIIENHGVEDELPNYCFPLDAVGRTDTYQGIKAN----GTDQTTWTKDDSVN-DANEIGKGNPFAMEI
```

METHOD FOR RAPID SCREENING OF BACTERIAL TRANSFORMANTS AND NOVEL SIMIAN ADENOVIRUS PROTEINS

CROSS-REFERENCE TO RELATED APPLICATIONS

This application a divisional of U.S. patent application Ser. No. 10/477,527, filed Nov. 21, 2003, which is a national phase of PCT/US02/19735, filed Jun. 20, 2002, pursuant to 35 USC 371, which claims the benefit of the priority of U.S. Patent Application No. 60/385,632, filed Jun. 4, 2002 and US Patent Application No. 60/300,501, filed Jun. 22, 2001, pursuant to 35 USC 119(e).

BACKGROUND OF THE INVENTION

Recombinant adenoviruses have been described for gene therapy and vaccine uses.

Adenoviruses have a characteristic morphology with an icosahedral capsid consisting of three major proteins, hexon (II), penton base (III) and a knobbed fibre (IV), along with a number of other minor proteins, VI, VIII, IX, IIIa and IVa2 [W. C. Russell, *J. Gen Virol.*, 81:2573-2604 (November 2000)]. The virus genome is a linear, double-stranded DNA with a terminal protein attached covalently to the 5' termini, which have inverted terminal repeats (ITRs). The virus DNA is intimately associated with the highly basic protein VII and a small peptide termed mu. Another protein, V, is packaged with this DNA-protein complex and provides a structural link to the capsid via protein VI. The virus also contains a virus-encoded protease, which is necessary for processing of some of the structural proteins to produce mature Infectious virus.

There continues to be a need for recombinant viral vectors and improved methods for making these vectors.

SUMMARY OF THE INVENTION

In one aspect, the invention provides a method for rapid screening of bacterial transformants. The method involves engineering a recombinant shuttle vector comprising a nucleic acid cassette containing a transgene and a nucleic acid sequence encoding prokaryotic green fluorescent protein (GFP) operably linked to regulatory sequences which permit its expression in a host cell. Thereafter, host cells are transfected with the shuttle vector and screened for expression of GFP. The absence of green color (i.e., white) is indicative of a cell carrying the recombinant virus. Expression of GFP is readily detected by the green color when activated by fluorescent light, and indicates the presence of parent virus (i.e., absence of recombinant).

In another aspect, the invention provides capsid proteins of C68, isolated from other C68 proteins, and characterized by the amino acids provided herein.

In still another embodiment, the invention provides adenoviral vectors and non-viral targeting proteins derived from the C68 capsid proteins, termed herein C68-derived constructs.

Yet other advantages of the present invention will be readily apparent from the following detailed description of the invention.

BRIEF DESCRIPTION OF THE DRAWINGS

In FIG. 1A the genome of the C68 chimpanzee adenovirus is schematically represented by the box at the top. The inverted terminal repeats are shaded black and the early regions are shaded gray. The arrowheads above the box indicate the direction of expression of the early genes. The line below the box represents the division of the genome into 100 map units. The arrows below the line represent the five late gene regions and the proteins encoded in each region. The numbers below the box or arrows indicate the start (promoter or initiation codon) and end (canonical PolyA signal) for each region. * represents the E2A late promoter. FIG. 1B illustrates the PstI clones; FIG. 1C illustrates the BamHI clones. FIG. 1D illustrates the HindIII clones. For parts 1B-1D, the unshaded regions indicate that a fragment was cloned into a plasmid vector, while the shaded regions indicate that the restriction fragment was not cloned. For each section the fragment name, alphabetical with A being the largest fragment, and the fragment size are listed above the box and the fragment end points are listed below the box.

Figure 2:
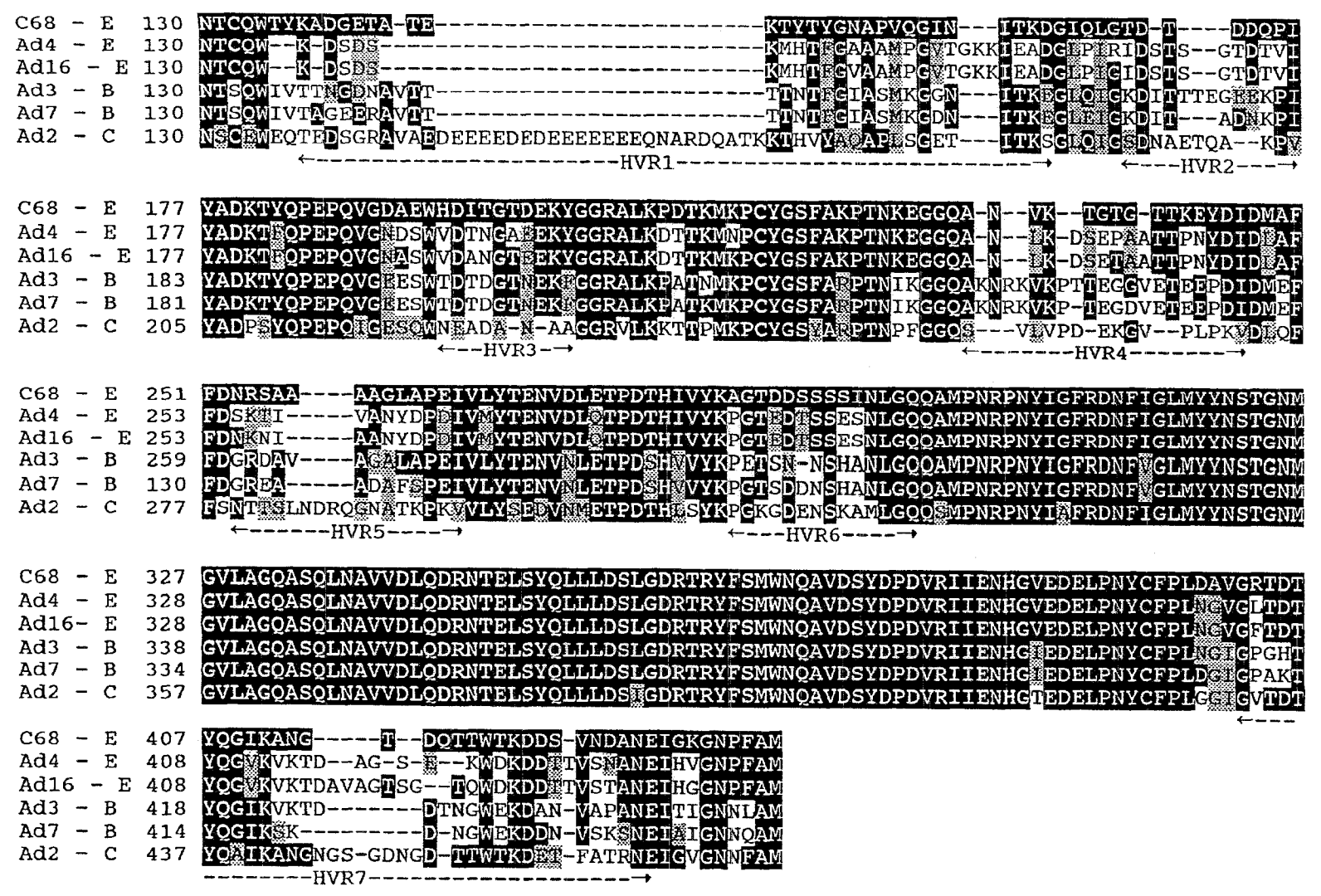

FIG. 2 provides a sequence alignment of the C68 hexon protein [aa 131 to 441 of SEQ ID NO:16] with Ad4 [SEQ ID NO:34], Ad16 [SEQ ID NO:35], Ad3 [SEQ ID NO:36], Ad7 [SEQ ID NO:37], and Ad2 [SEQ ID NO:38]. The deduced amino acid sequences of highly similar human adenovirus hexons were compared with the C68 chimpanzee adenovirus using CLUSTAL X. Serotypes and subgroups are indicated on the left margin, followed by the residue number. The numbering refers to the amino acid position with respect to the start of translation. Amino acids are shaded with respect to C68 to highlight sequence similarities (gray) and identities (black). The seven hypervariable regions within loop domains DE1 and FG1 are labeled along the bottom and correspond to the following Ad2 sequences in the alignment: HVR1, 137-188; HVR2, 194-204; HVR3, 222-229; HVR4, 258-271; HVR5, 278-294; HVR6, 316-327; and HVR7, 433-465 of SEQ ID NO:16. The GenBank accession numbers for the sequences shown are as follow: AAD03657 (Ad4), S37216 (Ad16), S39298 (Ad3), AAD03663 (Ad7), and NP040525 (Ad2).

FIG. 3 provides an alignment of the amino acid sequences of the fiber knob domains of chimpanzee C68 (Pan-9) [amino acids 247 to 425 of SEQ ID NO: 27] and the human adenovirus serotypes 2 [SEQ ID NO: 39] and 5 [SEQ ID NO:40].

FIG. 4 provides an alignment of the amino acid sequences of the L1 and a portion of the L2 loops of the capsid hexon on the human adenovirus serotype 5 [SEQ ID NO:41] and chimpanzee C68 (Pan-9) [amino acids 125 to 443 of SEQ ID NO:16] adenovirus sequences. The intervening conserved region is part of the pedestal domain conserved between adenovirus serotypes.

DETAILED DESCRIPTION OF THE INVENTION

Figure 1:
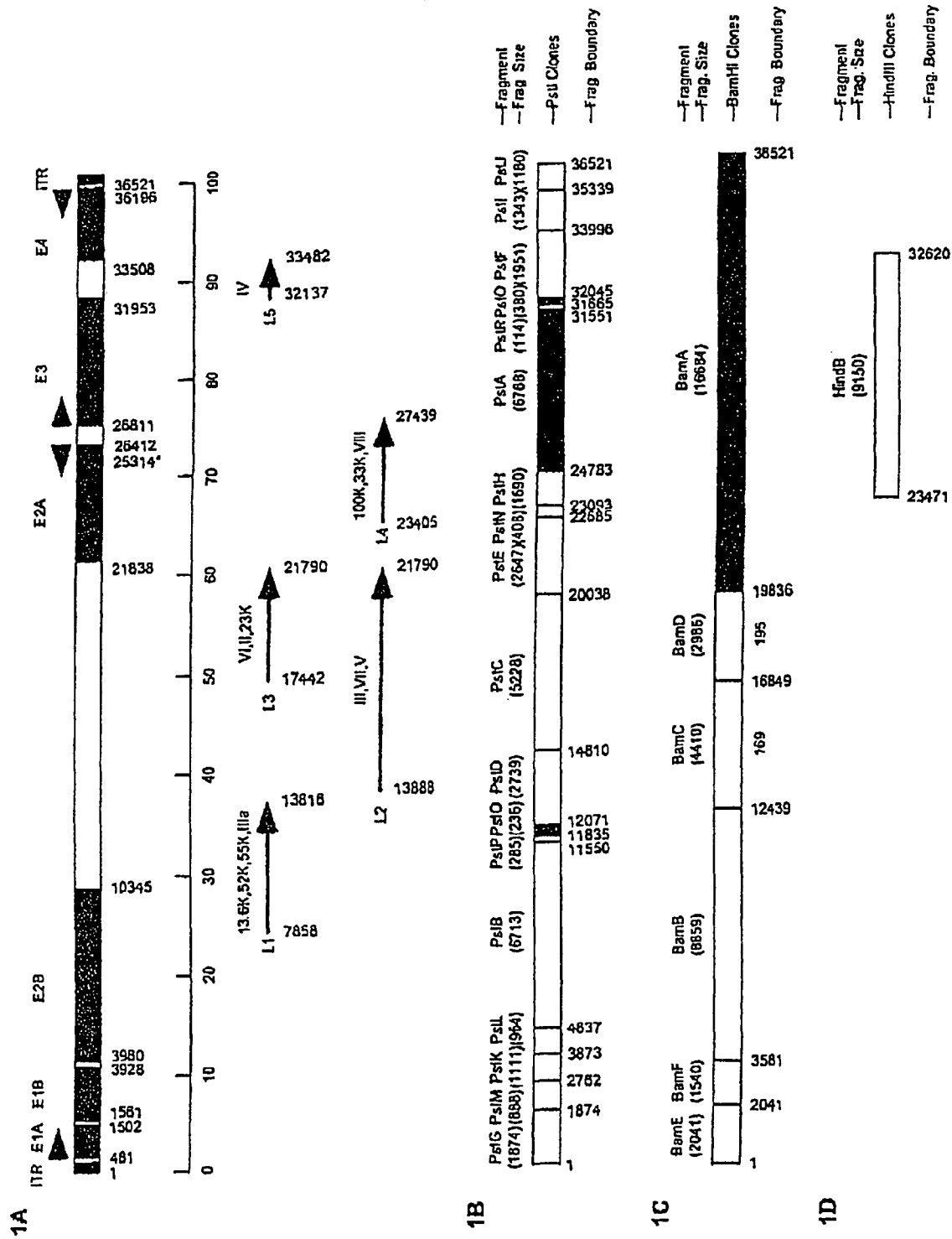
FIG. 1 summarizes the genetic organization of the chimpanzee adenovirus C68 genome.

The present invention provides novel adenovirus capsid proteins derived from the unique sequences of chimpanzee adenovirus C68. The capsid proteins of the invention are useful for a variety of purposes, including non-viral targeted delivery to cells and for creating recombinant viral vectors. These proteins and viral vectors are useful for delivery of heterologous molecules to target cells.

The invention further provides a novel method for rapid screening of bacterial transformants obtained during production of the novel adenoviral capsids of the invention, and during production of a variety of other viral or non-viral constructs. In this method, at least the shuttle vector is engineered to contain a marker gene, e.g., green fluorescent protein (GFP), gene under the control of a suitable promoter. The transformed cells are screened for expression of marker. In the case of GFP, white colonies are recombinants while green colonies are residual parental plasmid.

I. Novel Adenovirus Capsid Proteins

In one aspect, the invention provides unique C68 adenoviral capsid proteins, including the C68 hexon region, the C68 penton region, and the C68 fiber region, and fragments thereof. Suitably, these capsid proteins can be substantially pure, i.e., are free of other proteins. Preferably, these proteins are at least 10% homogeneous, more preferably 60% homogeneous, and most preferably 95% homogeneous.

In addition, the invention provides unique C68-derived capsid proteins. As used herein, a C68-derived capsid protein includes any C68 capsid protein or a fragment thereof including, without limitation, a polypeptide, peptide or a consecutive sequence of at least 8 amino acid residues unique to a C68 capsid protein and which is free of other proteins. A C68-derived capsid protein also includes a capsid protein that contains a C68 capsid protein or fragment thereof as defined above, including, without limitation, a chimeric capsid protein, a fusion protein, an artificial capsid protein, a synthetic capsid protein, and a recombinant capsid protein, without limitation to means of generating these proteins. Suitably, these C68-derived capsid proteins contain one or more C68 regions or fragments thereof (e.g., a hexon) in combination with capsid regions or fragments thereof of different adenoviral serotypes, or of non-adenoviral sources, as described herein. These C68-derived capsid proteins may be used in non-viral targeting of useful molecules to cells, or for production of viral vectors, as described herein.

A "modification of a capsid protein associated with altered tropism" as used herein includes an altered capsid protein, i.e, a penton, hexon or fiber protein region, or fragment thereof, such as the knob domain of the fiber region, or a polynucleotide encoding same, such that specificity is altered.

In one embodiment, the amino acid sequences of the C68 penton protein are provided in SEQ ID NO:12: MRRAYPEGPPPSYESVMQQAMAAAAMQPPLE PYVPPRYLAPTEGRNSIRYSELAPLYDTTR-LYLVDNKSADIASLNYQNDHSNFLTTVV QNNDFTPTEASTQTINFDERSRWGGQLK-TIMHTNMPNVNEFMYSNKFKARVMVSR KTP-NGVTVTEDYDGSQDELKYEWVEFELPEG-NFSVTMTILMNNAIIDNYLAVGRQN GVLESDIGVKFDTRNFRLGWD-PVTELVMPGVYTNEAFHPIVLLPGCGVDFTESRLSN LLIRKRQPFQEGFQIMYEDLEG-GNIPALLDVDAYEKSKEDAAAATAAVATASTEVRG DNFASAAAVAAAEAA-ETESKIVIQPVEKDSKNRSYNVLPDKIN-TYRSWYLAYNYGD PEGVRSWTLLTTSD-VTCGVEQVYWSLPDMMQDPVTFRSTRQVSNYPVV GAELLPV YSKSFFNEQAVYSQQLRAFTSLTHVFNR-FPENQILVRPPAPTITTVSENVPALTDHGTL PLRSSIR-GVQRVTVTDARRRTCPYVYKALGIVAPRVLSSRTF.

Suitably, this penton protein, or unique fragments thereof, may be utilized for a variety of purposes. Examples of suitable fragments include the C68 penton having N-terminal and/or C-terminal truncations of about 50, 100, 150, or 200 amino acids, based upon the amino acid numbering provided above and in SEQ ID NO:12. Other suitable fragments include shorter internal, C-terminal, or N-terminal fragments. Further, the penton protein may be modified for a variety of purposes known to those of skill in the art.

The sequences of the C68 hexon are provided in SEQ ID NO:16:

MATPSMLPQWAYMHIAGQDASEYLSPGLVQFARATDTYFSLGNKFRNPTV

APTHDTTDRSQRLTLRFVPVDREDNTYSYKVRYTLAVGDNRVLDMASTYF

DIRGVLDRGPSFKPYSGTAYNSLAPKGAPNTCQWTYKADGETATEKTYTY

GNAPVQGINITKDIQLGTDTDDQPIYADKTYQPEPQVGDAEWHDITGTDE

KYGGRALKPDTKMKPCYGSFAKPTNKEGGQANVKTGTGTTKEYDIDMAFF

DNRSAAAAGLAPEIVLYTENVDLETPDTHIVYKAGTDDSSSSINLGQQAM

PNRPNYIGFRDNFIGLMYYNSTGNMGVLAGQASQLNAVVDLQDRNTELSY

QLLLDSLGDRTRYFSMWNQAVDSYDPDVRIIENHGVEDELPNYCFPLDAV

GRTDTYQGIKANGTDQTTWTKDDSVNDANEIGKGNPFAMEINIQANLWRN

FLYANVALYLPDSYKYTPANVTLPTNTNTYDYMNGRVVAPSLVDSYINIG

ARWSLDPMDNVNPFNHHRNAGLRYRSMLLGNGRYVPFHIQVPQKFFAIKS

LLLLPGSYTYEWNFRKDVNMILQSSLGNDLRTDGASISFTSINLYATFFP

MAHNTASTLEAMLRNDTNDQSFNDYLSAANMLYPIPANATNVPISIPSRN

WAAFRGWSFTRLKTKETPSLGSGFDPYFVYSGSIPYLDGTFYLNHTFKKV

SITFDSSVSWPGNDRLLTPNEFEIKRTVDGEGYNVAQCNMTKDWFLVQML

AHYNIGYQGFYVPEGYKDRMYSFFRNFQPMSRQVVDEVNYKDYQAVTLAY

QHNNSGFVGYLAPTMRQGQPYPAXYPYPLIGKSAVTSVTQKKFLCDRVMW

RIPFSSNFMSMGALTDLGQNMLYANSAHALDMNFEVDPMDESTLLYVVFE

VFDVVRVHQPHRGVIEAVYXRTPFSAGNATT.

Suitably, this hexon protein, or unique fragments thereof, may be utilized for a variety of purposes. Examples of suitable fragments include the C68 hexon having N-terminal and/or C-terminal truncations of about 50, 100, 150, 200, 300, 400, or 500 amino acids, based upon the amino acid numbering provided above and in SEQ ID NO:16. Other suitable fragments include shorter internal, C-terminal, or N-terminal fragments. For example, one suitable fragment is the loop region (domain) of the hexon protein, designated DE1 and FG1, or a hypervariable region thereof. Such fragments include the regions spanning amino acid residues about 125 to 443; about 138 to 441, or smaller fragments, such as those spanning about residue 138 to residue 163; about 170 to about 176; about 195 to about 203; about 233 to about 246; about 253 to about 264; about 287 to about 297; and about 404 to about 430 of C68, with reference to SEQ ID NO:16. Other suitable fragments may be readily identified by one of skill in the art. Further, the hexon protein may be modified for a variety of purposes known to those of skill in the art.

In one example, it may be desirable to generate an adenovirus having an altered hexon protein utilizing the C68 hexon protein sequences of the invention. One suitable method for altering hexon proteins is described in U.S. Pat. No. 5,922,315, which is incorporated by reference. In this method, at least one loop region of the adenovirus hexon is changed with at least one loop region of another adenovirus serotype. Thus, at least one loop region of such an altered adenovirus hexon protein is a C68 hexon loop region. In one embodiment, a loop region of the C68 hexon protein is replaced by a loop region from another adenovirus serotype. In another embodiment, the loop region of the C68 hexon is used to replace a loop region from another adenovirus serotype. Suitable adenovirus serotypes may be readily selected from among human and non-human serotypes, as described herein. Where non-human adenoviruses are selected, the serotypes are preferably selected from non-human primates. However, the selection of a suitable serotype is not a limitation of the present invention. Still other uses for the C68 hexon protein sequences of the invention will be readily apparent to those of skill in the art.

The sequences of the C68 fiber protein are: SEQ ID NO:27:

MSKKRVRVDDDFDPVYPYDADNAPTVPFINPPFVSSDGFQEKPLGVLSLR

LADPVTTKNGEITLKLGEGVDLDSSGKLISNTATKAAAPLSFSNNTISLN

MDPFYTKDGKLSLQVSPPLNILRTSILNTLALGFGSGLGLRGSALAVQLV

SPLTFDTDGNIKLTLDRGLHVTTGDAIESNISWAKGLKFEDGAIATNIGN

GLEFGSSSTETGVDDAYPIQVKLGSGLSFDSTGAIMAGNKEDDKLTLWTT

PDPSPNCQILAENDAKLTLCLTKCGSQILATVSVLVVGSGNLNPITGTVS

SAQVFLRFDANGVLLTEHSTLKKYWGYRQGDSIDGTPYTNAVGFMPNLKA

YPKSQSSTTKNNIVGQVYMNGDVSKPMLLTITLNGTDDSNSTYSMSFSYT

WTNGSYVGATFGANSYTFSYIAQE.

Suitably, this fiber protein, or unique fragments thereof, may be utilized for a variety of purposes. One suitable fragment is the fiber knob, which spans about amino acids 247 to 425 of SEQ ID NO: 27. Examples of other suitable fragments include the C68 fiber having N-terminal and/or C-terminal truncations of about 50, 100, 150, or 200 amino acids, based upon the amino acid numbering provided above and in SEQ ID NO:27. Still other suitable fragments include internal fragments. Further, the fiber protein may be modified using a variety of techniques known to those of skill in the art.

The amino acid sequences of other useful gene products of C68 are provided in SEQ ID Nos. 1-11, 13-15, 17-26, and 28-38 of the attached sequence listing. More particularly, these sequences are as follows.

| Regions | | Ad C68 - CDS, With ref to SEQ ID NO: 33. | Ad C68 SEQ ID NO: |
|---|---|---|---|
| E1a | 11 kDa | 578 . . . 649, 1236 . . . 1469 | 1 |
| | 28.2 kDa | 578 . . . 1142, 1236 . . . 1444 | 2 |
| | 24.8 kDa | 578 . . . 1049, 1236 . . . 1444 | 3 |
| E1b | 20.5 kDa | 1603 . . . 2163 | 4 |
| | 54.7 kDa | 1908 . . . 3404 | 5 |
| | 18.5 kDa | 1908 . . . 2200, 3188 . . . 3404 | 6 |
| | 10.1 kDa | 1908 . . . 2170, 3306 . . . 3324 | 7 |
| IX | Hexon-associated protein - pIX | 3489 . . . 3917 | 8 |
| IVa2 | Maturation protein - pIVa2 | Complement (3976 . . . 5309, 5588 . . . 5600) | 9 |
| L1 | 21.9 kDa | 7858 . . . 8460 | 10 |
| | 42.9 kDa | 10825 . . . 12000 | 11 |
| L2 | Penton - pIII | 13888 . . . 15492 | 12 |
| | Major core protein - pVIII | 15493 . . . 16098 | 13 |
| | Minor Core Protein - pV | 16120 . . . 17190 | 14 |
| L3 | Hexon-associated protein - pVI | 17442 . . . 18215 | 15 |
| | Hexon - pII | 18322 . . . 21123 | 16 |
| E2a | DNA-Binding Protein Endopeptidase | Complement (21835 . . . 23376) | 17 |

-continued

| Regions | | Ad C68 - CDS, With ref to SEQ ID NO: 33. | Ad C68 SEQ ID NO: |
|---|---|---|---|
| L4 | Virion morphogenesis-associated protein 24.3 kDa | Complement (25529 . . . 25862, 26032 . . . 26366) | 18 |
| | Hexon-associated protein - pVIII | 26446 . . . 27129 | 19 |
| E3 | 11.6 kDa | 27130 . . . 27450 | 20 |
| | 16 kDa | (27404 . . . 27477, 27666 . . . 28032) | 21 |
| | 19.3 kDa | 28014 . . . 28544 | 22 |
| | 22.3 | 28572 . . . 29186 | 23 |
| | 9.9 kDa | 30722 . . . 30997 | 24 |
| | 15.6 kDa | 31003 . . . 31434 | 25 |
| | 14.7 kDa | 31427 . . . 31834 | 26 |
| L5 | Fiber - pIV | 32137 . . . 33414 | 27 |
| E4 | ORF7-like protein | Complement (33521 . . . >33772) | 28 |
| | Orf 6 - 33 kDa | Complement (33769 . . . 34674) | 29 |
| | Orf4 - 13.2 kDa | Complement (34580 . . . 34945) | 30 |
| | Orf 3 - 12.8 kDa | Complement (34955 . . . 35308) | 31 |
| | Orf 2 - 14.2 kDa | Complement (35305 . . . 35694) | 32 |

Thus, the invention provides unique C68 proteins, peptides and fragments thereof, which are produced recombinantly or by other methods. Suitably, such fragments are at least 8 amino acids in length. However, fragments of other desired lengths are readily utilized. In addition, the invention encompasses such modifications as may be introduced to enhance yield and/or expression of a C68 protein or fragment, construction of a fusion molecule in which all or a fragment of the C68 protein or fragment is fused (either directly or via a linker) with a fusion partner to enhance. Other suitable modifications include, without limitation, truncation of a coding region (e.g., a protein or enzyme) to eliminate a pre- or pro-protein ordinarily cleaved to produce the mature protein or enzyme and/or mutation of a coding region to provide a secretable gene product. Still other modifications will be readily apparent to one of skill in the art. The invention further encompasses proteins having at least about 95% to 99% identity to the C68 proteins provided herein.

The term "substantial homology" or "substantial similarity," when referring to a protein or fragment thereof, indicates that, when optimally aligned with appropriate amino acid insertions or deletions with another protein, there is nucleotide sequence identity in at least about 95 to 99% of the aligned sequences.

The term "percent sequence identity" or "identical" in the context of proteins or fragments thereof refers to the amino acids in the two sequences that are the same when aligned for maximum correspondence. The length of sequence identity comparison may be over the full length of a protein, enzyme, polypeptide, peptide, or other fragment of at least about 200 to 500 amino acids, if desired. However, identity among smaller fragments, e.g. of at least about 8 amino acids, usually at least about 20 to 24 amino acids, at least about 28 to 32 amino acids, at least about 50 or more amino acids, may also be desired.

Identity is readily determined by one of skill in the art by resort to algorithms and computer programs known by those of skill in the art. As described herein, alignments are performed using any of a variety of publicly or commercially available Multiple Sequence Alignment Programs, such as "Clustal W", accessible through Web Servers on the internet. Alternatively, Vector NTI utilities are also used. There are also a number of algorithms known in the art that can be used to measure amino acid sequence identity, including those contained in the programs described above. Generally, these programs are used at default settings, although one of skill in the art can alter these settings as needed. Alternatively, one of skill in the art can utilize another algorithm or computer program that provides at least the level of identity or alignment as that provided by the referenced algorithms and programs.

As described herein, the C68-derived capsid proteins of the invention are particularly well suited for use in applications in which the neutralizing antibodies diminish the effectiveness of other Ad serotype based targeting proteins and vectors, as well as other viral vectors. The C68-derived constructs of the invention are particularly advantageous in readministration for repeat gene therapy or for boosting immune response (vaccine titers).

Also provided by the present invention are artificial adenoviral capsid proteins, which involve modifications and chimeric capsids constructed using the C68 adenoviral capsid proteins of the invention. Such artificial capsid proteins can be constructed using the amino acid sequences of the chimp C68 Ad hexon of the invention. Because the hexon protein is the determinant for serotype of an adenovirus, such artificial hexon proteins would result in adenoviruses having artificial serotypes. Other artificial capsid proteins can also be constructed using the chimp Ad penton sequences and/or fiber sequences of the invention and/or fragments thereof.

In one embodiment, a chimeric C68 capsid is constructed using C68 hexon and C68 fiber and a penton from another adenovirus. Alternatively, a chimeric C68 capsid comprises a C68 hexon and a fiber and penton from one or more different adenoviruses. Another chimeric adenovirus capsid comprises the C68 fiber and a penton and a hexon from one or more different adenovirus serotypes. Yet another chimeric adenovirus capsid comprises the C68 penton and a fiber and hexon from one or more different adenovirus serotypes. Suitably, for such chimeric and artificial capsids constructed from C68 proteins, the non-C68 adenovirus components may be readily selected from other adenovirus serotypes.

Under certain circumstances, it may be desirable to use one or more of the C68-derived capsid proteins or a fragment thereof to generate an antibody. The term "an antibody," as used herein, refers to an immunoglobulin molecule which is able to specifically bind to an epitope. The antibodies in the present invention exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE. Such antibodies may be generated using any of a number of methods know in the art. Suitable antibodies may be generated by well-known conventional techniques, e.g. Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., 1986 *Science*, 233:747-753; Queen et al., 1989 *Proc. Nat'l. Acad. Sci. USA,* 86:10029-10033; PCT Patent Application No. PCT/WO9007861; and Riechmann et al., *Nature,* 332:323-327 (1988); Huse et al, 1988a *Science,* 246: 1275-1281]. Alternatively, antibodies can be produced by manipulating the complementarity determining regions of animal or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, *Proc. Natl. Acad. Sci. USA* 85:5879-5883; and Bird et al., 1988, *Science* 242:423-426.

Alternatively, one or more of the C68 capsid proteins of the invention are assembled as multi-antigenic complexes [see, e.g., European Patent Application 0339695, published Nov. 2, 1989] and employed to elicit high titer antibodies. Further provided by the present invention are anti-idiotype antibodies (Ab2) and anti-anti-idiotype antibodies (Ab3). See, e.g., M. Wettendorff et al., "Modulation of anti-tumor immunity by anti-idiotypic antibodies." In Idiotypic Network and Diseases, ed. by J. Cerny and J. Hiernaux, 1990 *J. Am. Soc. Microbiol.*, Washington D.C.: pp. 203-229]. These anti-idiotype and anti-anti-idiotype antibodies are produced using techniques well known to those of skill in the art. These antibodies may be used for a variety of purposes, including diagnostic and clinical methods and kits.

Under certain circumstances, it may be desirable to introduce a detectable label or a tag onto a C68 antibody or other construct of the invention. As used herein, a detectable label is a molecule which is capable, alone or upon interaction with another molecule, of providing a detectable signal. Most desirably, the label is detectable visually, e.g. by fluorescence, for ready use in immunohistochemical analyses or immunofluorescent microscopy. For example, suitable labels include fluorescein isothiocyanate (FITC), phycoerythrin (PE), allophycocyanin (APC), coriphosphine-O (CPO) or tandem dyes, PE-cyanin-5 (PC5), and PE-Texas Red (ECD). All of these fluorescent dyes are commercially available, and their uses known to the art. Other useful labels include a colloidal gold label. Still other useful labels include radioactive compounds or elements. Additionally, labels include a variety of enzyme systems that operate to reveal a colorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength. Other label systems that are utilized in the methods of this invention are detectable by other means, e.g., colored latex microparticles [Bangs Laboratories, Indiana] in which a dye is embedded are used in place of enzymes to form conjugates with the target sequences provide a visual signal indicative of the presence of the resulting complex in applicable assays.

Methods for coupling or associating the label with a desired molecule are similarly conventional and known to those of skill in the art. Known methods of label attachment are described [see, for example, Handbook of Fluorescent probes and Research Chemicals, 6th Ed., R. P. M. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

The C68-derived proteins, peptides, and fragments described herein can be produced by any suitable means, including chemical synthesis, or other synthetic means, or by recombinant production and conventional genetic engineering methodologies. For example, peptides can be synthesized by the well known solid phase peptide synthesis methods (Merrifield, *J. Am. Chem. Soc.,* 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

Alternatively, suitable methods for recombinant production can be used. Selection of suitable expression systems, including expression vectors and host cells for protein expression and/or viral packaging is within the ability of one of skill in the art and is not a limitation of the present invention. See, e.g., Sambrook et al, Molecular Cloning: A Laboratory Manual, Cold Spring Harbor Press (Cold Spring Harbor, N.Y.).

Nucleic acid sequences for the C68 genome, which is 36521 by in length, may be obtained using information available in U.S. Pat. No. 6,083,716 and from the American Type Culture Collection, 10801 University Boulevard, Manassas, Va. 20110-2209 (Pan-9). This sequence is also available from GenBank. Other chimpanzee adenovirus sequences are available from the American Type Culture Collection, 10801 University Boulevard, Manassas, Va. 20110-2209, and other sources. Desirable chimpanzee strains are Pan 5 [ATCC VR-591], Pan 6 [ATCC VR-592], and Pan 7 [ATCC VR-593]. Another particularly desirable chimpanzee adenovirus strain is chimpanzee adenovirus strain Bertha or C1 [ATCC Accession No. VR-20]. The sequence of the C1 serotype, and the location of the adenovirus genes E1a, E1b, E2a, E2b, E3, E4, L1, L2, L3, L4 and L5 are provided in U.S. Pat. No. 6,083,716, which is incorporated by reference herein. Optionally, non-chimpanzee simian adenoviral sequences may be used. Such non-chimpanzee adenovirus include those obtained from baboon adenovirus strains [e.g., ATCC VR-275], adenovirus strains isolated from rhesus monkeys [e.g., ATCC VR-209, ATCC VR-275, ATCC VR-353, ATCC VR-355], and adenovirus strains isolated from African green monkeys [e.g., ATCC VR-541; ATCC VR-941; ATCC VR-942; ATCC VR-943]. Alternatively, one may readily select from among the at least 51 different human serotypes, including, without limitation, human adenovirus serotypes 1, 2, 3, 4, 5, 12, 35, 37, and 40, and other, non-human primate adenovirus serotypes. Further, the sequences of these and other suitable serotypes are available from a variety of databases including, e.g., PubMed and GenBank [see, for example, U.S. Pat. No. 5,240,846]. Selection of an appropriate adenovirus is not a limitation of the present invention.

The invention further provides molecules useful for production of the C68 and C68-derived proteins of the invention, including such molecules which carry polynucleotides including DNA sequences. Thus, the invention further encompasses the nucleic acid sequences encoding the C68-derived constructs of the invention, and molecules and host cells useful in expression thereof, including suitable DNA molecules and vectors, which can be any suitable genetic element as defined herein. Preferably, these vectors are DNA-based (e.g., plasmids) or viral vectors.

In one embodiment, the C68-derived capsid proteins and other C68 adenovirus proteins described herein are used for non-viral, protein-based delivery of genes, proteins, and other desirable diagnostic, therapeutic and immunogenic molecules. A desired molecule for delivery to a target call may be associated with a C68-derived capsid protein or other protein by any suitable means, including, e.g., covalent or non-covalent binding. For example, the C68 penton protein may be readily utilized for such a purpose by production of a fusion protein using the C68 penton sequences of SEQ ID NO:12 in a manner analogous to that described in Medina-Kauwe L K, et al, *Gene Ther.* 2001 May; 8(10):795-803 and Medina-Kauwe L K, et al, *Gene Ther.* 2001 December; 8(23): 1753-1761. Alternatively, the amino acid sequences of C68 protein IX may be utilized for targeting vectors by associating the protein IX with a ligand that binds to a cell surface receptor, as described in US Patent Appln 20010047081. Suitable ligands include a CD40 antigen, an RGD-containing or polylysine-containing sequence, and the like. Still other C68 proteins may be used for used for these and similar purposes.

Further, the C68 adenovirus proteins of the invention are particularly well suited for use in producing viral vectors in C68-derived capsids. Suitably, these adenoviruses are pseudotyped such that a nucleic acid molecule carrying adenovirus ITRs from a non-C68 serotype and a minigene are packaged in a C68-derived adenoviral capsid of the invention. Alternatively, adenoviruses may be generated which contain at least the 5' ITRs or the 3' ITRs from C68, in a C68-derived capsid protein. The adenoviral vectors described herein may contain adenoviral sequences derived from one, or more than one adenoviral strain. In yet another alternative, other C68 elements described herein may be utilized in production of recombinant vectors, or other desirable constructs.

The C68 proteins of the invention are useful for a variety of purposes, including construction of recombinant viruses. The C68-derived capsid proteins of the invention are useful in producing hybrid vectors, including, hybrid C68-adeno-associated viruses, Epstein-Barr virus, and retroviruses [Caplen et al, *Gene Ther.* 6: 454-459 (1999); Tan et al, *J. Virol.,* 73:7582-7589 (1999)]. Such viruses include C68-derived capsids which encapsidated vectors with adeno-associated virus (AAV) ITRs [Lieber et al, *J Virol,* 73:9314-9324 (1999), Recchia et al, *Proc Natl Acad Sci USA,* 96:2615-2620 (1999); or lentivirus ITRs (Zheng et al, *Nat Biotech,* 18:176-180 (2000), using Maloney leukemia virus long terminal repeats).

In a particularly desirable embodiment, the C68-derived capsid proteins, and optionally, the other C68 sequences described herein, are used to produce recombinant adenoviruses and pseudotyped adenoviruses. However, it will be readily understood that the C68-derived capsid proteins and other novel C68 sequences can be utilized for a variety of purposes, including production of other types of viral vectors (such as, e.g., hybrid vectors) carrying the therapeutic and immunogenic transgenes described below. Additionally, it will be readily understood that viral vectors carrying the unique C68 proteins and other sequences of the invention can be utilized for targeting and/or delivery of other types of molecules, including proteins, chemical molecules and other moieties useful for diagnostic, therapeutic and/or immunization purposes.

II. Recombinant Adenoviral Vectors

The compositions of this invention include vectors that deliver a heterologous molecule to cells, either for therapeutic or vaccine purposes. As used herein, a vector may include any genetic element including, without limitation, a cosmid, episome, plasmid, or a virus. In a particularly preferred embodiment, these vectors are viral vectors having capsid proteins derived from the C68 proteins of the invention. Alternatively, these vectors may contain other C68 sequences of the invention. These viral vectors suitably contain a minigene. By "minigene" is meant the combination of a selected heterologous gene and the other regulatory elements necessary to drive translation, transcription and/or expression of the gene product in a host cell.

Typically, an adenoviral vector is designed such that the minigene is flanked on its 5' end and/or its 3' end by adenoviral sequences which include, at a minimum, the cis-elements necessary for replication and virion encapsidation. Thus, in one embodiment, the vector contains adenoviral sequences encompassing at least the 5' end of the adenoviral genome, i.e., the 5' inverted terminal repeat sequences (which functions as origins of replication) and the native 5' packaging enhancer domains (that contain sequences necessary for packaging linear Ad genomes and enhancer elements for the E1 promoter). The vector is also provided with the cis-acting 3' ITRs. Suitably, the minigene is located between the 5' adenoviral elements and the 3' adenoviral elements. An adenoviral vector of the invention may also contain additional adenoviral sequences. For example, the minigene may be located in the site of such as the site of a functional E1 deletion or functional E3 deletion, among others that may be selected. Alternatively, the minigene may be inserted into an existing gene region to disrupt the function of that region, if desired.

The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed.

Suitably, these adenoviral vectors of the invention contain one or more adenoviral elements derived from C68. In one embodiment, the vectors contain adenoviral ITRs from an adenoviral serotype which differs from C68. Alternatively, C68 ITRs may be utilized in a viral vector of the invention in which the capsid is not naturally occurring, but contains one or more C68 proteins, or fragments thereof. The selection of the serotype of the ITRs and the serotype of any other adenoviral sequences present in the vector is not a limitation of the present invention. A variety of adenovirus strains are described herein.

The viral sequences, helper viruses, if needed, and recombinant viral particles, and other vector components and sequences employed in the construction of the vectors described herein are obtained as described above. See, e.g., U.S. Pat. No. 5,240,846. The DNA sequences of the adenovirus sequences are employed to construct vectors and cell lines useful in the preparation of such vectors. See, e.g., U.S. Pat. No. 6,083,716.

Modifications of the nucleic acid sequences forming the vectors of this invention, including sequence deletions, insertions, and other mutations may be generated using standard molecular biological techniques and are within the scope of this invention.

A. The "Minigene"

The methods employed for the selection of the transgene, the cloning and construction of the "minigene" and its insertion into the viral vector are within the skill in the art given the teachings provided herein.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is GFP or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a molecule (e.g., a gene product) to induce a T cell and/or a humoral immune response to the molecule. The invention further includes using multiple transgenes, e.g., to correct or ameliorate a condition caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.*, 78 (Pt 1): 13-21 (January 1997); Furler, S., et al, *Gene Ther.*, 8 (11):864-873 (June 2001); Klump H., et al., *Gene Ther.*, 8 (10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements necessary which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), see also Harvey et al, *Curr. Opin. Chem. Biol.,* 2:512-518 (1998)]. Other systems include the FK506 dimer, VP16 or p65 using castradiol, diphenol murislerone, the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. The effectiveness of some inducible promoters increases over time. In such cases one can enhance the effectiveness of such systems by inserting multiple repressors in tandem, e.g., TetR linked to a TetR by an IRES. Alternatively, one can wait at least 3 days before screening for the desired function. Once can enhance expression of desired proteins by known means to enhance the effectiveness of this system. For example, using the Woodchuck Hepatitis Virus Posttranscriptional Regulatory Element (WPRE).

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al., *Nat. Biotech.,* 17:241-245 (1999)). Examples of promoters that are tissue-specific are known for liver (albumin, Miyatake et al., *J. Virol.,* 71:5124-32 (1997); hepatitis B virus core promoter, Sandig et al., *Gene Ther.,* 3:1002-9 (1996); alpha-fetoprotein (AFP), Arbuthnot et al., *Hum. Gene Ther.,* 7:1503-14 (1996)), bone osteocalcin (Stein et al., *Mol. Biol. Rep.,* 24:185-96 (1997)); bone sialoprotein (Chen et al., *J. Bone Miner. Res.,* 11:654-64 (1996)), lymphocytes (CD2, Hansal et al., *J. Immunol.,* 161:1063-8 (1998); immunoglobulin heavy chain; T cell receptor chain), neuronal such as neuron-specific enolase (NSE) promoter (Andersen et al., *Cell. Mol. Neurobiol.,* 13:503-15 (1993)), neurofilament light-chain gene (Piccioli et al., *Proc. Natl. Acad. Sci. USA,* 88:5611-5 (1991)), and the neuron-specific vgf gene (Piccioli et al., *Neuron,* 15:373-84 (1995)), among others.

Optionally, vectors carrying transgenes encoding therapeutically useful or immunogenic products may also include selectable markers or reporter genes which may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication. Selection of these and other promoters and vector elements are conventional and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

III. Production of the Recombinant Viral Particle

In one embodiment, the chimpanzee adenoviral plasmids (or other vectors) are used to produce recombinant adenoviral particles. In one embodiment, the recombinant adenoviruses are functionally deleted in the E1a or E1b genes, and optionally bearing other mutations, e.g., temperature-sensitive mutations or deletions in other genes. In other embodiments, it is desirable to retain an intact E1a and/or E1b region in the recombinant adenoviruses. Such an intact E1 region may be located in its native location in the adenoviral genome or placed in the site of a deletion in the native adenoviral genome (e.g., in the E3 region).

In the construction of useful chimpanzee adenovirus vectors for delivery of a gene to the human (or other mammalian) cell, a range of adenovirus nucleic acid sequences can be employed in the vectors. For example, all or a portion of the adenovirus delayed early gene E3 may be eliminated from the C68 adenovirus sequence which forms a part of the recombinant virus. The function of adenovirus E3 is believed to be irrelevant to the function and production of the recombinant virus particle. Adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the chimpanzee adenovirus genome. Similarly, deletions in the intermediate genes IX and IVa$_2$ may be useful for some purposes. Other deletions may be made in the other structural or non-structural adenovirus genes. The above discussed deletions may be used individually, i.e., an adenovirus sequence for use in the present invention may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

An adenoviral vector lacking any essential adenoviral sequences (e.g., E1a, E1b, E2a, E2b, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell. See, for example, the techniques described for preparation of a "minimal" human Ad vector in International Patent Application WO96/13597, published May 9, 1996, and incorporated herein by reference.

1. Helper Viruses

Thus, depending upon the chimpanzee adenovirus gene content of the viral vectors employed to carry the minigene, a helper adenovirus or non-replicating virus fragment may be necessary to provide sufficient chimpanzee adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 264:16985-16987 (1989); K. J. Fisher and J. M. Wilson, *Biochem. J,* 299:49 (Apr. 1, 1994). Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification.

2. Complementation Cell Lines

To generate recombinant chimpanzee adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human E1 can be used to transcomplement the chimp Ad vector. This is particularly advantageous because, due to the diversity between the chimp Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line which expresses the E1 gene products can be utilized for production of an E1-deleted chimpanzee adenovirus. Such cell lines have been described. See, e.g., U.S. Pat. No. 6,083,716.

If desired, one may utilize the sequences provided herein to generate a packaging cell or cell line that expresses, at a minimum, the adenovirus E1 gene under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired Ad gene. Without limitation, such a parent cell line may be HeLa [ATCC Accession No. CCL 2], A549 [ATCC Accession No. CCL 185], KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

Such E1-expressing cell lines are useful in the generation of recombinant chimpanzee adenovirus E1 deleted vectors. Additionally, or alternatively, the invention provides cell lines that express one or more chimpanzee adenoviral gene products, e.g., E1a, E1b, E2a, and/or E4 ORF6, can be constructed using essentially the same procedures for use in the generation of recombinant chimpanzee viral vectors. Such cell lines can be utilized to transcomplement adenovirus vectors deleted in the essential genes that encode those products, or to provide helper functions necessary for packaging of a helper-dependent virus (e.g., adeno-associated virus). The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus genomes, combined with polymerase chain reaction, synthetic methods, and any other suitable methods which provide the desired nucleotide sequence.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

3. Assembly of Viral Particle and Transfection of a Cell Line

Generally, when delivering the vector comprising the minigene by transfection, the vector is delivered in an amount from about 5 μg to about 100 μg DNA, and preferably about 10 to about 50 μg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

The vector may be any vector known in the art or disclosed above, including naked DNA, a plasmid, phage, transposon, cosmids, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include conventional cloning techniques of cDNA such as those described in texts, use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The current method for producing such virus particles is transfection-based. However, the invention is not limited to such methods.

The resulting recombinant chimpanzee adenoviruses are useful in transferring a selected transgene to a selected cell. In in vivo experiments with the recombinant virus grown in the packaging cell lines, the E1-deleted recombinant chimpanzee adenoviral vectors of the invention demonstrate utility in transferring a transgene to a non-chimpanzee, preferably a human, cell.

IV. Use of Non-Viral C68 Proteins and C68-Derived Adenoviruses

The recombinant adenovirus vectors of the invention are useful for gene transfer to a human or non-chimpanzee veterinary patient in vitro, ex vivo, and in vivo. In addition, a variety of C68 proteins described herein are useful in non-viral targeting of transgenes, proteins, chemical molecules, and other moieties or molecules to cells. Suitable methods of delivery and dosing regimens are readily determined based upon the targeted molecule and targeting protein. Examples of suitable genes and sources of proteins for protein-mediated delivery are provided in the sections below relating to viral delivery of therapeutic and immunogenic molecules. While the discussion below focuses on viral vectors, it will be appreciated that the C68-derived proteins of the invention may be formulated as described herein for the C68-derived viral vectors and the same routes of administration and regimens may be utilized.

The recombinant adenovirus vectors described herein can be used as expression vectors for the production of the products encoded by the heterologous genes in vitro. For example, the recombinant adenoviruses containing a gene inserted into the location of an E1 deletion may be transfected into an E1-expressing cell line as described above. Alternatively, replication-competent adenoviruses may be used in another selected cell line. The transfected cells are then cultured in the conventional manner, allowing the recombinant adenovirus to express the gene product from the promoter. The gene product may then be recovered from the culture medium by known conventional methods of protein isolation and recovery from culture.

A C68-derived vector or C68-derived protein of the invention provides an efficient gene transfer vehicle that can deliver a selected transgene or other molecule to a selected host cell in vivo or ex vivo even where the organism has neutralizing antibodies to one or more AAV serotypes. In one embodiment, the rAAV and the cells are mixed ex vivo; the infected cells are cultured using conventional methodologies; and the transduced cells are re-infused into the patient. These compositions are particularly well suited to gene delivery for therapeutic purposes and for immunization, including inducing protective immunity.

More commonly, the C68-derived vectors and C68-derived proteins of the invention will be utilized for delivery of therapeutic or immunogenic molecules, as described below. It will be readily understood for both applications, that the C68-derived constructs of the invention are useful for use in regimens involving single administrations, as well as in regimens involving repeat delivery of adenoviral vectors or non-viral targeted delivery, or repeat delivery of the transgene or other molecule to the cells.

Such regimens typically involve delivery of a series of viral vectors in which the viral capsids are alternated. The viral capsids may be changed for each subsequent administration, or after a pre-selected number of administrations of a particular serotype capsid (e.g., one, two, three, four or more). For example, a regimen may involve delivery of a rAd with a C68-derived capsid and delivery with a rAd with another human or non-human primate adenovirus serotype. Optionally, these regimens may involve administration of rAd with capsids of other non-human primate adenoviruses, human adenoviruses, or artificial serotypes such as are described herein. Alternatively, the regimens involve administration of C68-derived proteins for non-viral targeting with repeat administrations of C68-derived proteins, or with other protein-based delivery systems. Each phase of these regimens can involve administration of a series of injections (or other delivery routes) with a single C68-derived construct followed by a series with another Ad serotype construct. Alternatively, the C68-derived vectors and proteins of the invention may be utilized in regimens involving other non-adenoviral-mediated delivery systems, including other viral systems, non-viral delivery systems, protein, peptides, and other biologically active molecules.

The following sections will focus on exemplary molecules which may be delivered via the adenoviral vectors of the invention.

A. Ad-Mediated Delivery of Therapeutic Molecules

In one embodiment, the above-described C68-derived constructs are administered to humans according to published methods for gene therapy. A C68-derived construct bearing a transgene can be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The C68-derived adenoviral vectors are administered in sufficient amounts to transduce the target cells and to provide sufficient levels of gene transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the retina and other intraocular delivery methods, direct delivery to the liver, intranasal, intravenous, intramuscular, intratracheal, subcutaneous, intradermal, rectal, oral and other parenteral routes of administration. Routes of administration may be combined, if desired, or adjusted depending upon the transgene or the condition. The route of administration primarily will depend on the nature of the condition being treated.

Dosages of the viral vector will depend primarily on factors such as the condition being treated, the age, weight and health of the patient, and may thus vary among patients. For example, a therapeutically effective adult human or veterinary dosage of the viral vector is generally in the range of from about 100 μL to about 100 mL of a carrier containing concentrations of from about $1 \times 10^6$ to about $1 \times 10^{15}$ particles, about $1 \times 10^{11}$ to $1 \times 10^{13}$ particles, or about $1 \times 10^9$ to $1 \times 10^{12}$ particles virus. Dosages will range depending upon the size of the animal and the route of administration. For example, a suitable human or veterinary dosage (for about an 80 kg animal) for intramuscular injection is in the range of about $1 \times 10^9$ to about $5 \times 10^{12}$ particles per mL, for a single site. Optionally, multiple sites of administration may be delivered. In another example, a suitable human or veterinary dosage may be in the range of about $1 \times 10^{11}$ to about $1 \times 10^{15}$ particles for an oral formulation.

When C68 proteins of the invention are utilized for targeted delivery, suitable dosage ranges, a therapeutically effective adult human or veterinary dosage of the construct is generally in the range of from about 100 μL to about 100 mL of a carrier containing concentrations of from about 0.01 μg to about 100 mg protein, about 0.1 μg to about 10 mg, about 1 μg to about 1 mg protein. Dosages will range depending upon the size of the animal and the route of administration. Routes of administration may be readily selected from any suitable route including, without limitation, the routes described above.

One of skill in the art may adjust these doses, depending on the route of administration, and the therapeutic or vaccinal application for which the C68-derived construct is employed. The levels of expression of the transgene, or for an immunogen, the level of circulating antibody, can be monitored to determine the frequency of dosage administration. Yet other methods for determining the timing of frequency of administration will be readily apparent to one of skill in the art.

An optional method step involves the co-administration to the patient, either concurrently with, or before or after administration of the C68-derived construct, of a suitable amount of a short acting immune modulator. The selected immune modulator is defined herein as an agent capable of inhibiting the formation of neutralizing antibodies directed against the recombinant vector of this invention or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the vector. A variety of useful immune modulators and dosages for use of same are disclosed, for example, in Yang et al., *J. Virol.*, 70 (9) (September, 1996); International Patent Application No. WO96/12406, published May 2, 1996; and International Patent Application No. PCT/US96/03035, all incorporated herein by reference.

1. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor (TGF), platelet-derived growth factor (PDGF), insulin growth factors I and II (IGF-I and IGF-II), any one of the transforming growth factor superfamily, including TGF, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-18, monocyte chemoattractant protein, leukemia inhibitory factor, granulocyte-macrophage colony stimulating factor, Fas ligand, tumor necrosis factors and, interferons, and, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene are particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides. Such target polypeptides and their ligands are also useful in forming fusion partners with a C68 protein of the invention.

Other suitable therapeutic polypeptides and proteins include those which may be useful for treating individuals suffering from autoimmune diseases and disorders by conferring a broad based protective immune response against targets that are associated with autoimmunity including cell receptors and cells which produce self-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

The C68-derived constructs of the invention are particularly well suited for therapeutic regimens in which multiple deliveries of transgenes is desired, e.g., in regimens involving redelivery of the same transgene or in combination regimens involving delivery of other transgenes. Such regimens may involve administration of a C68-derived construct, followed by re-administration with a vector from the same serotype adenovirus. Particularly desirable regimens involve administration of a C68-derived construct of the invention, in which the serotype of the viral vector delivered in the first administration differs from the serotype of the viral vector utilized in one or more of the subsequent administrations. For example, a therapeutic regimen involves administration of a C68-derived vector and repeat administration with one or more adenoviral vectors of the same or different serotypes. In another example, a therapeutic regimen involves administration of an adenoviral vector followed by repeat administration with a C68-derived vector of the invention which differs from the serotype of the first delivered adenoviral vector, and optionally further administration with another vector which is the same or, preferably, differs from the serotype of the vector in the prior administration steps. These regimens are not limited to delivery of adenoviral vectors constructed using the C68-derived capsids of the invention. Rather, these regimens can readily utilize constructs, including non-viral targeting proteins and viral vectors, from other adenoviral serotypes, including, without limitation, other chimpanzee adenoviral serotypes (e.g., C1, etc), other non-human primate adenoviral serotypes, or human adenoviral serotypes, in combination with one or more of the C68-derived constructs of the invention. Examples of such chimpanzee, other non-human primate and human adenoviral serotypes are discussed elsewhere in this document. Further, these therapeutic regimens may involve either simultaneous or sequential delivery of C68-derived constructs of the invention in combination with non-adenoviral vectors, non-viral vectors, and/or a variety of other therapeutically useful compounds or molecules. The present invention is not limited to these therapeutic regimens, a variety of which will be readily apparent to one of skill in the art.

B. Ad-Mediated Delivery of Immunogenic Transgenes

The C68-derived constructs of the invention, including viral vectors and proteins, may also be employed as immunogenic compositions. As used herein, an immunogenic composition is a composition to which a humoral (e.g., antibody) or cellular (e.g., a cytotoxic T cell) response is mounted to a transgene product delivered by the immunogenic composition following delivery to a mammal, and preferably a primate. The present invention provides a recombinant C68-derived Ad that can contain in any of its adenovirus sequence deletions a gene encoding a desired immunogen, or a C68 protein capable of targeting an immunogenic molecule. The C68-derived adenovirus is well suited for use as a live recombinant virus vaccine in different animal species compared to an adenovirus of human origin, but is not limited to such a use. The recombinant adenoviruses and C68 proteins can be used as prophylactic or therapeutic vaccines against any pathogen for which the antigen(s) crucial for induction of an immune response and able to limit the spread of the pathogen has been identified and for which the cDNA is available.

Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a vaccinal composition of the invention may be formulated to contain other components, including, e.g. adjuvants, stabilizers, pH adjusters, preservatives and the like. Such components are well known to those of skill in the vaccine art. Examples of suitable adjuvants include, without limitation, liposomes, alum, monophosphoryl lipid A, and any biologically active factor, such as cytokine, an interleukin, a chemokine, a ligands, and optimally combinations thereof. Certain of these biologically active factors can be expressed in vivo, e.g., via a polynucleotide, plasmid or viral vector. For example, such an adjuvant can be administered with a priming DNA vaccine encoding an antigen to enhance the antigen-specific immune response compared with the immune response generated upon priming with a DNA vaccine encoding the antigen only.

The recombinant adenoviruses are administered in a "an immunogenic amount", that is, an amount of recombinant adenovirus that is effective in a route of administration to transfect the desired cells and provide sufficient levels of expression of the selected gene to induce an immune response. Where protective immunity is provided, the recombinant adenoviruses are considered to be vaccine compositions useful in preventing infection and/or recurrent disease.

Alternatively, or in addition, the vectors of the invention may contain, or C68-capsid or other protein can be utilized to target a transgene encoding a peptide, polypeptide or protein which induces an immune response to a selected immunogen. The C68-derived viruses of this invention are expected to be highly efficacious at inducing cytolytic T cells and antibodies to the inserted heterologous antigenic protein expressed by the vector.

1. Immunogenic Transgenes

For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentiviriral (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. No. 5,891, 994 and U.S. Pat. No. 6,193,981.] See, also, the HIV and SIV proteins described in D. H. Barouch et al, J. Virol., 75(5): 2462-2467 (March 2001), and R. R. Amara, et al, *Science,* 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Such combinations are discussed in more detail below.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxyirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxyirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci including pneumococci; staphylococci; and streptococci. Pathogenic gram-negative cocci include meningococcus; gonococcus. Pathogenic enteric gram-negative bacilli include enterobacteriaceae; pseudomonas, acinetobacteria and eikenella; melioidosis; salmonella; shigella; haemophilus; moraxella; *H. ducreyi* (which causes chancroid); brucella; *Franisella tularensis* (which causes tularemia); yersinia (pasteurella); streptobacillus moniliformis and spirillum; Gram-positive bacilli include listeria monocytogenes; erysipelothrix rhusiopathiae; *Corynebacterium diphtheria* (diphtheria); cholera; *B. anthracia* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox.

Examples of mycoplasma and chlamydial infections include: mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fever, all of which are currently classified as Category A agents; *Coxiella burnetti* (Q fever); *Brucella* species (brucellosis), *Burkholderia mallei* (glanders), *Ricinus communis* and its toxin (ricin toxin), *Clostridium perfringens* and its toxin (epsilon toxin), *Staphylococcus* species and their toxins (enterotoxin B), all of which are currently classified as Category B agents; and Nipan virus, multidrug-resistant tuberculosis, yellow fever, tickborne hemorrhagic fever viruses, tickborne encephalitis viruses, and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors and proteins of the invention to deliver immunogens against the variable region of the T cells elicit an immune response including CTLs to eliminate those T cells. In RA, several specific variable regions of TCRs which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In MS, several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a recombinant chimpanzee adenovirus that encodes at least one of these polypeptides will elicit an immune response that will target T cells involved in scleroderma.

C. Ad-Mediated Delivery Methods

The therapeutic levels, or levels of immunity, of the selected gene can be monitored to determine the need, if any, for boosters. Following an assessment of CD8+ T cell response, or optionally, antibody titers, in the serum, optional booster immunizations may be desired. Optionally, the C68-derived constructs of the invention may be delivered in a single administration or in various combination regimens, e.g., in combination with a regimen or course of treatment involving other active ingredients or in a prime-boost regimen. A variety of such regimens have been described in the art and may be readily selected.

For example, prime-boost regimens may involve the administration of a DNA (e.g., plasmid) based vector to prime the immune system to second, booster, administration with a traditional antigen, such as a protein or a recombinant virus carrying the sequences encoding such an antigen. See, e.g., WO 00/11140, published Mar. 2, 2000, incorporated by reference. Alternatively, an immunization regimen may involve the administration of a recombinant chimpanzee adenoviral vector of the invention to boost the immune response to a vector (either viral or DNA-based) carrying an antigen, or a protein. In still another alternative, an immunization regimen involves administration of a protein followed by booster with a vector encoding the antigen.

In one embodiment, the invention provides a method of priming and boosting an immune response to a selected antigen by delivering a plasmid DNA vector carrying said antigen, followed by boosting with a recombinant chimpanzee adenoviral vector of the invention. In one embodiment, the prime-boost regimen involves the expression of multiproteins from the prime and/or the boost vehicle. See, e.g., R. R. Amara, Science, 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered in a recombinant adenovirus construct of the invention. Still other regimens are described in WO 99/16884 and WO 01/54719.

However, the prime-boost regimens are not limited to immunization for HIV or to delivery of these antigens. For example, priming may involve delivering with a first chimp vector of the invention followed by boosting with a second chimp vector, or with a composition containing the antigen itself in protein form. In one example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming composition may be administered at various sites in the body in a dose dependent manner, which depends on the antigen to which the desired immune response is being targeted. The invention is not limited to the amount or situs of injection(s) or to the pharmaceutical carrier. Rather, the regimen may involve a priming and/or boosting step, each of which may include a single dose or dosage that is administered hourly, daily, weekly or monthly, or yearly. As an example, the mammals may receive one or two doses containing between about 10 µg to about 50 µg of plasmid in carrier. A desirable amount of a DNA composition ranges between about 1 µg to about 10,000 µg of the DNA vector. Dosages may vary from about 1 µg to 1000 µg DNA per kg of subject body weight. The amount or site of delivery is desirably selected based upon the identity and condition of the mammal.

The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes. Optionally, the priming step of this invention also includes administering with the priming composition, a suitable amount of an adjuvant, such as are defined herein.

Preferably, a boosting composition is administered about 2 to about 27 weeks after administering the priming composition to the mammalian subject. The administration of the boosting composition is accomplished using an effective amount of a boosting composition containing or capable of delivering the same antigen as administered by the priming DNA vaccine. The boosting composition may be composed of a recombinant viral vector derived from the same viral source (e.g., adenoviral sequences of the invention) or from another source. Alternatively, the "boosting composition" can be a composition containing the same antigen as encoded in the priming DNA vaccine, but in the form of a protein or peptide, which composition induces an immune response in the host. In another embodiment, the boosting composition contains a DNA sequence encoding the antigen under the control of a regulatory sequence directing its expression in a mammalian cell, e.g., vectors such as well-known bacterial or viral vectors. The primary requirements of the boosting composition are that the antigen of the composition is the same antigen, or a cross-reactive antigen, as that encoded by the priming composition.

In another embodiment, the chimpanzee adenoviral vectors and C68 targeting proteins of the invention are also well suited for use in a variety of other immunization and therapeutic regimens. Such regimens may involve delivery of C68 constructs of the invention simultaneously or sequentially with Ad constructs of different serotype capsids, regimens in which C68-derived constructs of the invention are delivered simultaneously or sequentially with non-Ad vectors, regimens in which the adenoviral vectors of the invention are delivered simultaneously or sequentially with proteins, peptides, and/or other biologically useful therapeutic or immunogenic compounds. Such uses will be readily apparent to one of skill in the art.

V. Method for Rapid Screening of Bacterial Transformants

An elegant selection method is provided by the present invention, which permits the rapid screening of constructs produced by homologous recombination or direct cloning methods. As used herein, these constructs are preferably viruses, but may include other types of vectors, such as a cosmid, episome, plasmid, or other genetic element that delivers a heterologous molecule to cells.

In one desired embodiment, the method utilizes the gene encoding green fluorescent protein (GFP), to provide a green-white selection method in which the presence of a recombinant is detected by the absence of GFP expression (i.e., the recombinants are observed as white in a green background). Alternatively, the method may utilize another suitable marker genes, including, without limitation, other fluorescent proteins and luciferase.

In one example, the method is used for production of a recombinant construct from homologous recombination of co-transected vectors into a selected host cell. As used herein, a host cell may be readily selected from an biological organism, including prokaryotic and eukaryotic cells, such as those discussed in the section related to production of a recombinant viral particle. Selection of the host cell is not a limitation of the present invention.

Suitably, each of the vectors contains the marker gene (e.g., GFP) under the control of a promoter that directs expression thereof in a host cell. Alternatively, each of the parental vectors may contain a different marker gene that allows them to be distinguished not only from the recombinant construct produced, but also from each other. Preferably, where prokaryotic GFP is utilized, it is under the control of a prokaryotic promoter such as the promoter from lacZ. However, other suitable prokaryotic or non-prokaryotic promoters may be readily selected from among the promoters described herein and known to those of skill in the art. Advantageously, the GFP protein is placed in the portion of the vectors that are eliminated during homologous recombination and thus, the GFP protein is absent from the recombinant vector produced. In this manner, the presence of unrecombined parental vectors are readily detected under a phase contrast fluorescent microscope (or other suitable detection means) as expressing the marker gene and the recombinant constructs lack expression of the marker. In the methods in which both parent vectors utilize GFP, the recombinant appears as white in a background of green.

In another example, the method is used for production of a recombinant construct involving homologous recombination, in which the host cell stably contains at least one of the parental constructs to be utilized for production of the recombinant construct. In this embodiment, the host cell can be subjected to a single transfection. In still other embodiments, the method of the invention may be utilized for triple transfections. As with the double transfection described above, the parental constructs may contain the same marker gene or may contain different marker genes.

In another example, the method of the invention is used from production of a recombinant construct by direct cloning. Suitably, in this embodiment, the marker gene present is that portion of the parent construct which is deleted during the cloning process. For example, the marker gene expression cassette (i.e., the gene, promoter, and any other necessary regulatory sequences) is engineered into the E1- or E3-region of an adenoviral vector, into which a transgene or minigene cassette will be cloned. The success of direct cloning into the target region can be readily detected by the absence of marker gene expression.

Optionally, the method of the invention can be readily assembled in the form of a kit which is available in a commercially useful format for production of recombinant constructs, e.g., recombinant adenoviruses. Typically, such kits will include plasmid backbones containing a desired viral genome containing a marker gene inserted at a point upstream or downstream of the recombination site, as appropriate, or a plasmid backbone containing the marker gene inserted at the splice site for direct cloning of a heterologous gene. Such a kit can further include appropriate culture media, host cells, a test control, instructions, and other suitable materials.

In the examples below, this method is used in production of adenoviruses. However, it will be readily understood that this method may be readily adapted for use in generating other types of adenoviral, or non-adenoviral viral vectors.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

Example 1

Creation of an E1 Deleted Vector Based on Chimpanzee Adenovirus C68 Using Green-White Selection of Recombinants A replication defective version of C68 was isolated for use in gene transfer. The classic strategy of creating a recombinant with E1 deleted, by homologous recombination in an E1 expressing cell line was pursued. The first step was creation of a plasmid containing m.u. 0 through 1.3 followed by addition of a minigene expressing enhanced green fluorescent protein (GFP) from a CMV promoter and C68 sequence spanning 9-16.7 m.u. This linearized plasmid was cotransfected into an E1 expressing cell line with Ssp I-digested C68 plasmid (SspI cuts at 3.6 m.u. leaving 4644 bp for homologous recombination). Experiments were initially conducted with 293 cells which harbor E1 from human Ad5 with the hope that this would suffice for transcomplementation. Indeed, plaques formed which represented the desired recombinant. The resulting vector was called C68-CMV-GFP.

The strategy for generating recombinants was modified to enable efficient and rapid isolation of recombinants. First, the alkaline phosphatase DNA in the initial shuttle vector was replaced with a prokaryotic GFP gene driven by the prokaryotic promoter from lacZ. This allowed efficient screening of bacterial transformations when attempting to incorporate a desired eukaryotic RNA pol II transcriptional unit into the shuttle vector. The resulting transformation can be screened for expression of GFP; white colonies are recombinants while green colonies are residual parental plasmid.

A green-white selection has been used to screen the products of cotransfection for the isolation of human Ad5 recombinants (A. R. Davis et al, *Gene Thera.*, 5:1148-1152 (1998)). In the present system, and in contrast to Davis, the initial shuttle vector was revised to include extended 3' sequences from 9 to 26 MU. This vector was cotransfected with viral DNA from the original C68-CMV-GFP isolate that had been restricted with Xba I, which cuts at MU 16.5 allowing for 9.5 Kb of overlap for homologous recombination. The resulting plaques were screened under a phase contrast fluorescent microscope for non-fluorescing isolates that represent the desired recombinants. This greatly simplified screening in comparison to the standard methods based on structure or transgene expression. Thus, this method may be readily adapted for use in generating other types of adenoviral, or non-adenoviral viral vectors.

A. Shuttle Plasmid

To construct a plasmid shuttle vector for creation of recombinant C68 virus, the plasmid pSP72 (Promega, Madison, Wis.) was modified by digestion with Bgl II followed by filling-in of the ends with Klenow enzyme (Boehringer Mannheim, Indianapolis, Ind.) and ligation with a synthetic 12 bp Pac I linker (New England Biolabs, Beverly, Mass.) to yield pSP72-Pac. A 456 bp Pac I/SnaB I fragment spanning map unit (m.u. or MU) 0-1.3 of the C68 genome was isolated from the pNEB-BamE plasmid containing BamHI E fragment of the C68 genome and cloned into Pac I and EcoR V treated pSP72-Pac to yield pSP-C68-MU 0-1.3. A minigene cassette consisting of the cytomegalovirus early promoter driving lacZ with a SV40 poly A signal was separated from pCMVβ (Clontech, Palo Alto, Calif.) as a 4.5 kb EcoRI/SalI fragment and ligated to pSP-C68-MU 0-1.3 restricted with the same set of enzymes, resulting in pSP-C68-MU 0-1.3-CMVLacZ.

For the initial step in the isolation of the 9-16.7 MU region of C68, both pGEM-3Z (Promega, Madison, Mich.) and pBS-C68-BamF were double-digested with BamHI and Sph I enzymes. Then the 293 bp fragment from pBS-C68-BamF was ligated with pGEM-3Z backbone to form pGEM-C68-MU 9-9.8. A 2.4 kb fragment including the C68 MU 9.8-16.7 was obtained from the pBS-C68 BamHB clone after XbaI digestion, filling in reaction and subsequent BamHI treatment and cloned into BamHI/SmaI double digested pGEM-C68-MU 9-9.8 to generate pGEM-C68-MU 9-16.7. The C68 9-16.7 m.u. region was isolated from pGEM-C68-MU 9-16.7 by digestion with EcoRI, filling in of the ends with Klenow enzyme (Boehringer Mannheim, Indianapolis, Ind.), ligation of a synthetic 12 bp HindIII linker (NEB) and then digestion with HindIII. This 2.7 kb fragment spanning the C68 MU 9-16.7 was cloned into the HindIII site of pSP-C68-MU 0-1.3-CMVlacZ to form the final shuttle plasmid pC68-CMV-LacZ. In addition, an 820 bp alkaline phosphatase (AP) cDNA fragment was isolated from pAdCMVALP (K. J. Fisher, et al., *J. Virol.*, 70:520-532 (1996)) and exchanged for lacZ at Not I sites of pC68-CMV-lacZ, resulting in pC68-CMV-AP.

B. Construction of Recombinant Virus

To create the E1-deleted recombinant C68-CMVEGFP vector, a pC68-CMV-EGFP shuttle plasmid was first constructed by replacing the lacZ transgene in pC68-CMV-lacZ with the enhanced green fluorescent protein (EGFP) gene. The replacement cloning process was carried out as the follows. An additional NotI restriction site was introduced into the 5' end of the EGFP coding sequence in the pEGFP-1 (Clontech, Palo Alto, Calif.) by BamHI digestion, filling in reaction and ligation of a 8 bp synthetic NotI linker (NEB). After NotI restriction of both constructs, the EGFP sequence was isolated from the modified pEGFP-1 and used to replace the lacZ gene in the pC68-CMV-lacZ. The pC68-CMVEGFP construct (3 µg) was co-transfected with Ssp I-digested C68 genomic DNA (1 µg) into 293 cells for homologous recombination as previously described (G. Gao, et al, *J. Virol*, 70:8934-8943 (1996)). Green plaques visualized by fluorescent microscopy were isolated for 2 rounds of plaque purification, expansion and purification by CsCl gradient sedimentation (G. Gao, et al, cited above).

The invention provides a uniquely modified version of the green/white selection process (A. R. Davis, et al., *Gene Thera.*, 5:1148-1152 (1998)). The present example illustrates use of this method for construction of recombinant C68 vectors. A 7.2 kb fragment spanning 9 to 36 MU was isolated from the pBSC68-BamB plasmid by treatment with AgeI and BsiwI restriction endonucleases and cloned into Asp718 and AgeI sites of pC68-CMV-AP shuttle plasmid, resulting in a new plasmid called pC68CMV-AP-MU36. A further modification was made to remove 26 to 36 m.u. from pC68CMV-AP-MU36 by Eco47III and NruI digestions. The new shuttle plasmid called pC68CMV-AP-MU26 has a shorter region for homologous recombination (i.e., 16.7-26 MU) 3' to the minigene. To make a recombinant C68 vector, alkaline phosphatase (AP) is replaced with the gene of interest. The resulting pC68CMV-Nugene-MU26 construct is co-transfected with Xba I (16.5 MU) restricted C68-CMVGFP viral DNA into 293 cells, followed by top agar overlay. The recombinant virus plaques (white) are generated through the homologous recombination in the region of 16.7-26 MU which is shared between pC68CMV-Nugene construct and C68 viral backbone; the recombinants which form white plaques are selected from green plaques of uncut C68-CMVGFP virus.

The green/white selection mechanism was also introduced to the process of cloning of the gene of interest into the pC68 shuttle plasmid. The AP gene in both pC68CMV-AP-MU36 and pC68CMV-AP-MU26 was replaced with a cassette of prokaryotic GFP gene driven by the lacZ promoter isolated from pGFPMU31 (Clontech, Palo Alto, Calif.). Thus, white colonies of bacterial transformants will contain the recombinant plasmid. This green/white selection process for bacterial colonies circumvented the need for making and characterizing large numbers of minipreped DNAs and so further enhanced the efficiency in creating recombinant C68 vectors.

Example 2

Chimpanzee C68 Virus Stock and Replication

Examples 3 through 5 which follow provide additional characterization of the chimpanzee C68. It will be appreciated by one of skill in the art that this information can be readily used in the construction of novel recombinant chimpanzee adenoviral constructs.

The C68 virus stock was obtained from ATCC (Rockville, Md.) and propagated in 293 cells (ATCC) cultured in DMEM (Sigma, St. Louis, Mo.) supplemented with 10% fetal calf serum (FCS; Sigma or Hyclone, Logan, Utah) and 1% Penicillin-Streptomycin (Sigma). Infection of 293 cells was carried out in DMEM supplemented with 2% FCS for the first 24 hours, after which FCS was added to bring the final concentration to 10%. Infected cells were harvested when 100% of the cells exhibited virus-induced cytopathic effect (CPE), collected, and concentrated by centrifugation. Cell pellets were resuspended in 10 mM Tris (pH 8.0), and lysed by 3 cycles of freezing and thawing. Virus preparations were obtained following 2 ultra centrifuge steps on cesium chloride density gradients and stocks of virus were diluted to $1 \times 10^{12}$ particles/ml in 10 mM Tris/100 mM NaCl/50% glycerol and stored at $-70°$ C.

Example 3

Cloning and Sequencing of Viral Genomic DNA

Genomic DNA was isolated from the purified virus preparation following standard methods and digested with a panel of 16 restriction enzymes following the manufacturer's recommendations. Except as noted, all restriction and modifying enzymes were obtained from Boehringer Mannheim, Indianapolis, Ind. Genomic DNA was digested with BamHI, PstI, SalI, HindIII or XbaI and the fragments were subcloned into plasmids (K. L. Berkner and P. A. Sharp, *Nucl. Acids Res.*, 11:6003-20 (1983)). After deproteination, synthetic 10 bp PacI linkers (New England Biolabs, Beverly, Mass.) were double digested with PacI and BamHI, or PstI.

The PstI, BamHI and HindIII clones generated from C68 are illustrated in FIG. 1, parts C, D and E, respectively. The fragments indicated by the shaded boxes were not cloned, but the sequence of the entire genome has been determined through sequencing overlapping clones and viral DNA directly (unshaded boxes). The cloned fragments and insert sizes are described in Table 1. In the following table, pBS=pBluescript SK+ clone; pNEB=pNEB 193 clone; pBR=pBR322 clone; No prefix=fragment not cloned.

TABLE 1

C68 plasmid clones and insert sizes

| Construct Name | Insert Size (base pairs) | Fragment 5' End | Fragment 3' End | 5' End Map Unit | 3' End Map Unit |
|---|---|---|---|---|---|
| Pst-I Fragments | | | | | |
| C68-Pst-A | 6768 | 24784 | 31551 | 67.9% | 86.4% |
| pBS:C68-Pst-B | 6713 | 4838 | 11550 | 13.2% | 31.6% |
| pBS:C68-Pst-C | 5228 | 14811 | 20038 | 40.6% | 54.9% |
| pBS:C68-Pst-D | 2739 | 12072 | 14810 | 33.1% | 40.6% |
| pBS:C68-Pst-E | 2647 | 20039 | 22685 | 54.9% | 32.1% |
| pBS:C68-Pst-F | 1951 | 32046 | 33996 | 87.8% | 93.1% |
| pNEB:C68-Pst-G | 1874 | 1 | 1874 | 0.0% | 5.1% |
| pBS:C68-Pst-H | 1690 | 23094 | 24783 | 63.2% | 67.9% |
| pBS:C68-Pst-I | 1343 | 33997 | 35339 | 93.1% | 96.8% |
| pNEB:C68-Pst-J | 1180 | 35340 | 36519 | 96.8% | 100.0% |
| pBS:C68-Pst-K | 1111 | 2763 | 3873 | 7.6% | 10.6% |
| pBS:C68-Pst-L | 964 | 3874 | 4837 | 10.6% | 13.2% |
| pBS:C68-Pst-M | 888 | 1875 | 2762 | 5.1% | 7.6% |
| pBS:C68-Pst-N | 408 | 22686 | 23093 | 62.1% | 63.2% |
| C68-Pst-O | 380 | 31666 | 32045 | 86.7% | 87.7% |
| pBS:C68-Pst-P | 285 | 11551 | 11835 | 31.6% | 32.4% |
| C68-Pst-Q | 236 | 11836 | 12071 | 32.4% | 33.1% |
| pBS:C68-Pst-R | 114 | 31552 | 31665 | 86.4% | 86.7% |
| BamHI Fragments | | | | | |
| C68-Bam-A | 16684 | 19836 | 36519 | 54.3% | 100.0% |
| pBS:C68-Bam-B | 8858 | 3582 | 12439 | 9.8% | 34.1% |
| pBS:C68-Bam-C | 4410 | 12440 | 16849 | 34.1% | 46.1% |
| pBS:C68-Bam-D | 2986 | 16850 | 19835 | 46.1% | 54.3% |
| pNEB:C68-Bam-E | 2041 | 1 | 2041 | 0.0% | 5.6% |
| pBS:C68-Bam-F | 1540 | 2042 | 3581 | 5.6% | 9.8% |
| HindIII Fragments | | | | | |
| pBR:C68-Hind-B | 9150 | 23471 | 32620 | 64.3% | 89.3% |

Chimpanzee adenovirus, C68, was obtained from ATCC and propagated in human 293 cells. Viral genomic DNA was isolated from purified virions using established procedures (A. R. Davis, et al., *Gene Thera.*, 5:1148-1152 (1998)) and digested with a panel of restriction enzymes; the data were consistent with previous studies (data not shown) (G. R. Kitchingman, *Gene*, 20:205-210 (1982); Q. L1 and G. Wadell, *Arch Virol.* 101:65-77 (1998); R. Wigand, et al., *Intervirology.* 30:1-9 (1989)). Restriction fragments spanning the entire genome of C68 were subcloned into plasmids. A schematic drawing of the C68 genome is shown in FIG. 1A, and the Pst-I, BamHI and HindIII fragments that were cloned into plasmid vectors are indicated by the unshaded boxes, in FIGS. 1B, 1C, and 1D, respectively. The cloned fragments, fragment sizes and genomic position are also listed in Table 1. Both plasmid clones and genomic DNA were used as templates for sequencing. The genome was sequenced by primer walking in both directions and each base was included in an average of approximately four reactions.

The C68 genome is 36521 bp in length [see, U.S. Pat. No. 6,083,716]. Preliminary comparison with GenBank sequences indicated varying degrees of similarity with other human and animal adenoviruses along the entire length of the viral genome. Regions with homology to all of the previously described adenoviral genetic units, early regions 1-4 and the major late genes, were found in the C68 genome (FIG. 1A). DNA homology between C68 and the human adenoviruses that have been completely sequenced, Ad2 (NC001405), Ad5 (NC001405), Ad12 (NC001460), Ad17 (NC002067) and Ad40 (NC01464), was used to order the clones. The open reading frames (ORF) were determined and the genes were identified based on homology to other human adenoviruses. All of the major adenoviral early and late genes are present in C68. The inverted terminal repeats (ITR's) are 130 bp in length.

Example 4

Analysis of C68 Sequence

The complete nucleotide sequence of every member of the Mastadenovirus genus accessible from GenBank, including isolates from different species, were screened for identity to C68. The Ad4 minigenome was assembled from the following GenBank sequences: Left-hand ITR (J01964); E1A region (M14918); DNA pol and pTP (X74508, 74672); VA RNA-I, II (U10682); 52, 55K (U52535); pVII (U70921); hexon (X84646); endoprotease (M16692); DNA-binding protein (M12407); fiber (X76547); right-hand ITR (J01965). The Ad7 composite genome was created from the following sequence data: Mu 3-21 (X03000); VA RNA-I, II, pTP & 52, 55K (U52574); penton (AD001675); pVI, hexon and endoprotease (AF065065); DNA-binding protein (K02530); E3 and fiber region (AF104384); right-hand ITR (V00037).

The amino acid sequence alignment was generated with Clustal X, edited with Jalview (available on the world wide web at ebi.ac.uk/~michele/jalview), and analyzed with Boxshade (available on the world wide web at ch.embnet.org/software/BOX_form.html). Publicly available hexon protein sequences from all human adenovirus serotypes were initially aligned to identify the set showing the highest homology to C68.

The nucleotide sequence and predicted amino acid sequences of all significant open reading frames in the C68 genome were compared to known DNA and protein sequences. The nucleotide sequence of C68 was compared to sequences of Ad 2, 4, 5, 7, 12, 17 and 40. In agreement with previous restriction analysis (Kitchingman, cited above) C68 is most similar to human Ad4 (subgroup E).

The E1A region of C68 extends from the TATA box at nt 480 to the poly A addition site at 1521. The consensus splice donor and acceptor sites are in the analogous position of the human Ad counterparts, and the 28.2K and 24.8K proteins are similar in size to the human Ad proteins. The ORF for the smallest E1A protein of C68 is predicted to encode 101 residues as opposed to approximately 60 amino acids for other adenoviruses. There is a TTA codon at residue 60 for C68 where other adenoviruses often have a TGA stop codon. The first 60 residues of C68 E1A R protein have 85% identity to the Ad4 homolog.

The C68 genome encodes genes for the four E1B proteins, 20.5K, 54.7K, 10.1K and 18.5K as well as pIX. All five C68 encoded proteins are similar in size to that of other Ad E1B and pIX proteins. The Ad4 homolog of the E1B 21K protein has only 142 amino acids, where C68 has 186 residues and other human adenoviruses have 163-178 residues. The C68 and Ad4 proteins share 95% identity over the first 134 aa, then the similarity ends and the Ad4 protein terminates at 142 amino acids.

The C68 genome encodes homologs of the E2A 55K DNA binding protein and the Iva2 maturation protein, as well as the E2B terminal protein and the DNA polymerase. All of the E2 region proteins are similar in size to their human Ad counterparts, and the E2B proteins are particularly well conserved. The C68 E2B 123.6K DNA polymerase is predicted to be 1124 residues, while Ad4 is predicted to have 1193 although the other human adenoviruses have smaller polymerases. Residues 1-71 of the Ad4 polymerase have no similarity to any other Ad polymerase, and it is possible that this protein actually initiates at an internal ATG codon. From amino acids 72-1193, Ad4 and C68 polymerases have 96% amino acid identity.

The E3 regions of human adenoviruses sequenced so far exhibit considerable sequence and coding capacity variability. Ad40 has five E3 region genes, Ad12 has six, C68 and Ad5 have seven, Ad38 has eight and Ad3 as well as Ad7 (subgroup B human adenoviruses) have nine putative E3 region genes. The Ad4 E3 region has not yet been sequenced. In comparison with the E3 region of Ad35, all 7 E3 gene homologs were identified in the C68 genome (C. F. Basler and M. S. Horwitz, *Virology*, 215: 165-177 (1996)).

The C68 E4 region has 6 ORFs and each is homologous to proteins in the human Ad5, 12 and 40 E4 region. The E4 nomenclature is confusing because the ORF2 homologs of C68, Ad12 and Ad40 are approximately 130 residues, while in Ad5 there are two ORFs encoding proteins of 64 and 67 residues with homology, respectively, to the amino and carboxy terminal ends of the larger ORF2 proteins. ORF5 has been omitted in our nomenclature because the $5^{th}$ ORF in the E4 region is homologous to the widely studied ORF6 protein of human Ad5.

The major late promoter and the tri-partite leader sequences of the C68 genome were located. ORFs with the potential to encode the 15 major late proteins were located. All of the C68 late proteins are similar in size to their human Ad counterparts. The percent amino acid identity between chimpanzee and human Ad late proteins varies considerably. The C68 fiber protein is predicted to have 90% amino acid identity with the Ad4 protein, but much less similarity to the other human Ad fiber proteins. The CAR binding site in the fiber knob is present in C68.

Example 5

Virus Neutralizing Antibody Assays

Several studies were performed to determine if there is cross-reactivity between type specific antisera of C68 and human adenovirus. The neutralizing activity of sera was tested as follows. Panels of sera from normal human subjects (N=50), rhesus monkeys (N=52) and chimpanzees (N=20) were evaluated for neutralizing antibodies against Ad5 and C68 based vectors using 293 cells as an indicator cell line. Sera collected from individual humans, rhesus monkeys, or chimpanzees were inactivated at 56 C for 30 minutes. A serial dilution of each sample (1:10, 1:20, 1:40, 1:80, 1:160, 1:320 in 100 µl of DMEM containing 10% FCS) was added to equal amounts of H5.010CMVEGFP (1000 PFU/well) or C68CMVEGFP virus and incubated at 4 C for two hrs. One hundred and fifty microliters of the mixture were transferred onto 2×10 293 cells in 96 well flat bottom plates. Control wells were infected with equal amounts of virus (without addition of serum). Samples were incubated at 37 C in 5% $CO_2$ for 48 hrs and examined under a fluorescent microscope. Sample dilutions that showed >50% reduction of green-fluorescent foci as compared to infected controls were scored positive for neutralizing antibodies.

As expected, approximately 35% of normal human subjects demonstrated neutralizing antibody against Ad5, a frequency much higher than observed in sera of rhesus monkeys and chimpanzee. Neutralizing antibody to C68 was observed in 80% of chimpanzee and only 2% of normal human subjects or rhesus monkeys. Titers of neutralizing antibodies in the non-target species were generally low.

To further evaluate cross-reactivity of C68 with human adenovirus vectors, mice were immunized with $2 \times 10^7$ plaque forming units (pfu) of Ad 2, 4, 5, 7 and 12 as well as C68. Sera were harvested 2 weeks later and tested for antibodies that neutralized either Ad5 or C68 vectors. Neutralizing antibody to Ad5 vector was only detected in animals immunized with Ad5. Importantly, the only animals with neutralizing antibody to C68 vector were those immunized with C68 vector; none of the human serotypes tested, including Ad4, generated antibodies in mice that neutralized C68 in vitro.

Important to the utility of C68 vector in human trials is the absence of neutralizing antibody in the human population. In our study, a screen of 50 normal human subjects failed to detect any significant neutralizing antibodies (>1:10) using the same assay that showed neutralizing antibodies in >50% of chimpanzees. Furthermore, sera of mice immunized with multiple human Ad serotypes including Ad4, did not neutralize infection with C68.

Example 6

Structural Analysis of Hexon Proteins

The absence of neutralizing antibodies between C68 and human serotypes compelled us to more carefully evaluate structural differences in the regions of hexon presumed to harbor type specific epitopes. Previous studies have suggested that these epitopes are located within the 7 hypervariable regions of hexon determined by Crawford-Miksza and Schnurr (*J. Virol*, 70:1836-1844 (1996)). A comparison of the amino acid sequences of hexon proteins between C68 and several human adenoviruses is shown in FIG. 3. Indeed, C68 is substantially dissimilar in significant regions of these hypervariable sequences.

Example 7

Construction of C68-Derived Capsid Containing a Human Fiber Gene

To generate a C68-derived vector with an altered tropism, the chimeric fiber gene construct containing the Ad5 fiber knob fused to the C68 tail and shaft is incorporated into a plasmid carrying the C68 genome. For the precise replacement of the wild-type C68 fiber gene, a plasmid carrying the green fluorescent protein driven by a CMV promoter is used for modification of C68 fiber. The resulting transfer vector contains a CMV promoter driven green fluorescent protein (GFP) expression cassette inserted into the E3 region, the chimeric C68/Ad5 fiber gene, and E4. This transfer vector was used for incorporation of GFP cassette and modified fiber gene into the backbone of an E3 deleted C68 infectious plasmid via homologous recombination in *E. coli*. The viral genome was released from the plasmid by PacI digestion and used to transfect 293 cells. The chimeric C68-derived virus is produced about 3 weeks following transfection using techniques described herein. Similar techniques can be readily utilized to construct other C68-derived capsids.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

---

What is claimed is:

1. A recombinant virus comprising an adenovirus capsid, which capsid comprises one or more fragments of the C68 fiber of SEQ ID NO: 27 fused to a heterologous adenovirus capsid protein, and the capsid further comprises a modified adenovirus C68 penton protein fragment selected from the group consisting of: SEQ ID NO: 12 having a 50 amino acid N-terminal or C-terminal truncation; SEQ ID NO: 12 having a 100 amino acid N-terminal or C-terminal truncation; SEQ ID NO: 12 having a 150 amino acid N-terminal or C-terminal truncation; and SEQ ID NO: 12 having a 200 amino acid N-terminal or C-terminal truncation, said one or more fragments of the C68 fiber selected from the group consisting of: SEQ ID NO: 27 having a 50 amino acid N-terminal or C-terminal truncation; SEQ ID NO: 27 having a 100 amino acid N-terminal or C-terminal truncation; SEQ ID NO: 27 having a 150 amino acid N-terminal or C-terminal truncation; SEQ ID NO: 27 having a 200 amino acid N-terminal or C-terminal truncation, and a fragment of the fiber protein having the sequence of amino acids 247 to 425 of SEQ ID NO:27 wherein said capsid encapsidates a molecule for delivery to a target cell, wherein the molecule comprises an adenovirus 5' inverted terminal repeat sequence (ITRs), a minigene, and an adenovirus 3' ITR.

2. The recombinant adenovirus according to claim 1, wherein the adenovirus ITRs are from a serotype heterologous to C68.

3. A pharmaceutical composition comprising a physiologically acceptable carrier and a recombinant virus according to claim 1.

4. A recombinant virus comprising an adenovirus capsid, which capsid comprises one or more fragments of the C68 fiber of SEQ ID NO: 27 fused to a heterologous adenovirus capsid protein from a non-chimpanzee simian adenovirus, said capsid encapsidating a molecule for delivery to a target cell, wherein the molecule comprises an adenovirus 5' inverted terminal repeat sequence (ITRs), a minigene, and an adenovirus 3' ITR, said fragment selected from the group consisting of: SEQ ID NO: 27 having a 50 amino acid N-terminal or C-terminal truncation; SEQ ID NO: 27 having a 100 amino acid N-terminal or C-terminal truncation; SEQ ID NO: 27 having a 150 amino acid N-terminal or C-terminal truncation; SEQ ID NO: 27 having a 200 amino acid N-terminal or C-terminal truncation, and a fragment of the fiber protein having the sequence of amino acids 247 to 425 of SEQ ID NO:27.

5. A pharmaceutical composition comprising a physiologically acceptable carrier and a recombinant virus according to claim 4.

* * * * *

SEQUENCE LISTING

```
<160> NUMBER OF SEQ ID NOS: 41

<210> SEQ ID NO 1
<211> LENGTH: 101
<212> TYPE: PRT
<213> ORGANISM: chimpanzee C68 adenovirus protein

<400> SEQUENCE: 1

Met Arg His Leu Arg Asp Leu Pro Asp Glu Lys Ile Ile Ile Ala Ser
1               5                   10                  15

Gly Asn Glu Ile Leu Glu Leu Val Val Pro Ser Leu Thr Gln Met Met
            20                  25                  30

Arg Pro Pro Leu Gln Ser Pro Leu Arg His Pro Gln Lys Leu Ala His
        35                  40                  45

Leu His Leu Arg Ile Leu Leu Asp Gln Phe Leu Leu Glu Pro Leu Gly
    50                  55                  60

Gly Glu Gln Leu Trp Asn Val Trp Met Thr Cys Tyr Arg Val Gly Leu
65                  70                  75                  80

Asn Leu Trp Thr Cys Val Pro Gly Asn Ala Pro Gly Thr Lys Cys His
                85                  90                  95

Thr Cys Val Phe Thr
            100

<210> SEQ ID NO 2
<211> LENGTH: 257
<212> TYPE: PRT
<213> ORGANISM: chimpanzee C68 adenovirus protein

<400> SEQUENCE: 2

Met Arg His Leu Arg Asp Leu Pro Asp Glu Lys Ile Ile Ile Ala Ser
1               5                   10                  15

Gly Asn Glu Ile Leu Glu Leu Val Val Asn Ala Met Met Gly Asp Asp
            20                  25                  30

Pro Pro Glu Pro Pro Thr Pro Phe Glu Thr Pro Ser Leu His Asp Leu
        35                  40                  45

Tyr Asp Leu Glu Val Asp Val Pro Glu Asp Pro Asn Glu Glu Ala
    50                  55                  60

Val Asn Asp Phe Phe Ser Asp Ala Ala Leu Leu Ala Ala Glu Glu Ala
65                  70                  75                  80

Ser Ser Ser Ser Ser Asp Ser Asp Ser Ser Leu His Thr Pro Arg Pro
                85                  90                  95
```

```
Gly Arg Gly Glu Lys Lys Ile Pro Glu Leu Lys Gly Glu Glu Met Asp
            100                 105                 110

Leu Arg Cys Tyr Glu Glu Cys Leu Pro Pro Ser Asp Asp Glu Asp Glu
            115                 120                 125

Gln Ala Ile Gln Asn Ala Ala Ser Gln Gly Val Gln Ala Ala Ser Glu
            130                 135                 140

Ser Phe Ala Leu Asp Cys Pro Pro Leu Pro Gly His Gly Cys Lys Ser
145                 150                 155                 160

Cys Glu Phe His Arg Met Asn Thr Gly Asp Lys Ala Val Leu Cys Ala
                    165                 170                 175

Leu Cys Tyr Met Arg Ala Tyr Asn His Cys Val Tyr Ser Pro Val Ser
            180                 185                 190

Asp Ala Asp Asp Glu Thr Pro Thr Thr Lys Ser Thr Ser Ser Pro Pro
            195                 200                 205

Glu Ile Gly Thr Ser Pro Pro Glu Asn Ile Val Arg Pro Val Pro Val
            210                 215                 220

Arg Ala Thr Gly Arg Arg Ala Ala Val Glu Cys Leu Asp Asp Leu Leu
225                 230                 235                 240

Gln Gly Gly Val Glu Pro Leu Asp Leu Cys Thr Arg Lys Arg Pro Arg
                    245                 250                 255

His

<210> SEQ ID NO 3
<211> LENGTH: 226
<212> TYPE: PRT
<213> ORGANISM: chimpanzee C68 adenovirus protein

<400> SEQUENCE: 3

Met Arg His Leu Arg Asp Leu Pro Asp Glu Lys Ile Ile Ile Ala Ser
1               5                   10                  15

Gly Asn Glu Ile Leu Glu Leu Val Val Asn Ala Met Met Gly Asp Asp
            20                  25                  30

Pro Pro Glu Pro Pro Thr Pro Phe Glu Thr Pro Ser Leu His Asp Leu
        35                  40                  45

Tyr Asp Leu Glu Val Asp Val Pro Glu Asp Asp Pro Asn Glu Glu Ala
    50                  55                  60

Val Asn Asp Phe Phe Ser Asp Ala Ala Leu Leu Ala Ala Glu Glu Ala
65                  70                  75                  80

Ser Ser Ser Ser Ser Asp Ser Asp Ser Ser Leu His Thr Pro Arg Pro
                    85                  90                  95

Gly Arg Gly Glu Lys Lys Ile Pro Glu Leu Lys Gly Glu Glu Met Asp
            100                 105                 110

Leu Arg Cys Tyr Glu Glu Cys Leu Pro Pro Ser Asp Asp Glu Asp Glu
            115                 120                 125

Gln Ala Ile Gln Asn Ala Ala Ser Gln Gly Val Gln Ala Ala Ser Glu
            130                 135                 140

Ser Phe Ala Leu Asp Cys Pro Pro Leu Pro Gly His Gly Cys Pro Val
145                 150                 155                 160

Ser Asp Ala Asp Asp Glu Thr Pro Thr Thr Lys Ser Thr Ser Ser Pro
                    165                 170                 175

Pro Glu Ile Gly Thr Ser Pro Pro Glu Asn Ile Val Arg Pro Val Pro
            180                 185                 190

Val Arg Ala Thr Gly Arg Arg Ala Ala Val Glu Cys Leu Asp Asp Leu
            195                 200                 205
```

Leu Gln Gly Gly Val Glu Pro Leu Asp Leu Cys Thr Arg Lys Arg Pro
    210                 215                 220

Arg His
225

<210> SEQ ID NO 4
<211> LENGTH: 186
<212> TYPE: PRT
<213> ORGANISM: chimpanzee C68 adenovirus protein

<400> SEQUENCE: 4

Met Glu Ile Trp Thr Val Leu Glu Asp Phe His Lys Thr Arg Gln Leu
1               5                   10                  15

Leu Glu Asn Ala Ser Asn Gly Val Ser Tyr Leu Trp Arg Phe Cys Phe
            20                  25                  30

Gly Gly Asp Leu Ala Arg Leu Val Tyr Arg Ala Lys Gln Asp Tyr Ser
        35                  40                  45

Glu Gln Phe Glu Val Ile Leu Arg Glu Cys Ser Gly Leu Phe Asp Ala
    50                  55                  60

Leu Asn Leu Gly His Gln Ser His Phe Asn Gln Arg Ile Ser Arg Ala
65                  70                  75                  80

Leu Asp Phe Thr Thr Pro Gly Arg Thr Thr Ala Ala Val Ala Phe Phe
                85                  90                  95

Ala Phe Ile Leu Asp Lys Trp Ser Gln Glu Thr His Phe Ser Arg Asp
            100                 105                 110

Tyr Gln Leu Asp Phe Leu Ala Val Ala Leu Trp Arg Thr Trp Lys Cys
        115                 120                 125

Gln Arg Leu Asn Ala Ile Ser Gly Tyr Leu Pro Val Gln Pro Leu Asp
    130                 135                 140

Thr Leu Arg Ile Leu Asn Leu Gln Glu Ser Pro Arg Ala Arg Gln Arg
145                 150                 155                 160

Arg Gln Gln Gln Gln Glu Glu Asp Gln Glu Glu Asn Pro Arg Ala
                165                 170                 175

Gly Leu Asp Pro Pro Ala Glu Glu Glu
            180                 185

<210> SEQ ID NO 5
<211> LENGTH: 498
<212> TYPE: PRT
<213> ORGANISM: chimpanzee C68 adenovirus protein

<400> SEQUENCE: 5

Met Glu Ser Arg Asn Pro Phe Gln Gln Gly Leu Pro Ala Gly Phe Leu
1               5                   10                  15

Ser Ser Ser Phe Val Glu Asn Met Glu Val Pro Ala Pro Glu Cys Asn
            20                  25                  30

Leu Arg Leu Leu Ala Gly Thr Ala Ala Arg His Ser Glu Asp Pro Glu
        35                  40                  45

Ser Pro Gly Glu Ser Gln Gly Thr Pro Thr Ser Pro Ala Ala Ala Ala
    50                  55                  60

Gly Gly Gly Ser Arg Arg Glu Pro Glu Ser Arg Pro Gly Pro Ser Gly
65                  70                  75                  80

Gly Gly Gly Gly Val Ala Asp Leu Phe Pro Glu Leu Arg Arg Val Leu
                85                  90                  95

Thr Arg Ser Ser Ser Gly Arg Glu Arg Gly Ile Lys Arg Glu Arg His
            100                 105                 110

```
Asp Glu Thr Asn His Arg Thr Glu Leu Thr Val Gly Leu Met Ser Arg
            115                 120                 125

Lys Arg Pro Glu Thr Val Trp Trp His Glu Val Gln Ser Thr Gly Thr
130                 135                 140

Asp Glu Val Ser Val Met His Glu Arg Phe Ser Leu Glu Gln Val Lys
145                 150                 155                 160

Thr Cys Trp Leu Glu Pro Glu Asp Asp Trp Glu Val Ala Ile Arg Asn
                165                 170                 175

Tyr Ala Lys Leu Ala Leu Arg Pro Asp Lys Lys Tyr Lys Ile Thr Lys
            180                 185                 190

Leu Ile Asn Ile Arg Asn Ala Cys Tyr Ile Ser Gly Asn Gly Ala Glu
            195                 200                 205

Val Glu Ile Cys Leu Gln Glu Arg Val Ala Phe Arg Cys Cys Met Met
            210                 215                 220

Asn Met Tyr Pro Gly Val Val Gly Met Asp Gly Val Thr Phe Met Asn
225                 230                 235                 240

Met Arg Phe Arg Gly Asp Gly Tyr Asn Gly Thr Val Phe Met Ala Asn
                245                 250                 255

Thr Lys Leu Thr Val His Gly Cys Ser Phe Phe Gly Phe Asn Asn Thr
            260                 265                 270

Cys Ile Glu Ala Trp Gly Gln Val Gly Val Arg Gly Cys Ser Phe Ser
            275                 280                 285

Ala Asn Trp Met Gly Val Val Gly Arg Thr Lys Ser Met Leu Ser Val
            290                 295                 300

Lys Lys Cys Leu Phe Glu Arg Cys His Leu Gly Val Met Ser Glu Gly
305                 310                 315                 320

Glu Ala Arg Ile Arg His Cys Ala Ser Thr Glu Thr Gly Cys Phe Val
                325                 330                 335

Leu Cys Lys Gly Asn Ala Lys Ile Lys His Asn Met Ile Cys Gly Ala
            340                 345                 350

Ser Asp Glu Arg Gly Tyr Gln Met Leu Thr Cys Ala Gly Gly Asn Ser
            355                 360                 365

His Met Leu Ala Thr Val His Val Ala Ser His Ala Arg Lys Pro Trp
            370                 375                 380

Pro Glu Phe Glu His Asn Val Met Thr Arg Cys Asn Met His Leu Gly
385                 390                 395                 400

Ser Arg Arg Gly Met Phe Met Pro Tyr Gln Cys Asn Leu Asn Tyr Val
                405                 410                 415

Lys Val Leu Leu Glu Pro Asp Ala Met Ser Arg Val Ser Leu Thr Gly
            420                 425                 430

Val Phe Asp Met Asn Val Glu Val Trp Lys Ile Leu Arg Tyr Asp Glu
            435                 440                 445

Ser Lys Thr Arg Cys Arg Ala Cys Glu Cys Gly Gly Lys His Ala Arg
450                 455                 460

Phe Gln Pro Val Cys Val Asp Val Thr Glu Asp Leu Arg Pro Asp His
465                 470                 475                 480

Leu Val Leu Pro Cys Thr Gly Thr Glu Phe Gly Ser Ser Gly Glu Glu
                485                 490                 495

Ser Asp

<210> SEQ ID NO 6
<211> LENGTH: 169
<212> TYPE: PRT
<213> ORGANISM: chimpanzee C68 adenovirus protein
```

```
<400> SEQUENCE: 6

Met Glu Ser Arg Asn Pro Phe Gln Gln Gly Leu Pro Ala Gly Phe Leu
1               5                   10                  15

Ser Ser Ser Phe Val Glu Asn Met Glu Val Pro Ala Pro Glu Cys Asn
            20                  25                  30

Leu Arg Leu Leu Ala Gly Thr Ala Ala Arg His Ser Glu Asp Pro Glu
        35                  40                  45

Ser Pro Gly Glu Ser Gln Gly Thr Pro Thr Ser Pro Ala Ala Ala Ala
    50                  55                  60

Gly Gly Gly Ser Arg Arg Glu Pro Glu Ser Arg Pro Gly Pro Ser Gly
65                  70                  75                  80

Gly Gly Gly Gly Val Ala Asp Leu Phe Pro Glu Leu Arg Arg Val Leu
                85                  90                  95

Thr Arg Val Ser Leu Thr Gly Val Phe Asp Met Asn Val Glu Val Trp
            100                 105                 110

Lys Ile Leu Arg Tyr Asp Glu Ser Lys Thr Arg Cys Arg Ala Cys Glu
        115                 120                 125

Cys Gly Gly Lys His Ala Arg Phe Gln Pro Val Cys Val Asp Val Thr
    130                 135                 140

Glu Asp Leu Arg Pro Asp His Leu Val Leu Pro Cys Thr Gly Thr Glu
145                 150                 155                 160

Phe Gly Ser Ser Gly Glu Glu Ser Asp
                165

<210> SEQ ID NO 7
<211> LENGTH: 93
<212> TYPE: PRT
<213> ORGANISM: chimpanzee C68 adenovirus protein

<400> SEQUENCE: 7

Met Glu Ser Arg Asn Pro Phe Gln Gln Gly Leu Pro Ala Gly Phe Leu
1               5                   10                  15

Ser Ser Ser Phe Val Glu Asn Met Glu Val Pro Ala Pro Glu Cys Asn
            20                  25                  30

Leu Arg Leu Leu Ala Gly Thr Ala Ala Arg His Ser Glu Asp Pro Glu
        35                  40                  45

Ser Pro Gly Glu Ser Gln Gly Thr Pro Thr Ser Pro Ala Ala Ala Ala
    50                  55                  60

Gly Gly Gly Ser Arg Arg Glu Pro Glu Ser Arg Pro Gly Pro Ser Gly
65                  70                  75                  80

Gly Gly Gly Gly Val Ala Asp Leu Pro Cys Val Trp Met
                85                  90

<210> SEQ ID NO 8
<211> LENGTH: 142
<212> TYPE: PRT
<213> ORGANISM: chimpanzee C68 adenovirus protein

<400> SEQUENCE: 8

Met Ser Gly Ser Gly Ser Phe Glu Gly Gly Val Phe Ser Pro Tyr Leu
1               5                   10                  15

Thr Gly Arg Leu Pro Ser Trp Ala Gly Val Arg Gln Asn Val Met Gly
            20                  25                  30

Ser Thr Val Asp Gly Arg Pro Val Gln Pro Ala Asn Ser Ser Thr Leu
        35                  40                  45
```

```
Thr Tyr Ala Thr Leu Ser Ser Ser Leu Asp Ala Ala Ala Ala
         50                  55                  60

Ala Ala Ala Ser Ala Ala Ser Ala Val Arg Gly Met Ala Met Gly Ala
 65                  70                  75                  80

Gly Tyr Tyr Gly Thr Leu Val Ala Asn Ser Ser Thr Asn Asn Pro
                 85                  90                  95

Ala Ser Leu Asn Glu Glu Lys Leu Leu Leu Met Ala Gln Leu Glu
            100                 105                 110

Ala Leu Thr Gln Arg Leu Gly Glu Leu Thr Gln Gln Val Ala Gln Leu
            115                 120                 125

Gln Glu Gln Thr Arg Ala Ala Val Ala Thr Val Lys Ser Lys
            130                 135                 140
```

<210> SEQ ID NO 9
<211> LENGTH: 448
<212> TYPE: PRT
<213> ORGANISM: chimpanzee C68 adenovirus protein

<400> SEQUENCE: 9

```
Met Glu Thr Lys Gly Arg Arg Ser Gly Ala Val Phe Asp Gln Pro Asp
 1               5                  10                  15

Glu Pro Glu Ala His Pro Arg Lys Arg Pro Ala Arg Arg Ala Pro Leu
                20                  25                  30

His Arg Asp Gly Asp His Pro Asp Ala Asp Ala Ala Thr Leu Glu Gly
            35                  40                  45

Pro Asp Pro Gly Cys Ala Gly Arg Pro Ser Ser Gly Ala Ile Leu Pro
 50                  55                  60

Gln Pro Ser Gln Pro Ala Lys Arg Gly Gly Leu Leu Asp Arg Asp Ala
 65                  70                  75                  80

Val Glu His Ile Thr Glu Leu Trp Asp Arg Leu Glu Leu Leu Gln Gln
                 85                  90                  95

Thr Leu Ser Lys Met Pro Met Ala Asp Gly Leu Lys Pro Leu Lys Asn
            100                 105                 110

Phe Ala Ser Leu Gln Glu Leu Leu Ser Leu Gly Gly Glu Arg Leu Leu
        115                 120                 125

Ala Glu Leu Val Arg Glu Asn Met His Val Arg Glu Met Met Asn Glu
    130                 135                 140

Val Ala Pro Leu Leu Arg Glu Asp Gly Ser Cys Leu Ser Leu Asn Tyr
145                 150                 155                 160

His Leu Gln Pro Val Ile Gly Val Ile Tyr Gly Pro Thr Gly Cys Gly
                165                 170                 175

Lys Ser Gln Leu Leu Arg Asn Leu Leu Ser Ala Gln Leu Ile Ser Pro
            180                 185                 190

Ala Pro Glu Thr Val Phe Phe Ile Ala Pro Gln Val Asp Met Ile Pro
        195                 200                 205

Pro Ser Glu Leu Lys Ala Trp Glu Met Gln Ile Cys Glu Gly Asn Tyr
    210                 215                 220

Ala Pro Gly Ile Glu Gly Thr Phe Val Pro Gln Ser Gly Thr Leu Arg
225                 230                 235                 240

Pro Lys Phe Ile Lys Met Ala Tyr Asp Asp Leu Thr Gln Asp His Asn
                245                 250                 255

Tyr Asp Val Ser Asp Pro Arg Asn Val Phe Ala Gln Ala Ala His
            260                 265                 270

Gly Pro Ile Ala Ile Ile Met Asp Glu Cys Met Glu Asn Leu Gly Gly
        275                 280                 285
```

```
His Lys Gly Val Ala Lys Phe Phe His Ala Phe Pro Ser Lys Leu His
        290                 295                 300

Asp Lys Phe Pro Lys Cys Thr Gly Tyr Thr Val Leu Val Leu His
305                 310                 315                 320

Asn Met Asn Pro Arg Arg Asp Leu Gly Gly Asn Ile Ala Asn Leu Lys
                325                 330                 335

Ile Gln Ala Lys Met His Leu Ile Ser Pro Arg Met His Pro Ser Gln
            340                 345                 350

Leu Asn Arg Phe Val Asn Thr Tyr Thr Lys Gly Leu Pro Val Ala Ile
        355                 360                 365

Ser Leu Leu Lys Asp Ile Val Gln His Ala Leu Arg Pro Cys
370                 375                 380

Tyr Asp Trp Val Ile Tyr Asn Thr Thr Pro Glu His Glu Ala Leu Gln
385                 390                 395                 400

Trp Ser Tyr Leu His Pro Arg Asp Gly Leu Met Pro Met Tyr Leu Asn
                405                 410                 415

Ile Gln Ala His Leu Tyr Arg Val Leu Glu Lys Ile His Arg Val Leu
            420                 425                 430

Asn Asp Arg Asp Arg Trp Ser Arg Ala Tyr Arg Ala Arg Lys Ile Lys
        435                 440                 445

<210> SEQ ID NO 10
<211> LENGTH: 200
<212> TYPE: PRT
<213> ORGANISM: chimpanzee C68 adenovirus protein
<220> FEATURE:
<221> NAME/KEY: MISC_FEATURE
<222> LOCATION: (137)..(137)
<223> OTHER INFORMATION: xaa can be any amino acid
<220> FEATURE:
<221> NAME/KEY: MISC_FEATURE
<222> LOCATION: (155)..(155)
<223> OTHER INFORMATION: xaa can be any amino acid

<400> SEQUENCE: 10

Met Arg Ala Asp Gly Glu Glu Leu Asp Leu Leu Pro Pro Ile Gly Gly
1               5                   10                  15

Met Ala Val Asp Val Met Glu Val Glu Met Pro Thr Ala Arg Arg Thr
            20                  25                  30

Leu Val Leu Val Phe Ile Gln Ala Ala Thr Val Leu Ala Thr Leu His
        35                  40                  45

Gly Met His Val Leu His Glu Leu Tyr Leu Ser Ser Phe Asp Glu Glu
    50                  55                  60

Phe Gln Trp Glu Val Glu Ser Trp Arg Leu His Leu Val Leu Tyr Tyr
65                  70                  75                  80

Val Val Val Val Gly Leu Ala Leu Phe Cys Leu Asp Gly Gly His Ala
                85                  90                  95

Asp Glu Pro Ala Arg Glu Ala Gly Pro Asp Leu Gly Ala Ser Gly Ser
            100                 105                 110

Glu Ser Glu Asp Glu Gly Ala Gln Ala Gly Ala Val Gln Gly Pro Glu
        115                 120                 125

Thr Leu Arg Ser Gln Val Ser Gly Xaa Arg Arg Arg Ala Val Asp Leu
    130                 135                 140

Gln Glu Phe Phe Gln Gly Ala Arg Glu Val Xaa Met Val Leu Asp Leu
145                 150                 155                 160

His Arg Ala Ile Gly Gly Glu Leu His Gly Leu Gln Gly Pro Val Pro
                165                 170                 175
```

Leu Gly Cys Asp His Arg Pro Pro Phe Leu Gly Arg Leu Gly Arg
            180                 185                 190

Arg Gly Arg Cys Leu Phe His Gly
        195                 200

<210> SEQ ID NO 11
<211> LENGTH: 391
<212> TYPE: PRT
<213> ORGANISM: chimpanzee C68 adenovirus protein

<400> SEQUENCE: 11

Met His Pro Val Leu Arg Gln Met Arg Pro His His Pro Pro Pro Gln
1               5                   10                  15

Gln Gln Pro Pro Gln Pro Ala Leu Leu Pro Pro Gln Gln Gln
            20                  25                  30

Leu Pro Ala Thr Thr Ala Ala Ala Val Ser Gly Ala Gly Gln Ser
        35                  40                  45

Tyr Asp His Gln Leu Ala Leu Glu Glu Gly Glu Gly Leu Ala Arg Leu
    50                  55                  60

Gly Ala Ser Ser Pro Glu Arg His Pro Arg Val Gln Met Lys Arg Asp
65                  70                  75                  80

Ala Arg Glu Ala Tyr Val Pro Lys Gln Asn Leu Phe Arg Asp Arg Ser
                85                  90                  95

Gly Glu Glu Pro Glu Glu Met Arg Ala Ala Arg Phe His Ala Gly Arg
            100                 105                 110

Glu Leu Arg Arg Gly Leu Asp Arg Lys Arg Val Leu Arg Asp Glu Asp
        115                 120                 125

Phe Glu Ala Asp Glu Leu Thr Gly Ile Ser Pro Ala Arg Ala His Val
    130                 135                 140

Ala Ala Ala Asn Leu Val Thr Ala Tyr Glu Gln Thr Val Lys Glu Glu
145                 150                 155                 160

Ser Asn Phe Gln Lys Ser Phe Asn Asn His Val Arg Thr Leu Ile Ala
                165                 170                 175

Arg Glu Glu Val Thr Leu Gly Leu Met His Leu Trp Asp Leu Leu Glu
            180                 185                 190

Ala Ile Val Gln Asn Pro Thr Ser Lys Pro Leu Thr Ala Gln Leu Phe
        195                 200                 205

Leu Val Val Gln His Ser Arg Asp Asn Glu Ala Phe Arg Glu Ala Leu
    210                 215                 220

Leu Asn Ile Thr Glu Pro Glu Gly Arg Trp Leu Leu Asp Leu Val Asn
225                 230                 235                 240

Ile Leu Gln Ser Ile Val Val Gln Glu Arg Gly Leu Pro Leu Ser Glu
                245                 250                 255

Lys Leu Ala Ala Ile Asn Phe Ser Val Leu Ser Leu Gly Lys Tyr Tyr
            260                 265                 270

Ala Arg Lys Ile Tyr Lys Thr Pro Tyr Val Pro Ile Asp Lys Glu Val
        275                 280                 285

Lys Ile Asp Gly Phe Tyr Met Arg Met Thr Leu Lys Val Leu Thr Leu
    290                 295                 300

Ser Asp Asp Leu Gly Val Tyr Arg Asn Asp Arg Met His Arg Ala Val
305                 310                 315                 320

Ser Ala Ser Arg Arg Arg Glu Leu Ser Asp Gln Glu Leu Met His Ser
                325                 330                 335

Leu Gln Arg Ala Leu Thr Gly Ala Gly Thr Glu Gly Glu Ser Tyr Phe

-continued

```
            340                 345                 350
Asp Met Gly Ala Asp Leu His Trp Gln Pro Ser Arg Arg Ala Leu Glu
        355                 360                 365
Ala Ala Ala Gly Pro Tyr Val Glu Val Asp Asp Glu Val Asp Glu
    370                 375                 380
Glu Gly Glu Tyr Leu Glu Asp
385                 390
```

<210> SEQ ID NO 12
<211> LENGTH: 534
<212> TYPE: PRT
<213> ORGANISM: chimpanzee C68 adenovirus protein

<400> SEQUENCE: 12

```
Met Met Arg Arg Ala Tyr Pro Glu Gly Pro Pro Ser Tyr Glu Ser
1               5                   10                  15
Val Met Gln Gln Ala Met Ala Ala Ala Met Gln Pro Pro Leu Glu
            20                  25                  30
Ala Pro Tyr Val Pro Pro Arg Tyr Leu Ala Pro Thr Glu Gly Arg Asn
        35                  40                  45
Ser Ile Arg Tyr Ser Glu Leu Ala Pro Leu Tyr Asp Thr Thr Arg Leu
    50                  55                  60
Tyr Leu Val Asp Asn Lys Ser Ala Asp Ile Ala Ser Leu Asn Tyr Gln
65                  70                  75                  80
Asn Asp His Ser Asn Phe Leu Thr Thr Val Val Gln Asn Asn Asp Phe
                85                  90                  95
Thr Pro Thr Glu Ala Ser Thr Gln Thr Ile Asn Phe Asp Glu Arg Ser
            100                 105                 110
Arg Trp Gly Gly Gln Leu Lys Thr Ile Met His Thr Asn Met Pro Asn
        115                 120                 125
Val Asn Glu Phe Met Tyr Ser Asn Lys Phe Lys Ala Arg Val Met Val
    130                 135                 140
Ser Arg Lys Thr Pro Asn Gly Val Thr Val Thr Glu Asp Tyr Asp Gly
145                 150                 155                 160
Ser Gln Asp Glu Leu Lys Tyr Glu Trp Val Glu Phe Glu Leu Pro Glu
                165                 170                 175
Gly Asn Phe Ser Val Thr Met Thr Ile Asp Leu Met Asn Asn Ala Ile
            180                 185                 190
Ile Asp Asn Tyr Leu Ala Val Gly Arg Gln Asn Gly Val Leu Glu Ser
        195                 200                 205
Asp Ile Gly Val Lys Phe Asp Thr Arg Asn Phe Arg Leu Gly Trp Asp
    210                 215                 220
Pro Val Thr Glu Leu Val Met Pro Gly Val Tyr Thr Asn Glu Ala Phe
225                 230                 235                 240
His Pro Asp Ile Val Leu Leu Pro Gly Cys Gly Val Asp Phe Thr Glu
                245                 250                 255
Ser Arg Leu Ser Asn Leu Leu Gly Ile Arg Lys Arg Gln Pro Phe Gln
            260                 265                 270
Glu Gly Phe Gln Ile Met Tyr Glu Asp Leu Glu Gly Gly Asn Ile Pro
        275                 280                 285
Ala Leu Leu Asp Val Asp Ala Tyr Glu Lys Ser Lys Glu Asp Ala Ala
    290                 295                 300
Ala Glu Ala Thr Ala Ala Val Ala Thr Ala Ser Thr Glu Val Arg Gly
305                 310                 315                 320
```

```
Asp Asn Phe Ala Ser Ala Ala Val Ala Ala Glu Ala Ala Glu
            325                 330                 335

Thr Glu Ser Lys Ile Val Ile Gln Pro Val Glu Lys Asp Ser Lys Asn
            340                 345                 350

Arg Ser Tyr Asn Val Leu Pro Asp Lys Ile Asn Thr Ala Tyr Arg Ser
            355                 360                 365

Trp Tyr Leu Ala Tyr Asn Tyr Gly Asp Pro Glu Lys Gly Val Arg Ser
            370                 375                 380

Trp Thr Leu Leu Thr Thr Ser Asp Val Thr Cys Gly Val Glu Gln Val
385                 390                 395                 400

Tyr Trp Ser Leu Pro Asp Met Met Gln Asp Pro Val Thr Phe Arg Ser
                405                 410                 415

Thr Arg Gln Val Ser Asn Tyr Pro Val Val Gly Ala Glu Leu Leu Pro
            420                 425                 430

Val Tyr Ser Lys Ser Phe Phe Asn Glu Gln Ala Val Tyr Ser Gln Gln
            435                 440                 445

Leu Arg Ala Phe Thr Ser Leu Thr His Val Phe Asn Arg Phe Pro Glu
    450                 455                 460

Asn Gln Ile Leu Val Arg Pro Pro Ala Pro Thr Ile Thr Thr Val Ser
465                 470                 475                 480

Glu Asn Val Pro Ala Leu Thr Asp His Gly Thr Leu Pro Leu Arg Ser
                485                 490                 495

Ser Ile Arg Gly Val Gln Arg Val Thr Val Thr Asp Ala Arg Arg Arg
                500                 505                 510

Thr Cys Pro Tyr Val Tyr Lys Ala Leu Gly Ile Val Ala Pro Arg Val
            515                 520                 525

Leu Ser Ser Arg Thr Phe
    530

<210> SEQ ID NO 13
<211> LENGTH: 201
<212> TYPE: PRT
<213> ORGANISM: chimpanzee C68 adenovirus protein
<220> FEATURE:
<221> NAME/KEY: MISC_FEATURE
<222> LOCATION: (70)..(70)
<223> OTHER INFORMATION: Xaa can be any amino acid

<400> SEQUENCE: 13

Met Ser Ile Leu Ile Ser Pro Ser Asn Asn Thr Gly Trp Gly Leu Arg
1               5                   10                  15

Ala Pro Ser Lys Met Tyr Gly Gly Ala Arg Gln Arg Ser Thr Gln His
            20                  25                  30

Pro Val Arg Val Arg Gly His Phe Arg Ala Pro Trp Gly Ala Leu Lys
        35                  40                  45

Gly Arg Val Arg Ser Arg Thr Thr Val Asp Asp Val Ile Asp Gln Val
    50                  55                  60

Val Ala Asp Ala Arg Xaa Tyr Thr Pro Ala Ala Ala Pro Val Ser Thr
65                  70                  75                  80

Val Asp Ala Val Ile Asp Ser Val Val Ala Asp Ala Arg Arg Tyr Ala
                85                  90                  95

Arg Ala Lys Ser Arg Arg Arg Ile Ala Arg His Arg Ser Thr
            100                 105                 110

Pro Ala Met Arg Ala Ala Arg Ser Leu Val Ala Gln Gly Gln Ala His
            115                 120                 125

Gly Thr Gln Gly His Val Gln Gly Gly Gln Thr Arg Gly Phe Arg Arg
```

```
            130                 135                 140
Gln Arg Arg Gln Asp Pro Glu Thr Arg Gly His Gly Gly Gly Ser Gly
145                 150                 155                 160

His Arg Gln His Val Pro Pro Ala Ala Arg Glu Arg Val Leu Gly Ala
                165                 170                 175

Arg Arg Arg His Arg Cys Ala Arg Ala Arg Ala His Pro Pro Pro Ser
            180                 185                 190

His Leu Lys Met Phe Thr Ser Arg Cys
            195                 200

<210> SEQ ID NO 14
<211> LENGTH: 356
<212> TYPE: PRT
<213> ORGANISM: chimpanzee C68 adenovirus protein
<220> FEATURE:
<221> NAME/KEY: MISC_FEATURE
<222> LOCATION: (111)..(111)
<223> OTHER INFORMATION: Xaa can be any amino acid
<220> FEATURE:
<221> NAME/KEY: MISC_FEATURE
<222> LOCATION: (183)..(183)
<223> OTHER INFORMATION: Xaa can be any amino acid
<220> FEATURE:
<221> NAME/KEY: MISC_FEATURE
<222> LOCATION: (212)..(212)
<223> OTHER INFORMATION: Xaa can be any amino acid
<220> FEATURE:
<221> NAME/KEY: MISC_FEATURE
<222> LOCATION: (220)..(220)
<223> OTHER INFORMATION: Xaa can be any amino acid

<400> SEQUENCE: 14

Met Ser Lys Arg Lys Phe Lys Glu Glu Met Leu Gln Val Ile Ala Pro
1               5                   10                  15

Glu Ile Tyr Gly Pro Ala Val Val Lys Glu Arg Lys Pro Arg Lys
            20                  25                  30

Ile Lys Arg Val Lys Lys Asp Lys Glu Glu Ser Asp Val Asp
            35                  40                  45

Gly Leu Val Glu Phe Val Arg Glu Phe Ala Pro Arg Arg Arg Val Gln
    50                  55                  60

Trp Arg Gly Arg Lys Val Gln Pro Val Leu Arg Pro Gly Thr Thr Val
65                  70                  75                  80

Val Phe Thr Pro Gly Glu Arg Ser Gly Thr Ala Ser Lys Arg Ser Tyr
                85                  90                  95

Asp Glu Val Tyr Gly Asp Asp Ile Leu Glu Gln Ala Ala Xaa Arg
            100                 105                 110

Leu Gly Glu Phe Ala Tyr Gly Lys Arg Ser Arg Ser Ala Pro Lys Glu
            115                 120                 125

Glu Ala Val Ser Ile Pro Leu Asp His Gly Asn Pro Thr Pro Ser Leu
130                 135                 140

Lys Pro Val Thr Leu Gln Gln Val Leu Pro Thr Ala Ala Pro Arg Arg
145                 150                 155                 160

Gly Phe Lys Arg Glu Gly Glu Asp Leu Tyr Pro Thr Met Gln Leu Met
                165                 170                 175

Val Pro Lys Arg Gln Lys Xaa Glu Asp Val Leu Glu Thr Met Lys Val
            180                 185                 190

Asp Pro Asp Val Gln Pro Glu Val Lys Val Arg Pro Ile Lys Gln Val
            195                 200                 205

Ala Pro Gly Xaa Gly Val Gln Thr Val Asp Ile Xaa Ile Pro Thr Glu
            210                 215                 220
```

Pro Met Glu Thr Gln Thr Glu Pro Met Ile Lys Pro Ser Thr Ser Thr
225                 230                 235                 240

Met Glu Val Gln Thr Asp Pro Trp Met Pro Ser Ala Pro Ser Arg Arg
            245                 250                 255

Pro Arg Arg Lys Tyr Gly Ala Ala Ser Leu Leu Met Pro Asn Tyr Ala
        260                 265                 270

Leu His Pro Ser Ile Ile Pro Thr Pro Gly Tyr Arg Gly Thr Arg Phe
    275                 280                 285

Tyr Arg Gly His Thr Ser Ser Arg Arg Lys Thr Thr Thr Arg Arg
290                 295                 300

Ser Pro Ser Pro His Arg Arg Cys Asn His Pro Cys Arg Pro Gly Ala
305                 310                 315                 320

Glu Ser Val Pro Pro Arg Pro Arg Thr Ser Asp Pro Ala Ala Arg Ala
            325                 330                 335

Leu Pro Pro Glu His Arg His Leu Asn Phe Arg Gln Leu Cys Arg Ser
        340                 345                 350

Met Ala Leu Thr
        355

<210> SEQ ID NO 15
<211> LENGTH: 257
<212> TYPE: PRT
<213> ORGANISM: chimpanzee C68 adenovirus protein
<220> FEATURE:
<221> NAME/KEY: MISC_FEATURE
<222> LOCATION: (202)..(202)
<223> OTHER INFORMATION: Xaa can be any amino acid
<220> FEATURE:
<221> NAME/KEY: MISC_FEATURE
<222> LOCATION: (210)..(210)
<223> OTHER INFORMATION: Xaa can be any amino acid
<220> FEATURE:
<221> NAME/KEY: MISC_FEATURE
<222> LOCATION: (256)..(256)
<223> OTHER INFORMATION: Xaa can be any amino acid

<400> SEQUENCE: 15

Met Asp Ser Asp Ala Pro Gly Pro Val Met Cys Phe Arg Arg Gln Met
1               5                   10                  15

Glu Asp Ile Asn Phe Ser Ser Leu Ala Pro Arg His Gly Thr Arg Pro
            20                  25                  30

Phe Met Gly Thr Trp Ser Asp Ile Gly Thr Ser Gln Leu Asn Gly Gly
        35                  40                  45

Ala Phe Asn Trp Ser Ser Leu Trp Ser Gly Leu Lys Asn Phe Gly Ser
    50                  55                  60

Thr Leu Lys Thr Tyr Gly Ser Lys Ala Trp Asn Ser Thr Thr Gly Gln
65                  70                  75                  80

Ala Leu Arg Asp Lys Leu Lys Glu Gln Asn Phe Gln Gln Lys Val Val
                85                  90                  95

Asp Gly Leu Ala Ser Gly Ile Asn Gly Val Val Asp Leu Ala Asn Gln
            100                 105                 110

Ala Val Gln Arg Gln Ile Asn Ser Arg Leu Asp Pro Val Pro Pro Ala
        115                 120                 125

Gly Ser Val Glu Met Pro Gln Val Glu Glu Leu Pro Pro Leu Asp
    130                 135                 140

Lys Arg Gly Glu Lys Arg Pro Arg Pro Asp Ala Glu Glu Thr Leu Leu
145                 150                 155                 160

Thr His Thr Asp Glu Pro Pro Pro Tyr Glu Glu Ala Val Lys Leu Gly

-continued

```
                165                 170                 175
Leu Pro Thr Thr Arg Pro Ile Ala Pro Leu Ala Thr Gly Val Leu Lys
            180                 185                 190

Pro Glu Lys Pro Ala Thr Leu Asp Leu Xaa Pro Pro Gln Pro Ser Arg
        195                 200                 205

Pro Xaa Thr Val Ala Lys Pro Leu Pro Pro Val Ala Val Ala Arg Ala
    210                 215                 220

Arg Pro Gly Gly Thr Ala Arg Pro His Ala Asn Trp Gln Ser Thr Leu
225                 230                 235                 240

Asn Ser Ile Val Gly Leu Gly Val Gln Ser Val Lys Arg Arg Arg Xaa
                245                 250                 255

Tyr

<210> SEQ ID NO 16
<211> LENGTH: 933
<212> TYPE: PRT
<213> ORGANISM: chimpanzee C68 adenovirus protein
<220> FEATURE:
<221> NAME/KEY: MISC_FEATURE
<222> LOCATION: (826)..(826)
<223> OTHER INFORMATION: Xaa can be any amino acid
<220> FEATURE:
<221> NAME/KEY: MISC_FEATURE
<222> LOCATION: (922)..(922)
<223> OTHER INFORMATION: Xaa can be any amino acid

<400> SEQUENCE: 16

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Cys Gln Trp Thr Tyr Lys Ala Asp Gly Glu Thr Ala
    130                 135                 140

Thr Glu Lys Thr Tyr Thr Tyr Gly Asn Ala Pro Val Gln Gly Ile Asn
145                 150                 155                 160

Ile Thr Lys Asp Gly Ile Gln Leu Gly Thr Asp Thr Asp Gln Pro
                165                 170                 175

Ile Tyr Ala Asp Lys Thr Tyr Gln Pro Glu Pro Gln Val Gly Asp Ala
            180                 185                 190

Glu Trp His Asp Ile Thr Gly Thr Asp Glu Lys Tyr Gly Gly Arg Ala
        195                 200                 205

Leu Lys Pro Asp Thr Lys Met Lys Pro Cys Tyr Gly Ser Phe Ala Lys
    210                 215                 220

Pro Thr Asn Lys Glu Gly Gly Gln Ala Asn Val Lys Thr Gly Thr Gly
225                 230                 235                 240
```

```
Thr Thr Lys Glu Tyr Asp Ile Asp Met Ala Phe Phe Asp Asn Arg Ser
            245                 250                 255

Ala Ala Ala Ala Gly Leu Ala Pro Glu Ile Val Leu Tyr Thr Glu Asn
        260                 265                 270

Val Asp Leu Glu Thr Pro Asp Thr His Ile Val Tyr Lys Ala Gly Thr
    275                 280                 285

Asp Asp Ser Ser Ser Ile Asn Leu Gly Gln Gln Ala Met Pro Asn
290                 295                 300

Arg Pro Asn Tyr Ile Gly Phe Arg Asp Asn Phe Ile Gly Leu Met Tyr
305                 310                 315                 320

Tyr Asn Ser Thr Gly Asn Met Gly Val Leu Ala Gly Gln Ala Ser Gln
                325                 330                 335

Leu Asn Ala Val Val Asp Leu Gln Asp Arg Asn Thr Glu Leu Ser Tyr
            340                 345                 350

Gln Leu Leu Leu Asp Ser Leu Gly Asp Arg Thr Arg Tyr Phe Ser Met
        355                 360                 365

Trp Asn Gln Ala Val Asp Ser Tyr Asp Pro Asp Val Arg Ile Ile Glu
    370                 375                 380

Asn His Gly Val Glu Asp Glu Leu Pro Asn Tyr Cys Phe Pro Leu Asp
385                 390                 395                 400

Ala Val Gly Arg Thr Asp Thr Tyr Gln Gly Ile Lys Ala Asn Gly Thr
                405                 410                 415

Asp Gln Thr Thr Trp Thr Lys Asp Asp Ser Val Asn Asp Ala Asn Glu
            420                 425                 430

Ile Gly Lys Gly Asn Pro Phe Ala Met Glu Ile Asn Ile Gln Ala Asn
        435                 440                 445

Leu Trp Arg Asn Phe Leu Tyr Ala Asn Val Ala Leu Tyr Leu Pro Asp
    450                 455                 460

Ser Tyr Lys Tyr Thr Pro Ala Asn Val Thr Leu Pro Thr Asn Thr Asn
465                 470                 475                 480

Thr Tyr Asp Tyr Met Asn Gly Arg Val Val Ala Pro Ser Leu Val Asp
                485                 490                 495

Ser Tyr Ile Asn Ile Gly Ala Arg Trp Ser Leu Asp Pro Met Asp Asn
            500                 505                 510

Val Asn Pro Phe Asn His His Arg Asn Ala Gly Leu Arg Tyr Arg Ser
        515                 520                 525

Met Leu Leu Gly Asn Gly Arg Tyr Val Pro Phe His Ile Gln Val Pro
    530                 535                 540

Gln Lys Phe Phe Ala Ile Lys Ser Leu Leu Leu Pro Gly Ser Tyr
545                 550                 555                 560

Thr Tyr Glu Trp Asn Phe Arg Lys Asp Val Asn Met Ile Leu Gln Ser
                565                 570                 575

Ser Leu Gly Asn Asp Leu Arg Thr Asp Gly Ala Ser Ile Ser Phe Thr
            580                 585                 590

Ser Ile Asn Leu Tyr Ala Thr Phe Phe Pro Met Ala His Asn Thr Ala
        595                 600                 605

Ser Thr Leu Glu Ala Met Leu Arg Asn Asp Thr Asn Asp Gln Ser Phe
    610                 615                 620

Asn Asp Tyr Leu Ser Ala Ala Asn Met Leu Tyr Pro Ile Pro Ala Asn
625                 630                 635                 640

Ala Thr Asn Val Pro Ile Ser Ile Pro Ser Arg Asn Trp Ala Ala Phe
                645                 650                 655
```

```
Arg Gly Trp Ser Phe Thr Arg Leu Lys Thr Lys Glu Thr Pro Ser Leu
                660                 665                 670

Gly Ser Gly Phe Asp Pro Tyr Phe Val Tyr Ser Gly Ser Ile Pro Tyr
            675                 680                 685

Leu Asp Gly Thr Phe Tyr Leu Asn His Thr Phe Lys Lys Val Ser Ile
        690                 695                 700

Thr Phe Asp Ser Ser Val Ser Trp Pro Gly Asn Asp Arg Leu Leu Thr
705                 710                 715                 720

Pro Asn Glu Phe Glu Ile Lys Arg Thr Val Asp Gly Glu Gly Tyr Asn
                725                 730                 735

Val Ala Gln Cys Asn Met Thr Lys Asp Trp Phe Leu Val Gln Met Leu
            740                 745                 750

Ala His Tyr Asn Ile Gly Tyr Gln Gly Phe Tyr Val Pro Glu Gly Tyr
        755                 760                 765

Lys Asp Arg Met Tyr Ser Phe Phe Arg Asn Phe Gln Pro Met Ser Arg
770                 775                 780

Gln Val Val Asp Glu Val Asn Tyr Lys Asp Tyr Gln Ala Val Thr Leu
785                 790                 795                 800

Ala Tyr Gln His Asn Asn Ser Gly Phe Val Gly Tyr Leu Ala Pro Thr
                805                 810                 815

Met Arg Gln Gly Gln Pro Tyr Pro Ala Xaa Tyr Pro Tyr Pro Leu Ile
            820                 825                 830

Gly Lys Ser Ala Val Thr Ser Val Thr Gln Lys Lys Phe Leu Cys Asp
        835                 840                 845

Arg Val Met Trp Arg Ile Pro Phe Ser Ser Asn Phe Met Ser Met Gly
850                 855                 860

Ala Leu Thr Asp Leu Gly Gln Asn Met Leu Tyr Ala Asn Ser Ala His
865                 870                 875                 880

Ala Leu Asp Met Asn Phe Glu Val Asp Pro Met Asp Glu Ser Thr Leu
                885                 890                 895

Leu Tyr Val Val Phe Glu Val Phe Asp Val Val Arg Val His Gln Pro
            900                 905                 910

His Arg Gly Val Ile Glu Ala Val Tyr Xaa Arg Thr Pro Phe Ser Ala
        915                 920                 925

Gly Asn Ala Thr Thr
    930

<210> SEQ ID NO 17
<211> LENGTH: 513
<212> TYPE: PRT
<213> ORGANISM: chimpanzee C68 adenovirus protein
<220> FEATURE:
<221> NAME/KEY: MISC_FEATURE
<222> LOCATION: (511)..(511)
<223> OTHER INFORMATION: Xaa can be any amino acid

<400> SEQUENCE: 17

Met Ala Gly Arg Gly Gly Ser Gln Ser Glu Arg Arg Glu Arg Thr
1               5                   10                  15

Pro Glu Arg Gly Arg Gly Ser Ala Ser His Pro Pro Ser Arg Gly Gly
                20                  25                  30

Glu Ser Pro Ser Pro Pro Pro Leu Pro Pro Lys Arg His Thr Tyr Arg
            35                  40                  45

Arg Val Ala Ser Asp Gln Glu Glu Glu Ile Val Val Val Ser Glu
        50                  55                  60

Asn Ser Arg Ser Pro Ser Pro Ser Pro Thr Ser Pro Pro Pro Leu Pro
```

```
              65                  70                  75                  80
Pro Lys Lys Pro Arg Lys Thr Lys His Val Val Leu Gln Asp Val
                    85                  90                  95
Ser Gln Asp Ser Glu Asp Glu Arg Gln Ala Glu Glu Leu Ala Ala
                    100                 105                 110
Val Gly Phe Ser Tyr Pro Val Arg Ile Thr Glu Lys Asp Gly Lys
                    115                 120                 125
Arg Ser Phe Glu Thr Leu Asp Glu Ser Asp Pro Leu Ala Ala Ala
                    130                 135                 140
Ser Ala Lys Met Met Val Lys Asn Pro Met Ser Leu Pro Ile Val Ser
145                 150                 155                 160
Ala Trp Glu Lys Gly Met Glu Ile Met Thr Met Leu Met Asp Arg Tyr
                    165                 170                 175
Arg Val Glu Thr Asp Leu Lys Ala Asn Phe Gln Leu Met Pro Glu Gln
                    180                 185                 190
Gly Glu Val Tyr Arg Arg Ile Cys His Leu Tyr Ile Asn Glu Glu His
                    195                 200                 205
Arg Gly Ile Pro Leu Thr Phe Thr Ser Asn Lys Thr Leu Thr Thr Met
210                 215                 220
Met Gly Arg Phe Leu Gln Gly Phe Val His Ala His Ser Gln Ile Ala
225                 230                 235                 240
His Lys Asn Trp Glu Cys Thr Gly Cys Ala Leu Trp Leu His Gly Cys
                    245                 250                 255
Thr Glu Ala Glu Gly Lys Leu Arg Cys Leu His Gly Thr Thr Met Ile
                    260                 265                 270
Gln Lys Glu His Met Ile Glu Met Asp Val Ala Ser Glu Asn Gly Gln
                    275                 280                 285
Arg Ala Leu Lys Glu Asn Pro Asp Arg Ala Lys Ile Thr Gln Asn Arg
                    290                 295                 300
Trp Gly Arg Ser Val Val Gln Leu Ala Asn Asn Asp Ala Arg Cys Cys
305                 310                 315                 320
Val His Asp Ala Gly Cys Ala Thr Asn Gln Phe Ser Ser Lys Ser Cys
                    325                 330                 335
Gly Val Phe Phe Thr Glu Gly Ala Lys Ala Gln Gln Ala Phe Arg Gln
                    340                 345                 350
Leu Glu Ala Phe Met Lys Ala Met Tyr Pro Gly Met Asn Ala Asp Gln
                    355                 360                 365
Ala Gln Met Met Leu Ile Pro Leu His Cys Asp Cys Asn His Lys Pro
                    370                 375                 380
Gly Cys Val Pro Thr Met Gly Arg Gln Thr Cys Lys Met Thr Pro Phe
385                 390                 395                 400
Gly Met Ala Asn Ala Glu Asp Leu Asp Val Glu Ser Ile Thr Asp Ala
                    405                 410                 415
Thr Val Leu Ala Ser Val Lys His Pro Ala Leu Met Val Phe Gln Cys
                    420                 425                 430
Cys Asn Pro Val Tyr Arg Asn Ser Arg Ala Gln Asn Ala Gly Pro Asn
                    435                 440                 445
Cys Asp Phe Lys Ile Ser Ala Pro Asp Leu Gly Ala Leu Gln Leu
                    450                 455                 460
Thr Arg Lys Leu Trp Thr Asp Ser Phe Pro Asp Thr Pro Leu Pro Lys
465                 470                 475                 480
Leu Leu Ile Pro Glu Phe Lys Trp Leu Ala Lys Tyr Gln Phe Arg Asn
                    485                 490                 495
```

```
Val Ser Leu Pro Ala Gly His Ala Glu Thr Arg Lys Asn Pro Xaa Asp
            500                 505                 510

Phe

<210> SEQ ID NO 18
<211> LENGTH: 222
<212> TYPE: PRT
<213> ORGANISM: chimpanzee C68 adenovirus protein

<400> SEQUENCE: 18

Met Pro Arg Gly Asn Lys Lys Leu Lys Val Glu Leu Pro Pro Val Glu
1               5                   10                  15

Asp Leu Glu Glu Asp Trp Glu Asn Ser Ser Gln Ala Glu Glu Glu Glu
            20                  25                  30

Met Glu Glu Asp Trp Asp Ser Thr Gln Ala Glu Glu Asp Ser Leu Gln
        35                  40                  45

Asp Ser Leu Glu Glu Asp Glu Glu Ala Glu Glu Val Glu Glu
50                  55                  60

Ala Ala Ala Ala Arg Pro Ser Ser Ala Gly Glu Lys Ala Ser Ser
65                  70                  75                  80

Thr Asp Thr Ile Ser Ala Pro Gly Arg Gly Pro Ala Arg Pro His Ser
                85                  90                  95

Arg Trp Asp Glu Thr Gly Arg Phe Pro Asn Pro Thr Gln Thr Ala
                100                 105                 110

Pro Thr Thr Ser Lys Lys Arg Gln Gln Gln Gln Lys Lys Thr Ser Arg
            115                 120                 125

Lys Pro Ala Ala Arg Lys Ser Thr Ala Ala Ala Gly Gly Leu Arg
130                 135                 140

Ile Ala Ala Asn Glu Pro Ala Gln Thr Arg Glu Leu Arg Asn Arg Ile
145                 150                 155                 160

Phe Pro Thr Leu Tyr Ala Ile Phe Gln Gln Ser Arg Gly Gln Glu Gln
                165                 170                 175

Glu Leu Lys Val Lys Asn Arg Ser Leu Arg Ser Leu Thr Arg Ser Cys
            180                 185                 190

Leu Tyr His Lys Ser Glu Asp Gln Leu Gln Arg Thr Leu Glu Asp Ala
        195                 200                 205

Glu Ala Leu Phe Asn Lys Tyr Cys Ala Leu Thr Leu Lys Glu
    210                 215                 220

<210> SEQ ID NO 19
<211> LENGTH: 227
<212> TYPE: PRT
<213> ORGANISM: chimpanzee C68 adenovirus protein

<400> SEQUENCE: 19

Met Ser Lys Glu Ile Pro Thr Pro Tyr Met Trp Ser Tyr Gln Pro Gln
1               5                   10                  15

Met Gly Leu Ala Ala Gly Ala Ala Gln Asp Tyr Ser Thr Arg Met Asn
            20                  25                  30

Trp Leu Ser Ala Gly Pro Ala Met Ile Ser Arg Val Asn Asp Ile Arg
        35                  40                  45

Ala His Arg Asn Gln Ile Leu Leu Glu Gln Ser Ala Leu Thr Ala Thr
    50                  55                  60

Pro Arg Asn His Leu Asn Pro Arg Asn Trp Pro Ala Ala Leu Val Tyr
65                  70                  75                  80
```

```
Gln Glu Ile Pro Gln Pro Thr Thr Val Leu Leu Pro Arg Asp Ala Gln
                85                  90                  95

Ala Glu Val Gln Leu Thr Asn Ser Gly Val Gln Leu Ala Gly Gly Ala
            100                 105                 110

Thr Leu Cys Arg His Arg Pro Ala Gln Gly Ile Lys Arg Leu Val Ile
        115                 120                 125

Arg Gly Arg Ser Thr Gln Leu Asn Asp Glu Val Val Ser Ser Ser Leu
    130                 135                 140

Gly Leu Arg Pro Asp Gly Val Phe Gln Leu Ala Gly Ser Gly Arg Ser
145                 150                 155                 160

Ser Phe Thr Pro Arg Gln Ala Val Leu Thr Leu Glu Ser Ser Ser Ser
                165                 170                 175

Gln Pro Arg Ser Gly Gly Ile Gly Thr Leu Gln Phe Val Glu Glu Phe
            180                 185                 190

Thr Pro Ser Val Tyr Phe Asn Pro Phe Ser Gly Ser Pro Gly His Tyr
        195                 200                 205

Pro Asp Glu Phe Ile Pro Asn Phe Asp Ala Ile Ser Glu Ser Val Asp
    210                 215                 220

Gly Tyr Asp
225

<210> SEQ ID NO 20
<211> LENGTH: 106
<212> TYPE: PRT
<213> ORGANISM: chimpanzee C68 adenovirus protein

<400> SEQUENCE: 20

Met Ser His Gly Gly Ala Ala Asp Leu Ala Arg Leu Arg His Leu Asp
1               5                   10                  15

His Cys Arg Arg Phe Arg Cys Phe Ala Arg Asp Leu Ala Glu Phe Ala
            20                  25                  30

Tyr Phe Glu Leu Pro Glu Glu His Pro Gln Gly Pro Ala His Gly Val
        35                  40                  45

Arg Ile Val Val Glu Gly Gly Leu Asp Ser His Leu Leu Arg Ile Phe
    50                  55                  60

Ser Gln Arg Pro Ile Leu Val Glu Arg Glu Gln Gly Gln Thr Leu Leu
65                  70                  75                  80

Thr Leu Tyr Cys Ile Cys Asn His Pro Gly Leu His Glu Ser Leu Cys
                85                  90                  95

Cys Leu Leu Cys Thr Glu Tyr Asn Lys Ser
            100                 105

<210> SEQ ID NO 21
<211> LENGTH: 146
<212> TYPE: PRT
<213> ORGANISM: chimpanzee C68 adenovirus protein
<220> FEATURE:
<221> NAME/KEY: MISC_FEATURE
<222> LOCATION: (62)..(62)
<223> OTHER INFORMATION: Xaa can be any amino acid

<400> SEQUENCE: 21

Met Lys Val Phe Val Val Cys Cys Val Leu Ser Ile Ile Lys Ala Glu
1               5                   10                  15

Thr Ala Thr Thr Pro Asp Phe Arg Val Ser Lys Leu Gln Leu Phe Gln
            20                  25                  30

Pro Phe Leu Pro Gly Thr Tyr Gln Cys Val Ser Gly Pro Cys His His
        35                  40                  45
```

```
Thr Phe His Leu Ile Pro Asn Thr Thr Ala Ser Leu Pro Xaa Thr Asn
             50                  55                  60

Asn Gln Thr Asn Leu His Gln Arg His Arg Arg Asp Leu Ser Glu Ser
 65                  70                  75                  80

Asn Thr Thr Thr His Thr Gly Gly Glu Leu Arg Gly Gln Pro Thr Ser
                 85                  90                  95

Gly Ile Tyr Tyr Gly Pro Trp Glu Val Val Gly Leu Ile Thr Leu Gly
                100                 105                 110

Leu Val Ala Gly Gly Leu Leu Val Leu Cys Tyr Leu Tyr Leu Pro Cys
             115                 120                 125

Cys Ser Tyr Leu Val Val Leu Cys Cys Trp Phe Lys Lys Trp Gly Arg
     130                 135                 140

Ser Pro
145

<210> SEQ ID NO 22
<211> LENGTH: 176
<212> TYPE: PRT
<213> ORGANISM: chimpanzee C68 adenovirus protein
<220> FEATURE:
<221> NAME/KEY: MISC_FEATURE
<222> LOCATION: (28)..(28)
<223> OTHER INFORMATION: Xaa can be any amino acid

<400> SEQUENCE: 22

Met Gly Lys Ile Thr Leu Val Ser Cys Gly Ala Leu Val Ala Val Leu
 1               5                  10                  15

Leu Ser Ile Val Gly Leu Gly Gly Ala Ala Val Xaa Lys Glu Lys Ala
                20                  25                  30

Asp Pro Cys Leu His Phe Asn Pro Asn Lys Cys Gln Leu Ser Phe Gln
             35                  40                  45

Pro Asp Gly Asn Arg Cys Ala Val Leu Ile Lys Cys Gly Trp Glu Cys
     50                  55                  60

Glu Asn Val Arg Ile Glu Tyr Asn Asn Lys Thr Arg Asn Asn Thr Leu
 65                  70                  75                  80

Ala Ser Val Trp Gln Pro Gly Asp Pro Glu Trp Tyr Thr Val Ser Val
                 85                  90                  95

Pro Gly Ala Asp Gly Ser Pro Arg Thr Val Asn Asn Thr Phe Ile Phe
                100                 105                 110

Ala His Met Cys Asp Thr Val Met Trp Met Ser Lys Gln Tyr Asp Met
             115                 120                 125

Trp Pro Pro Thr Lys Glu Asn Ile Val Val Phe Ser Ile Ala Tyr Ser
     130                 135                 140

Leu Cys Thr Ala Leu Ile Thr Ala Ile Val Cys Leu Ser Ile His Met
145                 150                 155                 160

Leu Ile Ala Ile Arg Pro Arg Asn Asn Ala Glu Lys Glu Lys Gln Pro
                165                 170                 175

<210> SEQ ID NO 23
<211> LENGTH: 204
<212> TYPE: PRT
<213> ORGANISM: chimpanzee C68 adenovirus protein

<400> SEQUENCE: 23

Met Ala Ser Val Lys Phe Leu Leu Leu Phe Ala Ser Leu Ile Ala Val
 1               5                  10                  15

Ile His Gly Met Ser Asn Glu Lys Ile Thr Ile Tyr Thr Gly Thr Asn
```

-continued

```
                 20                  25                  30

His Thr Leu Lys Gly Pro Glu Lys Ala Thr Glu Val Ser Trp Tyr Cys
         35                  40                  45

Tyr Phe Asn Glu Ser Asp Val Ser Thr Glu Leu Cys Gly Asn Asn Asn
 50                  55                  60

Lys Lys Asn Glu Ser Ile Thr Leu Ile Lys Phe Gln Cys Gly Ser Asp
 65                  70                  75                  80

Leu Thr Leu Ile Asn Ile Thr Arg Asp Tyr Val Gly Met Tyr Tyr Gly
                 85                  90                  95

Thr Thr Ala Gly Ile Ser Asp Met Glu Phe Tyr Gln Val Ser Val Ser
            100                 105                 110

Glu Pro Thr Thr Pro Arg Met Thr Thr Thr Lys Thr Thr Pro Val
            115                 120                 125

Thr Thr Met Gln Leu Thr Thr Asn Asn Ile Phe Ala Met Arg Gln Met
130                 135                 140

Val Asn Ser Thr Gln Pro Thr Pro Ser Glu Glu Ile Pro Lys
145                 150                 155                 160

Ser Met Ile Gly Ile Ile Val Ala Val Val Cys Met Leu Ile Ile
                165                 170                 175

Ala Leu Cys Met Val Tyr Tyr Ala Phe Cys Tyr Arg Lys His Arg Leu
            180                 185                 190

Asn Asp Lys Leu Glu His Leu Leu Ser Val Glu Phe
            195                 200

<210> SEQ ID NO 24
<211> LENGTH: 91
<212> TYPE: PRT
<213> ORGANISM: chimpanzee C68 adenovirus protein

<400> SEQUENCE: 24

Met Ile Pro Arg Gln Phe Leu Ile Thr Ile Leu Ile Cys Leu Leu Gln
 1               5                  10                  15

Val Cys Ala Thr Leu Ala Leu Val Ala Asn Ala Ser Pro Asp Cys Ile
                20                  25                  30

Gly Pro Phe Ala Ser Tyr Val Leu Phe Ala Phe Thr Thr Cys Ile Cys
            35                  40                  45

Cys Cys Ser Ile Val Cys Leu Leu Ile Thr Phe Phe Gln Phe Ile Asp
 50                  55                  60

Trp Ile Phe Val Arg Ile Ala Tyr Leu Arg His His Pro Gln Tyr Arg
 65                  70                  75                  80

Asp Gln Arg Val Ala Arg Leu Leu Arg Leu Leu
                85                  90

<210> SEQ ID NO 25
<211> LENGTH: 143
<212> TYPE: PRT
<213> ORGANISM: chimpanzee C68 adenovirus protein
<220> FEATURE:
<221> NAME/KEY: MISC_FEATURE
<222> LOCATION: (5)..(5)
<223> OTHER INFORMATION: Xaa can be any amino acid

<400> SEQUENCE: 25

Met Arg Ala Val Xaa Leu Leu Ala Leu Leu Leu Val Leu Pro Arg
 1               5                  10                  15

Pro Val Asp Pro Arg Ser Pro Thr Gln Ser Pro Glu Glu Val Arg Lys
                20                  25                  30
```

```
Cys Lys Phe Gln Glu Pro Trp Lys Phe Leu Lys Cys Tyr Arg Gln Lys
            35                  40                  45

Ser Asp Met His Pro Ser Trp Ile Met Ile Ile Gly Ile Val Asn Ile
 50                  55                  60

Leu Ala Cys Thr Leu Ile Ser Phe Val Ile Tyr Pro Cys Phe Asp Phe
 65                  70                  75                  80

Gly Trp Asn Ser Pro Glu Ala Leu Tyr Leu Pro Pro Glu Pro Asp Thr
                    85                  90                  95

Pro Pro Gln Gln Pro Gln Ala His Ala Leu Pro Pro Leu Gln Pro Arg
                100                 105                 110

Pro Gln Tyr Met Pro Ile Leu Asp Tyr Glu Ala Glu Pro Gln Arg Pro
            115                 120                 125

Met Leu Pro Ala Ile Ser Tyr Phe Asn Leu Thr Gly Gly Asp Asp
130                 135                 140

<210> SEQ ID NO 26
<211> LENGTH: 135
<212> TYPE: PRT
<213> ORGANISM: chimpanzee C68 adenovirus protein

<400> SEQUENCE: 26

Met Thr Asp Pro Leu Ala Asn Asn Val Asn Asp Leu Leu Leu Asp
 1               5                  10                  15

Met Asp Gly Arg Ala Ser Glu Gln Arg Leu Ala Gln Leu Arg Ile Arg
                20                  25                  30

Gln Gln Gln Glu Arg Ala Val Lys Glu Leu Gln Asp Ala Val Ala Ile
            35                  40                  45

His Gln Cys Lys Arg Gly Ile Phe Cys Leu Val Lys Gln Ala Lys Ile
 50                  55                  60

Ser Tyr Glu Val Thr Pro Asn Asp His Arg Leu Ser Tyr Glu Leu Leu
 65                  70                  75                  80

Gln Gln Arg Gln Lys Phe Thr Cys Leu Val Gly Val Asn Pro Ile Val
                85                  90                  95

Ile Thr Gln Gln Ser Gly Asp Thr Lys Gly Cys Ile His Cys Ser Cys
                100                 105                 110

Asp Ser Pro Asp Cys Val His Thr Leu Ile Lys Thr Leu Cys Gly Leu
            115                 120                 125

Arg Asp Leu Leu Pro Met Asn
        130                 135

<210> SEQ ID NO 27
<211> LENGTH: 425
<212> TYPE: PRT
<213> ORGANISM: chimpanzee C68 adenovirus protein

<400> SEQUENCE: 27

Met Ser Lys Lys Arg Val Arg Val Asp Asp Phe Asp Pro Val Tyr
 1               5                  10                  15

Pro Tyr Asp Ala Asp Asn Ala Pro Thr Val Pro Phe Ile Asn Pro Pro
                20                  25                  30

Phe Val Ser Ser Asp Gly Phe Gln Glu Lys Pro Leu Gly Val Leu Ser
            35                  40                  45

Leu Arg Leu Ala Asp Pro Val Thr Thr Lys Asn Gly Glu Ile Thr Leu
 50                  55                  60

Lys Leu Gly Glu Gly Val Asp Leu Asp Ser Ser Gly Lys Leu Ile Ser
 65                  70                  75                  80
```

```
Asn Thr Ala Thr Lys Ala Ala Ala Pro Leu Ser Phe Ser Asn Asn Thr
                85                  90                  95

Ile Ser Leu Asn Met Asp His Pro Phe Tyr Thr Lys Asp Gly Lys Leu
            100                 105                 110

Ser Leu Gln Val Ser Pro Pro Leu Asn Ile Leu Arg Thr Ser Ile Leu
        115                 120                 125

Asn Thr Leu Ala Leu Gly Phe Gly Ser Gly Leu Gly Leu Arg Gly Ser
130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
            180                 185                 190

Gly Ala Ile Ala Thr Asn Ile Gly Asn Gly Leu Glu Phe Gly Ser Ser
        195                 200                 205

Ser Thr Glu Thr Gly Val Asp Asp Ala Tyr Pro Ile Gln Val Lys Leu
210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
        275                 280                 285

Gly Ser Gly Asn Leu Asn Pro Ile Thr Gly Thr Val Ser Ser Ala Gln
290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Thr Asn Ala Val Gly Phe Met Pro Asn Leu Lys Ala Tyr
            340                 345                 350

Pro Lys Ser Gln Ser Ser Thr Thr Lys Asn Asn Ile Val Gly Gln Val
        355                 360                 365

Tyr Met Asn Gly Asp Val Ser Lys Pro Met Leu Leu Thr Ile Thr Leu
370                 375                 380

Asn Gly Thr Asp Asp Ser Asn Ser Thr Tyr Ser Met Ser Phe Ser Tyr
385                 390                 395                 400

Thr Trp Thr Asn Gly Ser Tyr Val Gly Ala Thr Phe Gly Ala Asn Ser
                405                 410                 415

Tyr Thr Phe Ser Tyr Ile Ala Gln Glu
            420                 425

<210> SEQ ID NO 28
<211> LENGTH: 83
<212> TYPE: PRT
<213> ORGANISM: chimpanzee C68 adenovirus protein

<400> SEQUENCE: 28

Ile Thr Val Ile Pro Thr Thr Glu Asp Asn Pro Gln Leu Leu Ser Cys
1               5                   10                  15

Glu Val Gln Met Arg Glu Cys Pro Glu Gly Phe Ile Ser Leu Thr Asp
            20                  25                  30
```

```
Pro Arg Leu Ala Arg Ser Glu Thr Val Trp Asn Val Glu Thr Lys Ser
            35                  40                  45

Met Ser Ile Thr Asn Gly Ile Gln Met Phe Lys Ala Val Arg Gly Glu
 50                  55                  60

Arg Val Val Tyr Ser Met Ser Trp Glu Gly Gly Lys Ile Thr Ala
 65                  70                  75                  80

Arg Ile Leu

<210> SEQ ID NO 29
<211> LENGTH: 301
<212> TYPE: PRT
<213> ORGANISM: chimpanzee C68 adenovirus protein

<400> SEQUENCE: 29

Met Ser Glu Ser Asn Cys Ile Met Thr Arg Ser Arg Thr Arg Ser Ala
 1               5                  10                  15

Ala Ser Arg His His Pro Tyr Arg Pro Ala Pro Leu Pro Arg Cys Glu
            20                  25                  30

Glu Thr Glu Thr Arg Ala Ser Leu Val Glu Asp His Pro Val Leu Pro
            35                  40                  45

Asp Cys Asp Thr Leu Ser Met His Asn Val Ser Ser Val Arg Gly Leu
 50                  55                  60

Pro Cys Ser Ala Gly Phe Ala Val Leu Gln Glu Phe Pro Val Pro Trp
 65                  70                  75                  80

Asp Met Val Leu Thr Pro Glu Glu Leu Arg Val Leu Lys Arg Cys Met
            85                  90                  95

Ser Ile Cys Leu Cys Cys Ala Asn Ile Asp Leu Phe Ser Ser Gln Met
            100                 105                 110

Ile His Gly Tyr Glu Arg Trp Val Leu His Cys His Cys Arg Asp Pro
        115                 120                 125

Gly Ser Leu Arg Cys Met Ala Gly Gly Ala Val Leu Ala Leu Trp Phe
130                 135                 140

Arg Arg Ile Ile Arg Gly Cys Met Phe Asn Gln Arg Val Met Trp Tyr
145                 150                 155                 160

Arg Glu Val Val Asn Arg His Met Pro Lys Glu Ile Met Tyr Val Gly
                165                 170                 175

Ser Val Phe Trp Arg Gly His His Leu Ile Tyr Leu Arg Ile Trp Tyr
            180                 185                 190

Asp Gly His Val Gly Ser Ile Leu Pro Ala Met Ser Phe Gly Trp Ser
        195                 200                 205

Val Leu Asn Tyr Gly Leu Leu Asn Asn Leu Val Val Leu Cys Cys Thr
210                 215                 220

Tyr Cys Ser Asp Leu Ser Glu Ile Arg Met Arg Cys Cys Ala Arg Arg
225                 230                 235                 240

Thr Arg Arg Leu Met Leu Arg Ala Val Gly Ile Met Leu Arg Glu Ser
                245                 250                 255

Leu Asp Pro Asp Pro Leu Ser Ser Ser Leu Thr Glu Arg Arg Arg Gln
            260                 265                 270

Arg Leu Leu Arg Gly Leu Met Arg His His Arg Pro Ile Pro Phe Ala
        275                 280                 285

Asp Tyr Asp Ser His Arg Arg Ser Ser Ala Ser Ser Arg
        290                 295                 300

<210> SEQ ID NO 30
```

```
<211> LENGTH: 121
<212> TYPE: PRT
<213> ORGANISM: chimpanzee C68 adenovirus protein

<400> SEQUENCE: 30

Met Val Leu Pro Val Leu Pro Ser Pro Ala Val Thr Glu Thr Gln Gln
1               5                   10                  15

Asn Cys Ile Ile Trp Leu Gly Leu Ala His Ser Thr Val Val Asp Val
            20                  25                  30

Ile Arg Ala Ile Arg His Asp Gly Ile Phe Ile Thr Pro Glu Ala Leu
        35                  40                  45

Asp Leu Leu His Gly Leu Arg Glu Trp Leu Phe Tyr Asn Phe Asn Thr
    50                  55                  60

Glu Arg Ser Lys Arg Arg Asp Arg Arg Arg Ser Val Cys Ser Ala
65                  70                  75                  80

Arg Thr Arg Phe Cys Tyr Ser Lys Tyr Glu Asn Val Arg Lys Gln Leu
                85                  90                  95

His His Asp Thr Val Ala Asn Thr Ile Ser Arg Val Pro Pro Ser Pro
            100                 105                 110

Val Ser Ala Gly Pro Leu Thr Thr Leu
        115                 120

<210> SEQ ID NO 31
<211> LENGTH: 117
<212> TYPE: PRT
<213> ORGANISM: chimpanzee C68 adenovirus protein
<220> FEATURE:
<221> NAME/KEY: MISC_FEATURE
<222> LOCATION: (45)..(45)
<223> OTHER INFORMATION: Xaa can be any amino acid

<400> SEQUENCE: 31

Met Arg Val Cys Leu Arg Met Pro Val Glu Gly Ala Leu Arg Glu Leu
1               5                   10                  15

Phe Ile Met Ala Gly Leu Asp Leu Pro His Glu Leu Val Arg Ile Ile
            20                  25                  30

Gln Gly Trp Lys Asn Glu Asn Tyr Leu Gly Met Val Xaa Glu Cys Asn
        35                  40                  45

Met Met Ile Glu Glu Leu Glu Asn Pro Pro Ala Phe Ala Ile Val Leu
    50                  55                  60

Phe Leu Asp Val Arg Val Glu Ala Leu Leu Glu Ala Thr Val Glu His
65                  70                  75                  80

Leu Glu Asn Arg Ile Thr Phe Asp Leu Ala Val Ile Phe His Gln His
                85                  90                  95

Ser Gly Gly Glu Arg Cys His Leu Arg Asp Leu His Phe Glu Val Leu
            100                 105                 110

Arg Asp Arg Leu Asp
        115

<210> SEQ ID NO 32
<211> LENGTH: 129
<212> TYPE: PRT
<213> ORGANISM: chimpanzee C68 adenovirus protein

<400> SEQUENCE: 32

Met Leu Glu Arg Thr Ala Cys Ile Tyr Phe Ile Val Val Pro Glu Ala
1               5                   10                  15

Leu Asn Val His Leu Glu Asp Phe Ser Phe Val Asp Phe Leu Lys Asn
            20                  25                  30
```

```
Cys Leu Gly Asp Phe Leu Ser Ser Tyr Leu Glu Asp Ile Thr Gly Ser
             35                  40                  45

Ser Gln His Ala Tyr Ser Ser Leu Ala Phe Gly Asn Ala His Trp Gly
         50                  55                  60

Gly Leu Arg Phe Ile Cys Thr Val Ala Cys Pro Asn Leu Ile Pro Gly
 65                  70                  75                  80

Gly Pro Met Ala Lys Asn Phe Gly Glu Asp Met Lys Glu Tyr Leu Gln
                 85                  90                  95

Leu Leu Leu Arg Glu Glu Leu Arg Asp Arg Gly Arg Asp Phe Asp Ile
            100                 105                 110

Pro Leu Val Asn Leu Leu Gln Val Asn Gln Glu Gln Asn Ile Leu Glu
            115                 120                 125

Leu

<210> SEQ ID NO 33
<211> LENGTH: 36521
<212> TYPE: DNA
<213> ORGANISM: chimpanzee C68 adenovirus
<220> FEATURE:
<221> NAME/KEY: misc_feature
<222> LOCATION: (8268)..(8268)
<223> OTHER INFORMATION: can be a or c or g or t
<220> FEATURE:
<221> NAME/KEY: misc_feature
<222> LOCATION: (8322)..(8322)
<223> OTHER INFORMATION: can be a or c or g or t
<220> FEATURE:
<221> NAME/KEY: misc_feature
<222> LOCATION: (8535)..(8535)
<223> OTHER INFORMATION: can be a or c or g or t
<220> FEATURE:
<221> NAME/KEY: misc_feature
<222> LOCATION: (16753)..(16753)
<223> OTHER INFORMATION: can be a or c or g or t
<220> FEATURE:
<221> NAME/KEY: misc_feature
<222> LOCATION: (28095)..(28095)
<223> OTHER INFORMATION: can be a or c or g or t
<220> FEATURE:
<221> NAME/KEY: misc_feature
<222> LOCATION: (29373)..(29373)
<223> OTHER INFORMATION: can be a or c or g or t
<220> FEATURE:
<221> NAME/KEY: misc_feature
<222> LOCATION: (30447)..(30447)
<223> OTHER INFORMATION: can be a or c or g or t
<220> FEATURE:
<221> NAME/KEY: misc_feature
<222> LOCATION: (31015)..(31015)
<223> OTHER INFORMATION: can be a or c or g or t

<400> SEQUENCE: 33
ccttcttcaa taatatacct tcaaactttt tgtgcgcgtt aatatgcaaa tgaggcgttt      60
gaatttgggg aggaagggcg gtgattggtc gagggatgag cgaccgttag gggcggggcg    120
agtgacgttt tgatgacgtg gttgcgagga ggagccagtt tgcaagttct cgtgggaaaa    180
gtgacgtcaa acgaggtgtg gtttgaacac ggaaatactc aatttcccg cgctctctga     240 caggaaatga ggtgtttctg gcggatgca agtgaaaacg ggccatttc gcgcgaaaac      300 tgaatgagga agtgaaaatc tgagtaattt cgcgtttatg gcagggagga gtatttgccg    360
agggccgagt agactttgac cgatcacgtg ggggttcga ttaccgtgtt tttcacctaa     420
atttccgcgt acggtgtcaa agtccggtgt ttttacgtag gtgtcagctg atcgccaggg    480
tatttaaacc tgcgctctcc agtcaagagg ccactcttga gtgccagcga gaagagtttt    540
```

```
ctcctccgcg ccgcgagtca gatctacact ttgaaagatg aggcacctga gagacctgcc    600
cgatgagaaa atcatcatcg cttccgggaa cgagattctg gaactggtgg taaatgccat    660
gatgggcgac gaccctccgg agccccccac cccatttgag acaccttcgc tgcacgattt    720
gtatgatctg gaggtggatg tgcccgagga cgatcccaat gaggaggcgg taaatgattt    780
ttttagcgat gccgcgctgc tagctgccga ggaggcttcg agctctagct cagacagcga    840
ctcttcactg cataccccta gacccggcag aggtgagaaa aagatccccg agcttaaagg    900
ggaagagatg gacttgcgct gctatgagga atgcttgccc ccgagcgatg atgaggacga    960
gcaggcgatc cagaacgcag cgagccaggg agtgcaagcc gccagcgaga ctttgcgct   1020
ggactgcccg cctctgcccg acacggctg taagtcttgt gaatttcatc gcatgaatac   1080
tggagataaa gctgtgttgt gtgcactttg ctatatgaga gcttacaacc attgtgttta   1140
cagtaagtgt gattaagttg aactttagag ggaggcagag agcagggtga ctgggcgatg   1200
actggtttat ttatgtatat atgttcttta tataggcccc gtctctgacg cagatgatga   1260
gaccccccact acaaagtcca cttcgtcacc cccagaaatt ggcacatctc cacctgagaa   1320
tattgttaga ccagttcctg ttagagccac tgggaggaga gcagctgtgg aatgtttgga   1380
tgacttgcta cagggtgggg ttgaaccttt ggacttgtgt acccggaaac gccccaggca   1440
ctaagtgcca cacatgtgtg tttacttgag gtgatgtcag tatttatagg gtgtggagtg   1500
caataaaaaa tgtgttgact ttaagtgcgt ggtttatgac tcaggggtgg ggactgtgag   1560
tatataagca ggtgcagacc tgtgtggtta gctcagagcg gcatggagat ttggacggtc   1620
ttggaagact ttcacaagac tagacagctg ctagagaacg cctcgaacgg agtctcttac   1680
ctgtggagat tctgcttcgg tggcgaccta gctaggctag tctacagggc caaacaggat   1740
tatagtgaac aatttgaggt tattttgaga gagtgttctg gtcttttga cgctcttaac   1800
ttgggccatc agtctcactt taaccagagg atttcgagag cccttgattt tactactcct   1860
ggcagaacca ctgcagcagt agccttttt gctttattc ttgacaaatg gagtcaagaa   1920
acccatttca gcagggatta ccagctggat ttcttagcag tagctttgtg agaacatgg   1980
aagtgccagc gcctgaatgc aatctccggc tacttgccgg tacagccgct agacactctg   2040
aggatcctga atctccagga gagtcccagg gcacgccaac gtcgccagca gcagcagcag   2100
gaggaggatc aagaagagaa cccgagagcc ggcctggacc ctccggcgga ggaggaggag   2160
tagctgacct gtttcctgaa ctgcgccggg tgctgactag gtcttcgagt ggtcgggaga   2220
gggggattaa gcgggagagg catgatgaga ctaatcacag aactgaactg actgtgggtc   2280
tgatgagtcg caagcgccca gaaacagtgt ggtggcatga ggtgcagtcg actggcacag   2340
atgaggtgtc ggtgatgcat gagaggtttt ctctagaaca agtcaagact tgttggttag   2400
agcctgagga tgattgggag gtagccatca ggaattatgc caagctggct ctgaggccag   2460
acaagaagta caagattact aagctgataa atatcagaaa tgcctgctac atctcaggga   2520
atggggctga agtggagatc tgtctccagg aaagggtggc tttcagatgc tgcatgatga   2580
atatgtaccc gggagtggtg ggcatggatg gggttacctt tatgaacatg aggttcaggg   2640
gagatgggta taatggcacg gtctttatgg ccaataccaa gctgacagtc catggctgct   2700
ccttctttgg gttaataac acctgcatcg aggcctgggg tcaggtcggt gtgagggct   2760
gcagtttttc agccaactgg atggggtcg tgggcaggac caagagtatg ctgtccgtga   2820
agaaatgctt gtttgagagg tgccacctgg gggtgatgag cgagggcgaa gccagaatcc   2880
gccactgcgc ctctaccgag acgggctgct ttgtgctgtg caagggcaat gctaagatca   2940
```

```
agcataatat gatctgtgga gcctcggacg agcgcggcta ccagatgctg acctgcgccg    3000
gcgggaacag ccatatgctg gccaccgtac atgtggcttc ccatgctcgc aagccctggc    3060
ccgagttcga gcacaatgtc atgaccaggt gcaatatgca tctggggtcc cgccgaggca    3120
tgttcatgcc ctaccagtgc aacctgaatt atgtgaaggt gctgctggag cccgatgcca    3180
tgtccagagt gagcctgacg ggggtgtttg acatgaatgt ggaggtgtgg aagattctga    3240
gatatgatga atccaagacc aggtgccgag cctgcgagtg cggagggaag catgccaggt    3300
tccagcccgt gtgtgtggat gtgacggagg acctgcgacc cgatcatttg gtgttgccct    3360
gcaccgggac ggagttcggt tccagcgggg aagaatctga ctagagtgag tagtgttctg    3420
gggcggggga ggacctgcat gagggccaga taactgaaaa tctgtgcttt tctgtgtgtt    3480
gcagcagcat gagcggaagc ggctcctttg agggaggggt attcagccct tatctgacgg    3540
ggcgtctccc ctcctgggcg ggagtgcgtc agaatgtgat gggatccacg gtggacggcc    3600
ggcccgtgca gcccgcgaac tcttcaaccc tgacctatgc aaccctgagc tcttcgtcgt    3660
tggacgcagc tgccgccgca gctgctgcat ctgccgccag cgccgtgcgc ggaatggcca    3720
tgggcgccgg ctactacggc actctggtgg ccaactcgag ttccaccaat aatcccgcca    3780
gcctgaacga ggagaagctg ttgctgctga tggcccagct cgaggccttg acccagcgcc    3840
tgggcgagct gacccagcag gtggctcagc tgcaggagca gacgcgggcc gcggttgcca    3900
cggtgaaatc caaataaaaa atgaatcaat aaataaacgg agacggttgt tgattttaac    3960
acagagtctg aatctttatt tgattttttcg cgcgcggtag gccctggacc accggtctcg    4020
atcattgagc acccgtggaa tcttttccag gacccggtag aggtgggctt ggatgttgag    4080
gtacatgggc atgagcccgt cccgggggtg gaggtagctc cattgcaggg cctcgtgctc    4140
gggggtggtg ttgtaaatca cccagtcata gcagggcgc agggcatggt gttgcacaat    4200
atctttgagg aggagactga tggccacggg cagcccttg gtgtaggtgt ttacaaatct    4260
gttgagctgg gagggatgca tgcggggga gatgaggtgc atcttggcct ggatcttgag    4320
attggcgatg ttaccgccca gatcccgcct ggggttcatg ttgtgcagga ccaccagcac    4380
ggtgtatccg gtgcacttgg ggaatttatc atgcaacttg aagggaagg cgtgaaagaa    4440
tttggcgacg cctttgtgcc cgcccaggtt ttccatgcac tcatccatga tgatggcgat    4500
gggcccgtgg gcggcggcct gggcaaagac gtttcggggg tcggacacat catagttgtg    4560
gtcctgggtg aggtcatcat aggccatttt aatgaatttg ggcggagg tgccggactg    4620
ggggacaaag gtaccctcga tcccgggggc gtagttcccc tcacagatct gcatctccca    4680
ggctttgagc tcgaggggg gatcatgtc cacctgcggg gcgataaaga acacggtttc    4740
cggggcgggg gagatgagct gggccgaaag caagttccgg agcagctggg acttgccgca    4800
gccggtgggg ccgtagatga ccccgatgac cggctgcagg tggtagttga gggagagaca    4860
gctgccgtcc tcccggagga ggggggccac ctcgttcatc atctcgcgca cgtgcatgtt    4920
ctcgcgcacc agttccgcca ggaggcgctc tcccccagg ataggagct cctgagcga    4980
ggcgaagttt ttcagcggct tgagtccgtc ggccatgggc attttggaga gggtttgttg    5040
caagagttcc aggcggtccc agagctcggt gatgtgctct acggcatctc gatccagcag    5100
acctcctcgt ttcgcgggtt gggacggctg cgggagtatg gcaccagacg atgggcgtcc    5160
agcgcagcca gggtccggtc cttccagggt cgcagcgtcc cgtcagggt ggtctccgtc    5220
acggtgaagg ggtgcgcgcc gggctgggcg cttgcgaggg tgcgcttcag gctcatccgg    5280
```

```
ctggtcgaaa accgctcccg atcggcgccc tgcgcgtcgg ccaggtagca attgaccatg    5340
agttcgtagt tgagcgcctc ggccgcgtgg cctttggcgc ggagcttacc tttggaagtc    5400
tgcccgcagg cgggacagag gagggacttg agggcgtaga gcttgggggc gaggaagacg    5460
gactcggggg cgtaggcgtc cgcgccgcag tgggcgcaga cggtctcgca ctccacgagc    5520
caggtgaggt cgggctggtc ggggtcaaaa accagtttcc cgccgttctt tttgatgcgt    5580
ttcttacctt tggtctccat gagctcgtgt ctccgctggg tgacaaagag ctgtccgtgt    5640
ccccgtagac cgactttatg ggccggtcct cgagcggtgt gccgcggtcc tcctcgtaga    5700
ggaaccccgc ccactccgag acgaaagccc gggtccaggc cagcacgaaw gaggccacgt    5760
gggacgggta tcggtcgttg tccaccagcg ggtccacctt ttccagggta tgcaaacaca    5820
tgtccccctc gtccacatcc aggaaggtga ttggcttgta agtgtakgcc acgtgaccgg    5880
gggtcccggc cggggggta taaaaggggtg cgggtccctg ctcgtcctca ctgtcttccg    5940
gatcgctgtc cacgagcgcc agctgttggg gtaggtattc cctctcgaag gcgggcatga    6000
cctcggcact caggttgtca gtttctagaa acgaggagga tttgatattg acggtgccgg    6060
cggagatgcc tttcaagagc ccctcgtcca tctggtcaga aaagacgatc ttttttgttgt    6120
cgagcttggt ggcgaaggag ccgtakaggg cgttggagag gagcttggcg atggagcgca    6180
tggtctggtt tttttccttg tcggcgcgct ccttggcggc gatgttgagc tgcacgtact    6240
cgcgcgccac gcacttccat tcggggaaga cgtggtcagc tcgtcgggca cgattctgac    6300
ctgccagccc cgattatgca gggtgatgag gtccacactg gtggccacct cgccgcgcag    6360
gggctcatta ktccagcaga ggcgtccgcc cttgcgcgag cagaaggggg gcaggggggtc    6420
cagcatgacc tcgtcggggg ggtcggcatc gatggtgaag atgccgggca ggaggtcggg    6480
gtcaaagtag ctgatggaag tggccagatc gtccagggca gcttgccatt cgcgcacggc    6540
cagcgcgcgc tcgtagggac tgaggggcgt gccccagggc atgggatggg taagcgcgga    6600
ggcgtacatg ccgcagatgt cgtagacgta gaggggctcc tcgaggatgc cgatgtaggt    6660
ggggtagcag cgcccccccgc ggatgctggc gcgcacgtag tcatacagct cgtgcgaggg    6720
ggcgaggagc cccgggccca ggttggtgcg actgggcttt tcggcgcggt agacgatctg    6780
gcggaaaatg gcatgcgagt tggaggagat ggtgggcctt tggaagatgt tgaagtgggc    6840
gtggggcagt ccgaccgagt cgcggatgaa gtgggcgtag gagtcttgca gcttggcgac    6900
gagctcggcg gtgactagga cgtccagagc gcagtagtcg agggtctcct ggatgatgtc    6960
atacttgagc tgtcccttttt gtttccacag ctcgcggttg agaaggaact cttcgcggtc    7020
cttccagtac tcttcgaggg ggaacccgtc ctgatctgca cggtaagagc ctagcatgta    7080
gaactggttg acggccttgt aggcgcagca gccyttctcc acggggargg cgtaggcctg    7140
ggcggccttg cgcagggagg tgtgcgtgag ggcgaaagtg tccctgacca tgaccttgag    7200
gaactggtgc ttgaagtcga tattgtcgca gccccccctgc tcccagagct ggaagtccgt    7260
gcgcttcttg taggcggggt tgggcaaagc gaaagtaaca tcgttgaaga ggatcttgcc    7320
cgcgcggggc ataaagttgc gagtgatgcg gaaaggttgg ggcacctcgg cccggttgtt    7380
gatgacctgg gcggcgagca cgatctcgtc gaagccgttg atgttgtggc ccacgatgta    7440
gagttccacg aatcgcggac ggcccttgac gtgggggcagt ttcttgagct cctcgtaggt    7500
gagctcgtcg gggtcgctga gcccgtgctg ctcgagcgcc cagtcggcga gatgggggtt    7560
ggcgcggagg aaggaagtcc agagatccac ggccagggcg gtttgcagac ggtcccggta    7620
ctgacggaac tgctgcccga cggccatttt ttcgggggtg acgcagtaga aggtgcgggg    7680
```

```
gtccccgtgc cagcgatccc atttgagctg gagggcgaga tcgagggcga gctcgacgag   7740
ccggtcgtcc ccggagagtt tcatgaccag catgaagggg acgagctgct tgccgaagga   7800
ccccatccag gtgtaggttt ccacatcgta ggtgaggaag agcctttcgg tgcgaggatg   7860
cgagccgatg gggaagaact ggatctcctg ccaccaattg gaggaatggc tgttgatgtg   7920
atggaagtag aaatgccgac ggcgcgccga acactcgtgc ttgtgtttat acaagcggcc   7980
acagtgctcg caacgctgca cgggatgcac gtgctgcacg agctgtacct gagttccttt   8040
gacgaggaat tcagtggga agtggagtcg tggcgcctgc atctcgtgct gtactacgtc   8100
gtggtggtcg gcctggccct cttctgcctc gatggtggtc atgctgacga gcccgcgcgg   8160
gaggcaggtc cagacctcgg cgcgagcggg tcggagagcg aagacgaagg cgcgcaggcc   8220
ggagctgtcc agggtcctga gacgctgcgg agtcaggtca gtgggcancg cggcgcgcg   8280
gttgacttgc argagttttt ccagggcgcg cggaggtcc anatggtact tgatctccac   8340
cgcgccattg gtggcgaact ccatggcttg cagggtcccg tgccctgggg gtgtgaccac   8400
cgtcccccgt ttcttcttgg gcggctgggg cgacgggggc ggtgcctctt ccatggttag   8460
aascggcggc gaagacgcgc gccgggcggc aggggcggct cggggcccgg atgcaggggc   8520
ggcaggggca cttcngcgcc gcgcgcgggt aggttctggt actgcgcccg gagaaaactg   8580
gcgtgagcga cgacgcgacg gttgacgtcc tggatctgac gcctctgggt gaaggccacg   8640
ggacccgtga gtttgaacct gaaagaaagt tcgacagaat caatctcggt atcgttgacg   8700
gcggcctgcc gcaagatctc ttgcacgtcc cccgagttgt cctggtatgc gatctcggtc   8760
atgaactgct cgatctcctc ctcttgaagg tctccgcggc cggcgcgctc cacggtggcc   8820
gcgaagtcgt tggagatgcg gcccatgagc tgcgagaagg cgttcatgcc cgcctcgttc   8880
cagacgcggc tgtagaccac gacgccctcg ggatcgcggg cgcgcatgac cacctgggcg   8940
aggttgagct ccacgtggcg cgtgaagacc gcgtagttgc agaggcgctg gtagaggtag   9000
ttgagcgtgg tggcgatgtg ctcggtgacr aagaaataca tgatccagcg gcggagcggc   9060
atctcgctga cgtcgcccag cgcctccaaa cgttccatgg cctcgtaaaa gtccacggcg   9120
aagttgaaaa actgggagtt gcgcgccgag acggtcaact cctcctccag aagacggatg   9180
agctcggcga tggtggcgcg cacctcgcgc tcgaaggccc ccgggagttc ctccacttcc   9240
tcttcttcct cctccactaa catctcttct acttcctcct caggcggcag tggtggcggg   9300
ggaggggggc tgcgtcgccg gcggcgcacg ggcagacggt cgatgaagcg ctcgatggtc   9360
tcgccgcgcc ggcgtcgcat ggtctcggtg acggcgcgcc cgtcctcgcg gggccgcakc   9420
gtgaagacgc cgccgcgcat ctccaggtgg ccggggggg ccccgttgg gcagggagag   9480
ggcgctgacg atgcatctta tcaattgccc cgtagggact ccgcgcaagg acctgagcgt   9540
ctcgagatcc acgggatctg aaaaccgctg aacgaaggct tcgaagccag tcgcagtcgc   9600
aaggtakgct gagcacggtt tcttctggcg ggtcatgttg gttgggagcg gggcgggcga   9660
tgctgctggt gatgaagttg aaataggcgg ttctgagacg gcggatggtg gcgargagca   9720
ccaggtcttt gggcccggct tgctggatgc gcagacggtc ggccatgccc caggcgtggt   9780
cctgacacct ggccaggtcc ttgtagtagt cctgcatgag ccgctccaac gggcacctcc   9840
tcctcgcccg cgcggccgtg catgcgcgtg agcccgaagc cgcgctgggg ctggacgagc   9900
gccaggtcgg cgacgacgcg ctcggcgagg atgcttgct ggatctgggt gagggtggtc   9960
tggaagtcat caaagtcgac gaagcggtgg taggctccgg tgttgatggt gtaggagcag  10020
```

```
ttggccatga cggaccagtt gacggtctgg tgggccggac gcacgagctc gtggtacttg    10080
aggcgcgagt aggcgcgcgt gtcgaagatg tagtcgttgc aggtgcgcac caggtactgg    10140
tagccgatga ggaagtgcgg cggcggctgg cggtagagcg gccatcgctc ggtggcgggg    10200
gcgccgggcg cgaggtcctc gagcatggtg cggtggtagc cgtagatgta cctggacatc    10260
caggtgatgc cggcggcggt ggtggaggcg cgcgggaact cgcggacgcg ttccagatgt    10320
tgcgcagcgg caggaagtag ttcatggtgg gcacggtctg gcccgtgagg cgcgcgcagt    10380
cgtggatgct ctatacgggc aaaaacgaaa gcggtcagcg gctcgactcc gtggcctgga    10440
ggctaagcga acgggttggg ctgcgcgtgt accccggttc gaatctcgaa tcaggctgga    10500
gccgcagcta acgtggtatt ggcactcccg tctmgaccca agcbtgcacc aaccctccag    10560
gatacgagg cgggtcgttt tgcaactttt ttttggaggc cggatgagac tagtaagcgc    10620
ggaaagcggc cgaccgcgat ggctcgtctg ccgtagtctg gagaagaatc gccagggttg    10680
cgttgcggtg tgcccggtt cgaggccggc cggattccgc ggctaacgag ggcgtggctg    10740
ccccgtcgtt tccaagaccc catagccagc cgacttctcc agttacggag cgagcccctc    10800
ttttgttttg tttgttttg ccagatgcat cccgtactgc ggcagatgcg cccccaccac    10860
cctccaccgc aacaacagcc ccctccacag ccggcgcttc tgccccgcc ccagcagcaa    10920
cttccagcca cgaccgccgc ggccgccgtg agcggggctg gacagagtta tgatcaccag    10980
ctggccttgg aagagggcga ggggctggcg cgcctggggg cgtcgtcgcc ggagcggcac    11040
ccgcgcgtgc agatgaaaag ggacgctcgc gaggcatacg tgcccaagca gaacctgttc    11100
agagacagga gcggcgagga gcccgaggag atgcgcgcgg cccggttcca cgcggggcgg    11160
gagctgcggc gcggcctgga ccgaaagagg gtgctgaggg acgaggattt cgaggcggac    11220
gagctgacgg ggatcagccc cgcgcgcgcg cacgtggccg cggccaacct ggtcacggcg    11280
tacgagcaga ccgtgaagga ggagagcaac ttccaaaaat ccttcaacaa ccacgtgcgc    11340
accctgatcg cgcgcgagga ggtgaccctg ggcctgatgc acctgtggga cctgctggag    11400
gccatcgtgc agaaccccac cagcaagccg ctgacggcgc agctgttcct ggtggtgcag    11460
catagtcggg acaacgaagc gttcagggag gcgctgctga atatcaccga gcccgagggc    11520
cgctggctcc tggaccctggt gaacattctg cagagcatcg tggtgcagga gcgcgggctg    11580
ccgctgtccg agaagctggc ggccatcaac ttctcggtgc tgagtttggg caagtactac    11640
gctaggaaga tctacaagac cccgtacgtg cccatagaca aggaggtgaa gatcgacggg    11700
ttttacatgc gcatgaccct gaaagtgctg accctgagcg acgatctggg ggtgtaccgc    11760
aacgacagga tgcaccgtgc ggtgagcgcc agcaggcggc gcgagctgag cgaccaggag    11820
ctgatgcata gtctgcagcg ggccctgacc ggggccggga ccgagggga gagctacttt    11880
gacatgggcg cggacctgca ctggcagccc agccgccggg ccttggaggc ggcggcagga    11940
ccctacgtag aagaggtgga cgatgaggtg gacgaggagg gcgagtacct ggaagactga    12000
tggcgcgacc gtatttttgc tagatgcaac aacaacagcc acctcctgat cccgcgatgc    12060
gggcggcgct gcagagccag ccgtccggca ttaactcctc ggacgattgg acccaggcca    12120
tgcaacgcat catggcgctg acgacccgca accccgaagc ctttagacag cagccccagg    12180
ccaaccggct ctcggccatc ctggaggccg tggtgccctc gcgctccaac cccacgcacg    12240
agaaggtcct ggccatcgtg aacgcgctgg tggagaacaa ggccatccgc ggcgacgagg    12300
ccggcctggt gtacaacgcg ctgctggagc gcgtggcccg ctacaacagc accaacgtgc    12360
agaccaacct ggaccgcatg gtgaccgacg tgcgcgaggc cgtggcccag cgcgagcggt    12420
```

```
tccaccgcga gtccaacctg ggatccatgg tggcgctgaa cgccttcctc agcacccagc    12480
ccgccaacgt gccccggggc caggaggact acaccaactt catcagcgcc ctgcgcctga    12540
tggtgaccga ggtgccccag agcgaggtgt accagtccgg gccggactac ttcttccaga    12600
ccagtcgcca gggcttgcag accgtgaacc tgagccaggc tttcaagaac ttgcagggcc    12660
tgtggggcgt gcaggccccg gtcggggacc gcgcgacggt gtcgagcctg ctgacgccga    12720
actcgcgcct gctgctgctg ctggtggccc ccttcacgga cagcggcagc atcaaccgca    12780
actcgtacct gggctacctg attaacctgt accgcgaggc catcggccag gcgcacgtgg    12840
acgagcagac ctaccaggag atcacccacg tgagccgcgc cctgggccag gacgacccgg    12900
gcaacctgga agccaccctg aacttttttgc tgaccaaccg gtcgcagaag atcccgcccc    12960
agtacgcgct cagcaccgag gaggagcgca tcctgcgtta cgtgcagcag aagcgtgggc    13020
ctgttcctga tgcaggaggg ggccacccccc agcgccgcgc tcgacatgac cgcgcgcaac    13080
atggtagccc atcatgtacg ccagcaaccg cccgttcatc aataaactga tggactactt    13140
gcatcgggcg gccgccatga actctgacta tttcaccaac gccatcctga tccccactg    13200 gctcccgccg ccgggggttct acacgggcga gtacgacatg cccgacccca tgacgggtt    13260 cctgtgggac gatgtggaca gcagcgtgtt ctccccccga ccgggtgcta acgagcgccc    13320
cttgtggaag aaggaaggca gcgaccgacg cccgtcctcg gcgctgtccg gccgcgaggg    13380
tgctgccgcg gcggtgcccg aggccgccag tcctttcccg agcttgccct tctcgctgaa    13440
cagtatccgc agcagcgagc tgggcaggat cacgcgcccg cgcttgctgg gcgaagagga    13500
gtacttgaat gactcgctgt tgagacccga gcgggagaag aacttcccca ataacgggat    13560
agaaagcctg gtggacaaga tgagccgctg gaagacgtat gcgcaggagc acagggacga    13620
tccccgggcg tcgcaggggg ccacgagccg gggcagcgcc gcccgtaaac gccggtggca    13680
cgacaggcag cggggacaga tgtgggacga tgaggactcc gccgacgaca gcagcgtgtt    13740
ggacttgggt gggagtggta acccgttcgc tcacctgcgc ccccgtatcg ggcgcatgat    13800
gtaagagaaa ccgaaaataa atgatactca ccaaggccat ggcgaccagc gtgcgttcgt    13860
ttcttctctg ttgttgttgt atctagtatg atgaggcgtg cgtacccgga gggtcctcct    13920
ccctcgtacg agagcgtgat gcagcaggcg atggcggcgg cggcgatgca gcccccgctg    13980
gaggctcctt acgtgccccc gcggtacctg gcgcctacgg aggggcggaa cagcattcgt    14040
tactcggagc tggcaccctt gtacgatacc cccggttgt acctggtgga caacaagtcg    14100
gcggacatcg cctcgctgaa ctaccagaac gaccacagca cttcctgac caccgtggtg    14160 cagaacaatg acttcacccc cacggaggcc agcacccaga ccatcaactt tgacgagcgc    14220
tcgcggtggg gcggccagct gaaaaccatc atgcacacca acatgcccaa cgtgaacgag    14280
ttcatgtaca gcaacaagtt caaggcgcgg gtgatggtct cccgcaagac ccccaatggg    14340
gtgacagtga cagaggatta tgatggtagt caggatgagc tgaagtatga atgggtggaa    14400
tttgagctgc ccgaaggcaa cttctcggtg accatgacca tcgacctgat gaacaacgcc    14460
atcatcgaca attacttggc ggtggggcgg cagaacgggg tgctggagag cgacatcggc    14520
gtgaagttcg acactaggaa cttcaggctg ggctgggacc ccgtgaccga gctggtcatg    14580
cccggggtgt acaccaacga ggctttccat ccgatattg tcttgctgcc cggctgcggg    14640
gtggacttca ccgagagccg cctcagcaac ctgctgggca ttcgcaagag gcagcccttc    14700
caggaaggct tccagatcat gtacgaggat ctggaggggg gcaacatccc cgcgctcctg    14760
```

```
gatgtcgacg cctatgagaa aagcaaggag gatgccagcag ctgaagcaac tgcagccgta   14820
gctaccgcct ctaccgaggt caggggcgat aattttgcaa cgccgcagc agtggcagcg    14880
gccgaggcgg ctgaaaccga aagtaagata gtcattcagc cggtggagaa ggatagcaag   14940
aacaggagct acaacgtact accggacaag ataaacaccg cctaccgcag ctggtaccta   15000
gcctacaact atggcgaccc cgagaagggc gtgcgctcct ggacgctgct caccacctcg   15060
gacgtcacct gcggcgtgga gcaagtctac tggtcgctgc ccgacatgat gcaagacccg   15120
gtcaccttcc gctccacgcg tcaagttagc aactacccgg tggtgggcgc cgagctcctg   15180
cccgtctact ccaagagctt cttcaacgag caggccgtct actcgcagca gctgcgcgcc   15240
ttcacctcgc ttacgcacgt cttcaaccgc ttccccgaga accagatcct cgtccgcccg   15300
cccgcgccca ccattaccac cgtcagtgaa aacgttcctg ctctcacaga tcacgggacc   15360
ctgccgctgc gcagcagtat ccggggagtc cagcgcgtga ccgttactga cgccagacgc   15420
cgcacctgcc cctacgtcta caaggccctg ggcatagtcg cgccgcgcgt cctctcgagc   15480
cgcaccttct aaatgtccat tctcatctcg cccagtaata acaccggttg gggcctgcgc   15540
gcgcccagca agatgtacgg aggcgctcgc caacgctcca cgcaacaccc cgtgcgcgtg   15600
cgcgggcact tccgcgctcc ctggggcgcc ctcaaaggcc gcgtgcggtc gcgcaccacc   15660
gtcgacgacg tgatcgacca ggtggtggcs gacgcgcgcg amtacacccc cgccgcggcc   15720
cctgttttcca cygtggacgc cgtcatcgac agcgtggtgg cggacgcgcg ccggtacgcc   15780
cgcgccaaga gccggcggcg gcgcatcgcc cggcggcacc ggagcacccc cgccatgcgc   15840
gcggcgcgga gccttgttgc gcagggccag gcgcacggga cgcagggcca tgttcagggc   15900
ggccagacgc gcggcttcag gcgccagcgc cggcaggacc cggagacgcg cggccacggc   15960
ggcggcagcg gccatcgcca gcatgtcccg cccgcggcga gggaacgtgt actgggtgcg   16020
cgacgccgcc accggtgtgc gcgtgcccgt gcgcacccgc cccctcgca cttgaagatg    16080
ttcacttcgc gatgttgatg tgtcccagcg gcgaggagga tgtccaagcg caaattcaag   16140
gaagagatgc tccaggtcat cgcgcctgag atatacggcc ctgcggtggt gaaggaggaa   16200
agaaagcccc gcaaaatcaa gcgggtcaaa aaggacaaaa aggaagaaga aagtgatgtg   16260
gacggattgg tggagtttgt gcgcgagttc gcccccgcc ggcgcgtgca gtggcgcggg    16320
cggaaggtgc aaccggtgct gagacccggc accaccgtgg tcttcacgcc cggcgagcgc   16380
tccggcaccg cttccaagcg ctcctacgac gaggtgtacg gggatgatga tattctggag   16440
caggcggccg akcgcctggg cgagtttgct tacggcaagc gcagccgttc cgcaccgaag   16500
gaagaggcgg tgtccatccc gctggaccac ggcaaccca cgccgagcct caagcccgtg    16560
accttgcagc aggtgctgcc gaccgcgcg ccgcgccggg ggttcaagcg cgagggcgag    16620
gatctgtacc ccaccatgca gctgatggtg cccaagcgcc agaaghtgga agacgtgctg   16680
gagaccatga aggtggaccc ggacgtgcag cccgaggtca aggtgcggcc catcaagcag   16740
gtggccccgg gcntgggcgt gcagaccgtg gacatcwaga ttcccacgga gcccatggaa   16800
acgcagaccg agcccatgat caagcccagc accagcacca tggaggtgca gacggatccc   16860
tggatgccat cggctcctag tcgaagaccc cggcgcaagt acggcgcggc cagcctgctg   16920
atgcccaact acgcgctgca tccttccatc atccccacgc cgggctaccg cggcacgcgc   16980
ttctaccgcg gtcataccag cagccgccgc cgcaagacca ccactcgccg ctcgccgtcg   17040
ccgcaccgcc gctgcaacca cccctgccgc cctggtgcgg agagtgtacc gccgcggccg   17100
cgcacctctg accctgccgc gcgcgcgcta ccacccgagc atcgccattt aaactttcgc   17160
```

```
cagctttgca gatcaatggc cctcacatga ccgccttcgc gttcccatta cgggctaccg    17220
aggaagaaaa ccgcgccgta aaggctggc ggggaacggg atgcgtcgcc accaccacg      17280 gcggcggcgc gccatcagca agcggttggg gggaggcttc ctgcccgcgc tgatccccat    17340
catcgccgcg gcgatcgggg cgatccccgg cattgcttcc gtggcggtgc aggcctctca    17400
gcgccactga gacacacttg gaaacatctt gtaatagacc ratggactct gacgctcctg    17460
gtcctgtgat gtgttttcgt agacagatgg aagacatcaa ttttcgtcc ctggctccgc     17520 gacacggcac gcggccgttc atgggcacct ggagcgacat cggcaccagc caactgaacg    17580
ggggcgcctt caattggagc agtctctgga gcgggcttaa gaatttcggg tccacgctta    17640
aaacctatgg cagcaaggcg tggaacagca ccacagggca ggcgctgagg ataagctga    17700 aagagcagaa cttccagcag aaggtggtcg atgggctcgc ctcgggcatc aacggggtgg    17760
tggacctggc caaccaggcc gtgcagcggc agatcaacag ccgcctggac ccggtgccgc    17820
ccgccggctc cgtggagatg ccgcaggtgg aggaggagct gcctcccctg dacaagcggg    17880
gcgagaagcg accccgcccc gatgcggagg agacgctgct gacgcacacg gacgagccgc    17940
ccccgtacga ggaggcggtg aaactgggtc tgcccaccac gcggcccatc gcgcccctgg    18000
ccaccggggt gctgaaaccc gaaaagcccg cgaccctgga cttgcytcct ccccagcctt    18060
cccgcccatv tacagtggct aagccctgc cgccggtggc cgtggcccgc gcgcgacccg     18120
ggggcaccgc ccgccctcat gcgaactggc agagcactct gaacagcatc gtgggtctgg    18180
gagtgcagag tgtgaagcgc cgccgctgmt attaaaccta ccgtagcgct taacttgctt    18240
gtctgtgtgt gtatgtatta tgtcgccgcc gcygctgtcc accagaagga ggagtgaaga    18300
ggcgcgttgc cgagttgcra gatggccacc ccatcgatgc tgcccagtg ggcgtacatg     18360 cacatcgccg gacaggacgc ttcggagtac ctgagtccgg gtctggtgca gtttgcccgc    18420
gccacagaca cctacttcag tctggggaac aagtttagga accccacggt ggcgcccacg    18480
caygatgtga ccaccgaccg cagccagcgg ctgacgctgc gcttcgtgcc cgtggaccgc    18540
gaggacaaca cctactcgta caaagtgcgc tacacgctgg ccgtgggcga caaccgcgtg    18600
ctggacatgg ccagcaccta ctttgacatc cgcggcgtgc tggatcgggg ccctagcttc    18660
aaaccctact ccggcaccgc ctacaacagt ctggccccca agggagcacc caacacttgt    18720
cagtggacat ataaagccga tggtgaaact gccacagaaa aaacctatac atatggaaat    18780
gcacccgtgc agggcattaa catcacaaaa gatggtattc aacttggaac tgacaccgat    18840
gatcagccaa tctacgcaga taaaacctat cagcctgaac ctcaagtggg tgatgctgaa    18900
tggcatgaca tcactggtac tgatgaaaag tatggaggca gagctcttaa gcctgatacc    18960
aaaatgaagc cttgttatgg ttcttttgcc aagcctacta ataaagaagg aggtcaggca    19020
aatgtgaaaa caggaacagg cactactaaa gaatatgaca tagacatggc tttctttgac    19080
aacagaagtg cggctgctgc tggcctagct ccagaaattg ttttgtatac tgaaaatgtg    19140
gatttggaaa ctccagatac ccatattgta tacaaagcag gcacagatga cagcagctct    19200
tctattaatt tgggtcagca agccatgccc aacagaccta actacattgg tttcagagac    19260
aactttatcg ggctcatgta ctacaacagc actggcaata tggggtgct ggccggtcag     19320 gcttctcagc tgaatgctgt ggttgacttg caagacagaa acaccgagct gtcctaccag    19380
ctcttgcttg actctctggg tgacagaacc cggtatttca gtatgtggaa tcaggcggtg    19440
gacagctatg atcctgatgt gcgcattatt gaaaatcatg gtgtggagga tgaacttccc    19500
```

```
aactattgtt tccctctgga tgctgttggc agaacagata cttatcaggg aattaaggct   19560
aatgaactg  atcaaaccac atggaccaaa gatgacagtg tcaatgatgc taatgagata   19620
ggcaagggta atccattcgc catggaaatc aacatccaag ccaacctgtg gaggaacttc   19680
ctctacgcca acgtggccct gtacctgccc gactcttaca agtacacgcc ggccaatgtt   19740
accctgccca ccaacaccaa cacctacgat tacatgaacg gccgggtggt ggcgccctcg   19800
ctggtggact chtacatcaa catcggggcg cgctggtcgc tggatcccat ggacaacgtg   19860
aacccccttca accaccaccg caatgcgggg ctgcgctacc gctccatgct cctgggcaac   19920
gggcgctacg tgcccttcca catccaggtg ccccagaaat ttttcgccat caagagcctc   19980
ctgctcctgc ccgggtccta cacctacgag tggaacttcc gcaaggacgt caacatgatc   20040
ctgcagagct ccctcggcaa cgacctgcgc acggacgggg cctccatctc cttcaccagc   20100
atcaacctct acgccacctt cttccccatg gcgcacaaca cggcctccac gctcgaggcc   20160
atgctgcgca acgacaccaa cgaccagtcc ttcaacgact acctctcggc ggccaacatg   20220
ctctacccca tcccggccaa cgccaccaac gtgcccatct ccatcccctc gcgcaactgg   20280
gccgccttcc gcggctggtc cttcacgcgt ctcaagacca aggagacgcc ctcgctgggc   20340
tccgggttcg accctactt cgtctactcg ggctccatcc cctacctcga cggcaccttc   20400
tacctcaacc acaccttcaa gaaggtctcc atcaccttcg actcctccgt cagctggccc   20460
ggcaacgacc ggctcctgac gcccaacgag ttcgaaatca agcgcaccgt cgacggcgag   20520
ggctacaacg tggcccagtg caacatgacc aaggactggt tcctggtcca gatgctggcc   20580
cactacaaca tcggctacca gggcttctac gtgcccgagg gctacaagga ccgcatgtac   20640
tccttcttcc gcaacttcca gcccatgagc cgccaggtgg tggacgaggt caactacaag   20700
gactaccagg ccgtcaccct ggcctaccag cacaacaact cgggcttcgt cggctacctc   20760
gcgcccacca tgcgccaggg ccagccmtac cccgccaamt acccmtaccc gctcatcggc   20820
aagagcgccg tcaccagcgt cacccagaaa aagttcctct gcgacagggt catgtggcgc   20880
atccccttct ccagcaactt catgtccatg ggcgcgctca ccgacctcgg ccagaacatg   20940
ctctatgcca actccgccca cgcgctagac atgaatttcg aagtcgaccc catggatgag   21000
tccacccttc tctatgttgt cttcgaagtc ttcgacgtcg tccgagtgca ccagccccac   21060
cgcggcgtca tcgaggccgt ctacmtgcgc accccccttct cggccggtaa cgccaccacc   21120
taagctcttg cttcttgcaa gccatggccg cgggctccgg cgagcaggag ctcagggcca   21180
tcatccgcga cctgggctgc gggccmtact tcctgggcac sttcgataag cgcttcccgg   21240
gattcatggc cccgcacaag ctggcctgcg ccatcgtcaa cacggccggc cgcgagaccg   21300
ggggcgagca ctggctggcc ttcgcctgaa cccgcgctcg aacacctgct acctcttcga   21360
cccccttcggg ttctcggacg agcgcctcaa gcagatctac cagttcgagt acgagggcct   21420
gctgcgccgc agcgccctgg ccaccgagga ccgctgcgtc accctggaaa agtccaccca   21480
gaccgtgcag ggtccgcgct cggccgcctg cgggctcttc tgctgcatgt tcctgcacgc   21540
cttcgtgcac tggcccgacc gccccatgga caagaacccc accatgaact tgctgacggg   21600
ggtgcccaac ggcatgctcc agtcgcccca ggtggaaccc accctgcgcc gcaaccagga   21660
ggcgctytac cgcttcctca actcccactc cgcmtacttt cgctcccacc gcgcgcgcat   21720
cgagaaggcc accgccttcg accgcatgaa tcaagacatg taaaccgtgt gtgtatgtta   21780
aatgtctttta ataaacagca ctttcatgtt acacatgcat ctgagatgat ttatttagaa   21840
atcsaaaggg ttcttccggg tctcggcatg gcccgcgggc agggacacgt tgcggaactg   21900
```

```
gtacttggcc agccacttga actcggggat cagcagtttg ggcagcgggg tgtcgggaa    21960
ggagtcggtc cacagcttcc gcgtcagttg cagggcgccc agcaggtcgg gcgcggagat   22020
cttgaaatcg cagttgggac ccgcgttctg cgcgcgggag ttgcggtaca cggggttgca   22080
gcactggaac accatcaggg ccgggtgctt cacgctcgcc agcaccgtcg cgtcggtgat   22140
gctctccacg tcgaggtcct cggcgttggc catcccgaag gggtcatctc tgcaggtctg   22200
ccttcccatg gtgggcacgc acccgggctt gtggttgcaa tcgcagtgca ggggatcag    22260
catcatctgg gcctggtcgg cgttcatccc cgggtacatg gccttcatga aagcctccaa   22320
ttgcctgaac gcctgctggg ccttggctcc ctcggtgaag aagacccgc aggacttgct    22380
agagaactgg ttggtggcgc accggcgtc gtgcacgcag cagcgcgcgt cgttgttggc    22440
cagctgcacc acgctgcgcc cccagcggtt ctgggtgatc ttggcccggt cggggttctc   22500
cttcagcgcg cgctgccgt tctcgctcgc cacatccatc tcgatcatgt gctccttctg    22560
gatcatggtg gtcccgtgca ggcaccgcag cttgccctcg gcctcggtgc acccgtgcag   22620
ccacagcgcg cacccggtgc actcccagtt cttgtgggcg atctgggaat gcgcgtgcac   22680
gaagccctgc aggaagcggc ccatcatggt ggtcagggtc ttgttgctag tgaaggtcag   22740
cggaatgccg cggtgctcct cgttgatgta caggtggcag atgcggcggt acacctcgcc   22800
ctgctcgggc atcagctgga agttggcttt caggtcggtc tccacgcggt agcggtccat   22860
cagcatagtc atgatttcca taccttctc ccaggccgag acgatgggca ggctcatagg    22920
gttcttcacc atcatcttag cgctagcagc gcgggccagg gggtcgctct cgtccagggt   22980
ctcaaagctc cgcttgccgt ccttctcggt gatccgcacc gggggtagc tgaagcccac    23040
ggccgccagc tcctcctcgg cctgtctttc gtcctcgctg tcctggctga cgtcctgcag   23100
gaccacatgc ttggtcttgc ggggtttctt cttgggcggc agcggcggcg gagatgttgg   23160
agatggcgag ggggagcgcg agttctcgct caccactact atctcttcct cttcttggtc   23220
cgaggccacg cggcggtagg tatgtctctt cgggggcaga ggcggaggcg acgggctctc   23280
gccgccgcga cttggcggat ggctggcaga gccccttccg cgttcggggg tgcgctcccg   23340
gcggcgctct gactgacttc ctccgcggcc ggccattgtg ttctcctagg gaggaacaac   23400
aagcatggag actcagccat cgccaacctc gccatctgcc ccaccgccg acgagaagca    23460
gcagcagcag aatgaaagct taaccgcccc gccgcccagc ccgccacct ccgacgcggc    23520
cgtcccagac atgcaagaga tggaggaatc catcgagatt gacctgggct atgtgacgcc   23580
cgcggagcac gaggaggagc tgcagtgcg ctttttcacaa gaagagatac accaagaaca    23640
gccagagcag gaagcagaga atgagcagag tcaggctggg ctcgagcatg acggcgacta   23700
cctccacctg agcggggggg aggacgcgct catcaagcat ctggcccggc aggccaccat   23760
cgtcaaggat gcgctgctcg accgcaccga ggtgccctc agcgtggagg agctcagccg    23820
cgcctacgag ttgaacctct tctcgccgcg cgtgcccccc aagcgccagc ccaatggcac   23880
ctgcgagccc aacccgcgcc tcaacttcta cccggtcttc gcggtgcccg aggcctggc    23940
cacctaccac atctttttca agaaccaaaa gatccccgtc tcctgccgcg ccaaccgcac   24000
ccgcgccgac gcccttttca acctgggtcc cggcgcccgc ctacctgata tcgcctcctt   24060
ggaagaggtt cccaagatct tcgagggtct gggcagcgac gagactcggg ccgcgaacgc   24120
tctgcaagga gaaggaggag agcatgagca ccacagcgcc ctggtcgagt tggaaggcga   24180
caacgcgcgg ctggcggtgc tcaaacgcac ggtcgagctg acccatttcg cgtacccggc   24240
```

```
tctgaacctg ccccccaaag tcatgagcgc ggtcatggac caggtgctca tcaagcgcgc   24300
gtcgcccatc tccgaggacg agggcatgca agactccgag gagggcaagc ccgtggtcag   24360
cgacgagcag ctggcccggt ggctgggtcc taatgctagt ccccagagtt tggaagagcg   24420
gcgcaaactc atgatggccg tggtcctggt gaccgtggag ctggagtgcc tgcgccgctt   24480
cttcgccgac gcggagaccc tgcgcaaggt cgaggagaac ctgcactacc tcttcaggca   24540
cgggttcgtg cgccaggcct gcaagatctc caacgtggag ctgaccaacc tggtctcgta   24600
catgggcatc ttgcacgaga accgcctggg gcagaacgtg ctgcacacca ccctgcgcgg   24660
ggaggcccgg cgcgactaca tccgcgactg cgtctacctc tacctctgcc acacctggca   24720
gacgggcatg ggcgtgtggc agcagtgtct ggaggagcag aacctgaaag agctctgcaa   24780
gctcctgcag aagaactcaa gggtctgtgg accgggttcg acgagcgcac caccgcctcg   24840
gacctggccg acctcatttt ccccgagcgc ctcaggctga cgctgcgcaa cggcctgccc   24900
gactttatga gccaaagcat gttgcaaaac tttcgctctt tcatcctcga acgctccgga   24960
atcctgcccg ccacctgctc cgcgctgccc tcggacttcg tgccgctgac cttccgcgag   25020 tgcccccgc cgctgtggag ccactgctac ctgctgcgcc tggccaacta cctggcctac   25080
cactcggacg tgatcgagga cgtcagcggc gagggcctgc tcgagtgcca ctgccgctgc   25140
aacctctgca cgccgcaccg ctccctggcc tgcaaccccc agctgytgag cgagacccag   25200
atcatcggca ccttcgagtt gcaagggccc agcgaaggcg agggttcagc cgccaagggg   25260
ggtctgaaac tcaccccggg gctgtggacc tcggcctact tgcgcaagtt cgtgcccgag   25320
gactaccatc ccttcgagat caggttctac gaggaccaat cccatccgcc caaggccgag   25380
ctgtcggcct gcgtcatcac ccagggggcg atcctggccc aattgcaagc catccagaaa   25440
tcccgccaag aattcttgct gaaaaagggc gcgggggtct acctcgaccc ccagaccggt   25500
gaggagctca ccccccggctt ccccccaggat gcccccgagga aacaagaagc tgaaagtgga   25560
gctgccgccc gtggaggatt tggaggaaga ctgggagaac agcagtcagg cagaggagga   25620
ggagatggag gaagactggg acagcactca ggcagaggag gacagcctgc aagacagtct   25680
ggaggaagac gaggaggagg cagaggagga ggtggaagaa gcagccgccg ccagaccgtc   25740
gtcctcggcg ggggagaaag caagcagcac ggataccatc tccgctccgg gtcgggggtcc   25800 cgctcgacca cacagtagat gggacgagac cggacgattc ccgaacccca ccacccagac   25860
cggtaagaag gagcggcagg gatacaagtc ctggcggggg cacaaaaacg ccatcgtctc   25920
ctgcttgcag gcctgcgggg gcaacatctc cttcacccgg cgctacctgc tcttccaccg   25980
cggggtgaac tttccccgca acatcttgca ttactaccgt cacctccaca gcccctacta   26040
cttccaagaa gaggcagcag cagcagaaaa agaccagcag aaaaccagca gctagaaaat   26100
ccacagcggc ggcagcaggt ggactgagga tcgcggcgaa cgagccggcg caaacccggg   26160
agctgaggaa ccggatcttt cccaccctct atgccatctt ccagcagagt cggggggcagg   26220 agcaggaact gaaagtcaag aaccgttctc tgcgctcgct caccccgcagt tgtctgtatc   26280 acaagagcga agaccaactt cagcgcactc tcgaggacgc cgaggctctc ttcaacaagt   26340
actgcgcgct cactcttaaa gagtagcccg cgcccgccca gtcgcagaaa aaggcgggaa   26400
ttacgtcacc tgtgcccttc gccctagccg cctccaccca tcatcatgag caaagagatt   26460
cccacgccct tacatgtggag ctaccagccc cagatgggcc tggccgccgg tgccgcccag   26520
gactactcca cccgcatgaa ttggctcagc gccgggcccg cgatgatctc acgggtgaat   26580
gacatccgcg cccaccgaaa ccagatactc ctagaacagt cagcgctcac cgccacgccc   26640
```

```
cgcaatcacc tcaatccgcg taattggccc gccgccctgg tgtaccagga aattccccag    26700
cccacgaccg tactacttcc gcgagacgcc caggccgaag tccagctgac taactcaggt    26760
gtccagctgg cgggcggcgc caccctgtgt cgtcaccgcc ccgctcaggg tataaagcgg    26820
ctggtgatcc ggggcagaag cacacagctc aacgacgaag tggtgagctc ttcgctgggt    26880
ctgcgacctg acgagtctt ccaactcgcc ggatcgggga gatcttcctt cacgcctcgt     26940
caggccgtcc tgactttgga gagttcgtcc tcgcagcccc gctcgggtgg catcggcact    27000
ctccagttcg tggaggagtt cactccctcg gtctacttca acccttctc cggctccccc     27060 ggccactacc cggacgagtt catcccgaac ttcgacgcca tcagcgagtc ggtggacggc    27120
tacgattgaa tgtcccatgg tggcgcagct gacctagctc ggcttcgaca cctggaccac    27180
tgccgccgct tccgctgctt cgctcgggat ctcgccgagt ttgcctactt tgagctgccc    27240
gaggagcacc ctcagggccc ggcccacgga gtgcggatcg tcgtcgaagg gggcctcgac    27300
tcccacctgc ttcggatctt cagccagcgt ccgatcctgg tcgagcgcga gcaaggacag    27360
acccttctga ctctgtactg catctgcaac caccccggcc tgcatgaaag tctttgttgt    27420
ctgctgtgta ctgagtataa taaaagctga gacagcgact actccggact tccgtgtgtt    27480
cctgaatcca tcaaccagtc tttgttcttc accgggaacg agaccgagct ccagctccag    27540
tgtaagcccc acaagaagta cctcacctgg ctgttccagg gctccccgat cgccgttgtc    27600
aaccactgcg acaacgacgg agtcctgstg agcggccctg ccaaccwtac tttttccacc    27660
cgcagaagca agctccagct sttccaaccc ttcctcccccg ggacctatca gtgcgtctcg   27720
ggaccctgcc atcacacctt ccacctgatc ccgaatacca cagcgtcgct ccccgmtact    27780
aacaaccaaa ctaacctcca ccaacgccac cgtcgcgacc tttctgaatc taatactacc    27840
acccacaccg gaggtgagct ccgaggtcaa ccaacctctg ggatttacta cggcccctgg    27900
gaggtggttg ggttaataac gctaggccta gttgcgggtg ggcttttggt tctctgctac    27960
ctatacctcc cttgctgttc gtacttagtg gtgctgtgtt gctggtttaa gaaatgggga    28020
agatcaccct agtgagctgc ggtgcgctgg tggcggtgtt gctttcgatt gtgggactgg    28080
gcggtgcggc tgtantgaaa gagaaggccg atccctgctt gcatttcaat cccaacaaat    28140
gccagctgag ttttcagccc gatggcaatc ggtgcgcggt actgatcaag tgcggatggg    28200
aatgcgagaa cgtgagaatc gagtacaata acaagactcg gaacaatact ctcgcgtccg    28260
tgtggcagcc cggggacccc gagtggtaca ccgtctctgt ccccggtgct gacggctccc    28320
cgcgcaccgt gaataatact ttcattttg cgcacatgtg cgacacggtc atgtggatga    28380
gcaagcagta cgtatgtgg ccccccacga aggagaacat cgtggtcttc tccatcgctt     28440
acagcctgtg cacggcgcta atcaccgcta tcgtgtgcct gagcattcac atgctcatcg    28500
ctattcgccc cagaaataat gccgaaaaag aaaacagcc ataacgtttt ttttcacacc     28560
tttttcagac catggcctct gttaaattt tgctttatt tgccagtctc attgccgtca     28620
ttcatggaat gagtaatgag aaaattacta tttacactgg cactaatcac acattgaaag    28680
gtccagaaaa agccacagaa gtttcatggt attgttattt taatgaatca gatgtatcta    28740
ctgaactctg tggaaacaat aacaaaaaaa atgagagcat tactctcatc aagtttcaat    28800
gtggatctga cttaacccta attaacatca ctagagacta tgtaggtatg tattatgaa     28860 ctacagcagg catttcggac atggaatttt atcaagtttc tgtgtctgaa cccaccacgc    28920
ctagaatgac cacaaccaca aaaactacac ctgttaccac tatgcagctc actaccaata    28980
```

```
acatttttgc catgcgtcaa atggtcaaca atagcactca acccaccca cccagtgagg    29040
aaattcccaa atccatgatt ggcattattg ttgctgtagt ggtgtgcatg ttgatcatcg   29100
ccttgtgcat ggtgtactat gccttctgct acagaaagca cagactgaac gacaagctgg  29160
aacacttact aagtgttgaa ttttaatttt ttagaaccat gaagatccta ggccttttaa  29220
tttttctat cattacctct gctctatgca attctgacaa tgaggacgtt actgtcgttg   29280
tcggatcaaa ttatacactg aaaggtccag cgaagggtat gctttcgtgg tattgctatt  29340
ttggatctga cactacagaa actgaattat gcnatcttaa gaatggcaaa attcaaaatt  29400
cttaaaatta acaattatat atgcaatggt actgatctga tactcctcaa tatcacgaaa  29460
tcatatgstg gcagttacac ctgccctgga gatgatgctg acagtatgat tttttacaaa  29520
gtaactgttg ttgatcccat actccacctc cacccaccac aattactcac accacacaca  29580
cagatcaaac cgcagcagag gaggcagcaa agttagcctt gcaggtccaa gacagttcat  29640
ttgttggcat taccccctaca catgatcagc ggtgtccggg gctgctagtc agcggcattg  29700
tcggtgtgct ttcgggatta gcagtcataa tcatctgcat gttcattttt gcttgctgct  29760
atagaaggct ttaccgacaa aaatcagacc cactgctgaa cctctatgtt taatttttc  29820
cagagtcatg aaggcagtta gcgctctagt tttttgttct wtgattggca ttgtttttg    29880
caatcctatt cctaaagtta gctttattaa agatgtgaat gttactgagg ggcaatgt    29940
gacactggta ggtgtagagg gtgctgaaaa caccacctgg acaaaatacc acctcaatgg  30000
gtggaaagat atttgcaatt ggagtgtatt agtttataca tgtgagggag ttaatcttac  30060
cattgtcaat gccacctcag ctcaaaatgg tagaattcaa ggacaaagtg tcagtgtatc  30120
taatgggtat tttacccaac atacttttat ctatgacgtt aaagtcatac cactgcwtac  30180
gcttagccca cttagcatta ccacacagac aacccacatt acacagacaa ccacatacag  30240
tacattaaat cagcbtacca ccactacagc agcagaggtt gccagctcgt ctggggtccg  30300
agtggcattt ttgatgtggg ccccatmtag cagtcccact gctagtacca atgagcagac  30360
tactgaattt ttgtccactg tcgagagcca caccacagct acctccagtg ccttctctag  30420
caccgccaat ctctcctcgc tttcctntac accaatcagt cccgytaata ctcctagccc  30480
cgtcctcttc ccactcccct gaagcaaaca gacggcggca tgcaatggca gatcaccctg  30540
ctcattgtga tcgggttggt catcctggcc gtgttgctct actacatctt ctgccgccgc  30600
attcccaacg cgcaccgcaa gccggtatac aagcccatca ttgtcgggca gccggagccg  30660
cttcaggtgg aaggggtct aaggaatctt ctcttctctt ttacagtatg gtgattgaac   30720
tatgattcct agacaattct tgatcactat tcttatctgc ctcctccaag tctgtgccac   30780
cctcgctctg gtgccaacg ccagtccaga ctgtattggg cccttcgcct cctacgtgct   30840
cctttgccttc accacctgca tctgctgctg tagcatagtc tgcctgctta tcaccttctt  30900
ccagttcatt gactggatct ttgtgcgcat cgcmtacctg cgccaccacc cccagtaccg  30960
cgaccagcga gtggcgcggc tgctcaggct cctctgataa gcatgcgggc tgtgntactt  31020
ctcgcgcttc tgctgttagt gctcccccgt cccgtcgacc cccggtcccc cacccagtcc  31080
cccgaggagg tccgcaaatg caaattccaa gaaccctgga aattcctcaa atgctaccgc  31140
caaaaatcag acatgcatcc cagctggatc atgatcattg ggatcgtgaa cattctggcc  31200
tgcaccctca tctcctttgt gatttacccc tgctttgact ttggttggaa ctcgccagag  31260
gcgctctatc tcccgcctga acctgacaca ccaccacagc aacctcaggc acacgcacta  31320
ccaccactac agcctaggcc acaatacatg cccatattag actatgaggc cgagccacag  31380
```

```
cgacccatgc tccccgctat tagttacttc aatctaaccg gcggagatga ctgacccact   31440
ggccaacaac aacgtcaacg accttctcct ggacatggac ggccgcgcct cggagcagcg   31500
actcgcccaa cttcgcattc gccagcagca ggagagagcc gtcaaggagc tgcaggatgc   31560
ggtggccatc caccagtgca agagaggcat cttctgcctg gtgaaacagg ccaagatctc   31620
ctacgaggtc actccaaacg accatcgcct ctcctacgag ctcctgcagc agcgccagaa   31680
gttcacctgc ctggtcggag tcaaccccat cgtcatcacc cagcagtctg gcgataccaa   31740
ggggtgcatc cactgctcct gcgactcccc cgactgcgtc cacactctga tcaagaccct   31800
stgcggcctc cgcgacctcc tccccatgaa ctaatcaccc ccttatccag tgaaataaag   31860
atcatattga tgatgatttt acagaaataa aaaataatca tttgatttga aataaagata   31920
caatcatatt gatgatttga gtttaacaaa aaaataaaga atcacttact tgaaatctga   31980
taccaggtct ctgtccatgt tttctgccaa caccacttca ctcccctctt cccagctctg   32040
gtactgcagg ccccggcggg ctgcaaactt cctccacacg ctgaagggga tgtcaaattc   32100
ctcctgtccc tcaatcttca ttttatcttc tatcagatgt ccaaaaagcg cgtccgggtg   32160
gatgatgact tcgaccccgt ctaccctac gatgcagaca acgcaccgac cgtgcccttc   32220
atcaaccccc ccttcgtctc ttcagatgga ttccaagaga agccctggg ggtgttgtcc   32280
ctgcgactgg ccgaccccgt caccaccaag aacggggaaa tcaccctcaa gctgggagag   32340
ggggtggacc tcgattcctc gggaaaactc atctccaaca cggccaccaa ggccgccgcc   32400
cctctcagtt tttccaacaa caccatttcc cttaacatgg atcacccctt ttacactaaa   32460
gatggaaaat tatccttaca agtttctcca ccattaaata tactgagaac aagcattcta   32520
aacacactag ctttaggttt tggatcaggt ttaggactcc gtggctctgc cttggcagta   32580
cagttagtct ctccacttac atttgatact gatggaaaca taaagcttac cttagacaga   32640
ggtttgcatg ttacaacagg agatgcaatt gaaagcaaca taagctgggc taaaggttta   32700
aaatttgaag atggagccat agcaaccaac attggaaatg ggttagagtt tggaagcagt   32760
agtacagaaa caggtgttga tgatgcttac ccaatccaag ttaaacttgg atctggcctt   32820
agctttgaca gtacaggagc cataatggct ggtaacaaag aagacgataa actcactttg   32880
tggacaacac ctgatccatc accaaactgt caaatactcg cagaaaatga tgcaaaacta   32940
acactttgct tgactaaatg tggtagtcaa atactggcca ctgtgtcagt cttagttgta   33000
ggaagtggaa acctaaaccc cattactggc accgtaagca gtgctcaggt gtttctacgt   33060
tttgatgcaa acggtgttct tttaacagaa cattctacac taaaaaaata ctgggggtat   33120
aggcagggag atagcataga tggcactcca tataccaatg ctgtaggatt catgcccaat   33180
ttaaaagctt atccaaagtc acaaagttct actactaaaa ataatatagt agggcaagta   33240
tacatgaatg gagatgtttc aaaacctatg cttctcacta taaccctcaa tggtactgat   33300
gacagcaaca gtacatattc aatgtcattt tcatacacct ggactaatgg aagctatgtt   33360
ggagcaacat ttggggctaa ctcttatacc ttctcataca tcgcccaaga tgaacactg   33420
tatcccaccc tgcatgccaa cccttcccac cccactctgt ggaacaaact ctgaaacaca   33480
aaataaaata aagttcaagt gttttattga ttcaacagtt ttacaggatt cgagcagtta   33540
tttttcctcc accctcccag gacatggaat acaccaccct ctcccccgc acagccttga   33600
acatctgaat gccattggtg atggacatgc ttttggtctc cacgttccac acagtttcag   33660
agcgagccag tctcgggtcg gtcagggaga tgaaaccctc cgggcactcc cgcatctgca   33720
```

```
cctcacagct caacagctga ggattgtcct cggtggtcgg gatcacggtt atctggaaga    33780
agcagaagag cggcggtggg aatcatagtc cgcgaacggg atcggccggt ggtgtcgcat    33840
caggccccgc agcagtcgct gccgccgccg ctccgtcaag ctgctgctca gggggtccgg    33900
gtccagggac tccctcagca tgatgcccac ggccctcagc atcagtcgtc tggtgcggcg    33960
ggcgcagcag cgcatgcgga tctcgctcag gtcgctgcag tacgtgcaac acagaaccac    34020
caggttgttc aacagtccat agttcaacac gctccagccg aaactcatcg cgggaaggat    34080
gctacccacg tggccgtcgt accagatcct caggtaaatc aagtggtgcc ccctccagaa    34140
cacgctgccc acgtacatga tctccttggg catgtggcgg ttcaccacct cccggtacca    34200
catcaccctc tggttgaaca tgcagccccg gatgatcctg cggaaccaca gggccagcac    34260
cgccccgccc gccatgcagc gaagagaccc cgggtcccgg caatggcaat ggaggaccca    34320
ccgctcgtac ccgtggatca tctgggagct gaacaagtct atgttggcac agcacaggca    34380
tatgctcatg catctcttca gcactctcaa ctcctcgggg gtcaaaacca tatcccaggg    34440
cacggggaac tcttgcagga cagcgaaccc cgcagaacag ggcaatcctc gcacagaact    34500
tacattgtgc atggacaggg tatcgcaatc aggcagcacc gggtgatcct ccaccagaga    34560
agcgcgggtc tcggtctcct cacagcgtgg taagggggcc ggccgatacg ggtgatggcg    34620
ggacgcggct gatcgtgttc gcgaccgtgt catgatgcag ttgctttcgg acattttcgt    34680
acttgctgta gcagaacctg gtccgggcgc tgcacaccga tcgccggcgg cggtctcggc    34740
gcttggaacg ctcggtgttg aaattgtaaa acagccactc tctcagaccg tgcagcagat    34800
ctagggcctc aggagtgatg aagatcccat catgcctgat ggctctgatc acatcgacca    34860
ccgtggaatg ggccagaccc agccagatga tgcaattttg ttgggtttcg gtgacggcgg    34920
gggagggaag aacaggaaga accatgatta acttttaatc caaacggtct cggagtactt    34980
caaaatgaag atcgcggaga tggcacctct cgccccgct gtgttggtgg aaaataacag    35040
ccaggtcaaa ggtgatacgg ttctcgagat gttccacggt ggcttccagc aaagcctcca    35100
cgcgcacatc cagaaacaag acaatagcga aagcgggagg gttctctaat tcctcaatca    35160
tcatgttaca ctcstgcacc atccccagat aattttcatt tttccagcct tgaatgattc    35220
gaactagttc gtgaggtaaa tccaagccag ccatgataaa gagctcgcgc agagcgccct    35280
ccaccggcat tcttaagcac accctcataa ttccaagata ttctgctcct ggttcacctg    35340
cagcagattg acaagcggaa tatcaaaatc tctgccgcga tccctgagct cctccctcag    35400
caataactgt aagtactctt tcatatcctc tccgaaattt ttagccatag gaccaccagg    35460
aataagatta gggcaagcca cagtacagat aaaccgaagt cctccccagt gagcattgcc    35520
aaatgcaaga ctgctataag catgctggct agacccggtg atatcttcca gataactgga    35580
cagaaaatcg cccaggcaat ttttaagaaa atcaacaaaa gaaaaatcct ccaggtggac    35640
gtttagagcc tcgggaacaa cgatgaagta atgcaagcg gtgcgttcca gcatggttag    35700
ttagctgatc tgtagaaaaa acaaaaatga acattaaacc atgctagcct ggcgaacagg    35760
tgggtaaatc gttctctcca gcaccaggca ggccacgggg tctccggcgc gaccctcgta    35820
aaaattgtcg ctatgattga aaaccatcac agagagacgt tcccggtggc cggcgtgaat    35880
gattcgacaa gatgaataca cccccggaac attggcgtcc gcgagtgaaa aaaagcgccc    35940
gaggaagcaa taaggcacta caatgctcag tctcaagtcc agcaaagcga tgccatgcgg    36000
atgaagcaca aaattctcag gtgcgtacaa aatgtaatta ctcccctcct gcacaggcag    36060
caaagccccc gatccctcca ggtacacata caaagcctca gcgtccatag cttaccgagc    36120
```

-continued

```
agcagcacac aacaggcgca agagtcagag aaaggctgag ctctaacctg tccacccgct    36180
ctctgctcaa tatatagccc agatctacac tgacgtaaag gccaaagtct aaaaatacccc   36240 gccaaataat cacacacgcc cagcacacgc ccagaaaccg gtgacacact caaaaaaata   36300
cgcgcacttc ctcaaacgcc caaaactgcc gtcatttccg ggttcccacg ctacgtcatc   36360
aaaacacgac tttcaaattc cgtcgaccgt taaaaacgtc acccgccccg ccctaacgg    36420 tcgcccgtct ctcagccaat cagcgccccg catccccaaa ttcaaacacc tcatttgcat   36480
attaacgcgc acaaaaagtt tgaggtatat tattgatgat g                         36521
```

<210> SEQ ID NO 34
<211> LENGTH: 314
<212> TYPE: PRT
<213> ORGANISM: Human adenovirus type 4

<400> SEQUENCE: 34

```
Asn Thr Cys Gln Trp Lys Asp Ser Asp Ser Lys Met His Thr Phe Gly
 1               5                  10                  15

Ala Ala Ala Met Pro Gly Val Thr Gly Lys Lys Ile Glu Ala Asp Gly
            20                  25                  30

Leu Pro Ile Arg Ile Asp Ser Thr Ser Gly Thr Asp Thr Val Ile Tyr
        35                  40                  45

Ala Asp Lys Thr Phe Gln Pro Glu Pro Gln Val Gly Asn Asp Ser Trp
    50                  55                  60

Val Asp Thr Asn Gly Ala Glu Glu Lys Tyr Gly Gly Arg Ala Leu Lys
65                  70                  75                  80

Asp Thr Thr Lys Met Asn Pro Cys Tyr Gly Ser Phe Ala Lys Pro Thr
                85                  90                  95

Asn Lys Glu Gly Gly Gln Ala Asn Leu Lys Asp Ser Glu Pro Ala Ala
           100                 105                 110

Thr Thr Pro Asn Tyr Asp Ile Asp Leu Ala Phe Phe Asp Ser Lys Thr
       115                 120                 125

Ile Val Ala Asn Tyr Asp Pro Asp Ile Val Met Tyr Thr Glu Asn Val
   130                 135                 140

Asp Leu Gln Thr Pro Asp Thr His Ile Val Tyr Lys Pro Gly Thr Glu
145                 150                 155                 160

Asp Thr Ser Ser Glu Ser Asn Leu Gly Gln Gln Ala Met Pro Asn Arg
                165                 170                 175

Pro Asn Tyr Ile Gly Phe Arg Asp Asn Phe Ile Gly Leu Met Tyr Tyr
           180                 185                 190

Asn Ser Thr Gly Asn Met Gly Val Leu Ala Gly Gln Ala Ser Gln Leu
       195                 200                 205

Asn Ala Val Val Asp Leu Gln Asp Arg Asn Thr Glu Leu Ser Tyr Gln
   210                 215                 220

Leu Leu Leu Asp Ser Leu Gly Asp Arg Thr Arg Tyr Phe Ser Met Trp
225                 230                 235                 240

Asn Gln Ala Val Asp Ser Tyr Asp Pro Asp Val Arg Ile Ile Glu Asn
                245                 250                 255

His Gly Val Glu Asp Glu Leu Pro Asn Tyr Cys Phe Pro Leu Asn Gly
           260                 265                 270

Val Gly Leu Thr Asp Thr Tyr Gln Gly Val Lys Val Lys Thr Asp Ala
       275                 280                 285

Gly Ser Glu Lys Trp Asp Lys Asp Thr Thr Val Ser Asn Ala Asn
   290                 295                 300
```

```
Glu Ile His Val Gly Asn Pro Phe Ala Met
305                 310
```

<210> SEQ ID NO 35
<211> LENGTH: 318
<212> TYPE: PRT
<213> ORGANISM: Human adenovirus type 16

<400> SEQUENCE: 35

```
Asn Thr Cys Gln Trp Lys Asp Ser Asp Ser Lys Met His Thr Phe Gly
1               5                   10                  15

Val Ala Ala Met Pro Gly Val Thr Gly Lys Lys Ile Glu Ala Asp Gly
            20                  25                  30

Leu Pro Ile Gly Ile Asp Ser Thr Ser Gly Thr Asp Thr Val Ile Tyr
        35                  40                  45

Ala Asp Lys Thr Phe Gln Pro Glu Pro Gln Val Gly Asn Ala Ser Trp
    50                  55                  60

Val Asp Ala Asn Gly Thr Glu Glu Lys Tyr Gly Gly Arg Ala Leu Lys
65                  70                  75                  80

Asp Thr Thr Lys Met Lys Pro Cys Tyr Gly Ser Phe Ala Lys Pro Thr
                85                  90                  95

Asn Lys Glu Gly Gly Gln Ala Asn Leu Lys Asp Ser Glu Thr Ala Ala
            100                 105                 110

Thr Thr Pro Asn Tyr Asp Ile Asp Leu Ala Phe Phe Asp Asn Lys Asn
        115                 120                 125

Ile Ala Ala Asn Tyr Asp Pro Asp Ile Val Met Tyr Thr Glu Asn Val
    130                 135                 140

Asp Leu Gln Thr Pro Asp Thr His Ile Val Tyr Lys Pro Gly Thr Glu
145                 150                 155                 160

Asp Thr Ser Ser Glu Ser Asn Leu Gly Gln Gln Ala Met Pro Asn Arg
                165                 170                 175

Pro Asn Tyr Ile Gly Phe Arg Asp Asn Phe Ile Gly Leu Met Tyr Tyr
            180                 185                 190

Asn Ser Thr Gly Asn Met Gly Val Leu Ala Gly Gln Ala Ser Gln Leu
        195                 200                 205

Asn Ala Val Val Asp Leu Gln Asp Arg Asn Thr Glu Leu Ser Tyr Gln
    210                 215                 220

Leu Leu Leu Asp Ser Leu Gly Asp Arg Thr Arg Tyr Phe Ser Met Trp
225                 230                 235                 240

Asn Gln Ala Val Asp Ser Tyr Asp Pro Asp Val Arg Ile Ile Glu Asn
                245                 250                 255

His Gly Val Glu Asp Glu Leu Pro Asn Tyr Cys Phe Pro Leu Asn Gly
            260                 265                 270

Val Gly Phe Thr Asp Thr Tyr Gln Gly Val Lys Val Lys Thr Asp Ala
        275                 280                 285

Val Ala Gly Thr Ser Gly Thr Gln Trp Asp Lys Asp Asp Thr Thr Val
    290                 295                 300

Ser Thr Ala Asn Glu Ile His Gly Gly Asn Pro Phe Ala Met
305                 310                 315
```

<210> SEQ ID NO 36
<211> LENGTH: 323
<212> TYPE: PRT
<213> ORGANISM: Human adenovirus type 3

<400> SEQUENCE: 36

```
Asn Thr Ser Gln Trp Ile Val Thr Thr Asn Gly Asp Asn Ala Val Thr
1               5                   10                  15

Thr Thr Thr Asn Thr Phe Gly Ile Ala Ser Met Lys Gly Gly Asn Ile
            20                  25                  30

Thr Lys Glu Gly Leu Gln Ile Gly Lys Asp Ile Thr Thr Thr Glu Gly
        35                  40                  45

Glu Glu Lys Pro Ile Tyr Ala Asp Lys Thr Tyr Gln Pro Glu Pro Gln
    50                  55                  60

Val Gly Glu Glu Ser Trp Thr Asp Thr Asp Gly Thr Asn Glu Lys Phe
65                  70                  75                  80

Gly Gly Arg Ala Leu Lys Pro Ala Thr Asn Met Lys Pro Cys Tyr Gly
                85                  90                  95

Ser Phe Ala Arg Pro Thr Asn Ile Lys Gly Gly Gln Ala Lys Asn Arg
                100                 105                 110

Lys Val Lys Pro Thr Thr Glu Gly Gly Val Glu Thr Glu Pro Asp
                115                 120                 125

Ile Asp Met Glu Phe Phe Asp Gly Arg Asp Ala Val Ala Gly Ala Leu
130                 135                 140

Ala Pro Glu Ile Val Leu Tyr Thr Glu Asn Val Asn Leu Glu Thr Pro
145                 150                 155                 160

Asp Ser His Val Val Tyr Lys Pro Glu Thr Ser Asn Asn Ser His Ala
                165                 170                 175

Asn Leu Gly Gln Gln Ala Met Pro Asn Arg Pro Asn Tyr Ile Gly Phe
                180                 185                 190

Arg Asp Asn Phe Val Gly Leu Met Tyr Tyr Asn Ser Thr Gly Asn Met
                195                 200                 205

Gly Val Leu Ala Gly Gln Ala Ser Gln Leu Asn Ala Val Val Asp Leu
                210                 215                 220

Gln Asp Arg Asn Thr Glu Leu Ser Tyr Gln Leu Leu Leu Asp Ser Leu
225                 230                 235                 240

Gly Asp Arg Thr Arg Tyr Phe Ser Met Trp Asn Gln Ala Val Asp Ser
                245                 250                 255

Tyr Asp Pro Asp Val Arg Ile Ile Glu Asn His Gly Ile Glu Asp Glu
                260                 265                 270

Leu Pro Asn Tyr Cys Phe Pro Leu Asn Gly Ile Gly Pro Gly His Thr
                275                 280                 285

Tyr Gln Gly Ile Lys Lys Val Lys Thr Asp Asp Thr Asn Gly Trp Glu
                290                 295                 300

Lys Asp Ala Asn Val Ala Pro Ala Asn Glu Ile Thr Ile Gly Asn Asn
305                 310                 315                 320

Leu Ala Met

<210> SEQ ID NO 37
<211> LENGTH: 315
<212> TYPE: PRT
<213> ORGANISM: Human adenovirus type 7

<400> SEQUENCE: 37

Asn Thr Ser Gln Trp Ile Val Thr Ala Gly Glu Glu Arg Ala Val Thr
1               5                   10                  15

Thr Thr Thr Asn Thr Phe Gly Ile Ala Ser Met Lys Gly Asp Asn Ile
            20                  25                  30

Thr Lys Glu Gly Leu Glu Ile Gly Lys Asp Ile Thr Ala Asp Asn Lys
        35                  40                  45
```

-continued

Pro Ile Tyr Ala Asp Lys Thr Tyr Gln Pro Glu Pro Gln Val Gly Glu
 50                  55                  60

Glu Ser Trp Thr Asp Thr Asp Gly Thr Asn Glu Lys Phe Gly Gly Arg
65                  70                  75                  80

Ala Leu Lys Pro Ala Thr Lys Met Lys Pro Cys Tyr Gly Ser Phe Ala
                 85                  90                  95

Arg Pro Thr Asn Ile Lys Gly Gly Gln Ala Lys Asn Arg Lys Val Lys
             100                 105                 110

Pro Thr Glu Gly Asp Val Glu Thr Glu Pro Asp Ile Asp Met Glu
         115                 120                 125

Phe Phe Asp Gly Arg Glu Ala Ala Asp Ala Phe Ser Pro Glu Ile Val
         130                 135                 140

Leu Tyr Thr Glu Asn Val Asn Leu Glu Thr Pro Asp Ser His Val Val
145                 150                 155                 160

Tyr Lys Pro Gly Thr Ser Asp Asp Asn Ser His Ala Asn Leu Gly Gln
                 165                 170                 175

Gln Ala Met Pro Asn Arg Pro Asn Tyr Ile Gly Phe Arg Asp Asn Phe
             180                 185                 190

Val Gly Leu Met Tyr Tyr Asn Ser Thr Gly Asn Met Gly Val Leu Ala
         195                 200                 205

Gly Gln Ala Ser Gln Leu Asn Ala Val Val Asp Leu Gln Asp Arg Asn
210                 215                 220

Thr Glu Leu Ser Tyr Gln Leu Leu Leu Asp Ser Leu Gly Asp Arg Thr
225                 230                 235                 240

Arg Tyr Phe Ser Met Trp Asn Gln Ala Val Asp Ser Tyr Asp Pro Asp
                 245                 250                 255

Val Arg Ile Ile Glu Asn His Gly Ile Glu Asp Glu Leu Pro Asn Tyr
             260                 265                 270

Cys Phe Pro Leu Asp Gly Ile Gly Pro Ala Lys Thr Tyr Gln Gly Ile
         275                 280                 285

Lys Ser Lys Asp Asn Gly Trp Glu Lys Asp Asp Asn Val Ser Lys Ser
         290                 295                 300

Asn Glu Ile Ala Ile Gly Asn Asn Gln Ala Met
305                 310                 315

<210> SEQ ID NO 38
<211> LENGTH: 345
<212> TYPE: PRT
<213> ORGANISM: Human adenovirus type 2

<400> SEQUENCE: 38

Asn Ser Cys Glu Trp Glu Gln Thr Glu Asp Ser Gly Arg Ala Val Ala
1               5                   10                  15

Glu Asp Glu Glu Glu Glu Asp Glu Asp Glu Glu Glu Glu Glu Glu Glu
                20                  25                  30

Gln Asn Ala Arg Asp Gln Ala Thr Lys Lys Thr His Val Tyr Ala Gln
             35                  40                  45

Ala Pro Leu Ser Gly Glu Thr Leu Thr Lys Ser Gly Leu Gln Ile Gly
 50                  55                  60

Ser Lys Asn Ala Glu Thr Gln Ala Lys Pro Val Tyr Ala Asp Pro Ser
65                  70                  75                  80

Tyr Gln Pro Glu Pro Gln Ile Gly Glu Ser Gln Trp Asn Glu Ala Asp
                 85                  90                  95

Ala Asn Ala Ala Gly Gly Arg Val Leu Lys Lys Thr Thr Pro Met Lys

```
                    100                 105                 110
Pro Tyr Gly Ser Tyr Ala Arg Pro Thr Asn Pro Phe Gly Gly Gln Ser
            115                 120                 125

Val Leu Val Pro Asp Glu Lys Gly Val Pro Leu Pro Lys Val Asp Leu
        130                 135                 140

Gln Phe Phe Ser Asn Thr Thr Ser Leu Asn Asp Arg Gln Gly Asn Ala
145                 150                 155                 160

Thr Lys Pro Lys Val Val Leu Tyr Ser Glu Asp Val Asn Met Glu Thr
                165                 170                 175

Pro Asp Thr His Leu Ser Tyr Lys Pro Gly Lys Gly Asp Glu Asn Ser
            180                 185                 190

Lys Ala Met Leu Gly Gln Gln Ser Met Pro Asn Arg Pro Asn Tyr Ile
        195                 200                 205

Ala Phe Arg Asp Asn Phe Ile Gly Leu Met Tyr Tyr Asn Ser Thr Gly
        210                 215                 220

Asn Met Gly Val Leu Ala Gly Gln Ala Ser Gln Leu Asn Ala Val Val
225                 230                 235                 240

Asp Leu Gln Asp Arg Asn Thr Glu Leu Ser Tyr Gln Leu Leu Leu Asp
                245                 250                 255

Ser Ile Gly Asp Arg Thr Arg Tyr Phe Ser Met Trp Asn Gln Ala Val
            260                 265                 270

Asp Ser Tyr Asp Pro Asp Val Arg Ile Ile Glu Asn His Gly Thr Glu
        275                 280                 285

Asp Glu Leu Pro Asn Tyr Cys Phe Pro Leu Gly Gly Ile Gly Val Thr
        290                 295                 300

Asp Thr Tyr Gln Ala Ile Lys Ala Asn Gly Asn Gly Ser Gly Asp Asn
305                 310                 315                 320

Gly Asp Thr Thr Trp Thr Lys Asp Glu Thr Phe Ala Thr Arg Asn Glu
                325                 330                 335

Ile Gly Val Gly Asn Asn Phe Ala Met
            340                 345

<210> SEQ ID NO 39
<211> LENGTH: 183
<212> TYPE: PRT
<213> ORGANISM: human adenovirus protein

<400> SEQUENCE: 39

Thr Leu Trp Thr Thr Pro Asp Pro Ser Pro Asn Cys Arg Ile His Ser
1               5                   10                  15

Asp Asn Asp Cys Lys Phe Thr Leu Val Leu Thr Lys Cys Gly Ser Gln
                20                  25                  30

Val Leu Ala Thr Val Ala Ala Leu Ala Val Ser Gly Asp Leu Ser Ser
            35                  40                  45

Met Thr Gly Thr Val Ala Ser Val Ser Ile Phe Leu Arg Phe Asp Gln
        50                  55                  60

Asn Gly Val Leu Met Glu Asn Ser Ser Leu Lys Lys His Tyr Trp Asn
65                  70                  75                  80

Phe Arg Asn Gly Asn Ser Thr Asn Ala Asn Pro Tyr Thr Asn Ala Val
                85                  90                  95

Gly Phe Met Pro Asn Leu Leu Ala Tyr Pro Lys Thr Gln Ser Gln Thr
            100                 105                 110

Ala Lys Asn Asn Ile Val Ser Gln Val Tyr Leu His Gly Asp Lys Thr
        115                 120                 125
```

```
Lys Pro Met Ile Leu Thr Ile Thr Leu Asn Gly Thr Ser Glu Ser Thr
    130                 135                 140
Glu Thr Ser Glu Val Ser Thr Tyr Ser Met Ser Phe Thr Trp Ser Trp
145                 150                 155                 160
Glu Ser Gly Lys Tyr Thr Thr Glu Thr Phe Ala Thr Asn Ser Tyr Thr
                165                 170                 175
Phe Ser Tyr Ile Ala Gln Glu
            180

<210> SEQ ID NO 40
<211> LENGTH: 182
<212> TYPE: PRT
<213> ORGANISM: human adenovirus protein

<400> SEQUENCE: 40

Thr Leu Trp Thr Thr Pro Ala Pro Ser Pro Asn Cys Arg Leu Asn Ala
1               5                   10                  15
Glu Lys Asp Ala Lys Leu Thr Leu Val Leu Thr Lys Cys Gly Ser Gln
                20                  25                  30
Ile Leu Ala Thr Val Ser Val Leu Ala Val Lys Gly Ser Leu Ala Pro
            35                  40                  45
Ile Ser Gly Thr Val Gln Ser Ala His Leu Ile Ile Arg Phe Asp Glu
        50                  55                  60
Asn Gly Val Leu Leu Asn Asn Ser Phe Leu Asp Pro Glu Tyr Trp Asn
65                  70                  75                  80
Phe Arg Asn Gly Asp Leu Thr Glu Gly Thr Ala Tyr Thr Asn Ala Val
                85                  90                  95
Gly Phe Met Pro Asn Leu Ser Ala Tyr Pro Lys Ser His Gly Lys Thr
            100                 105                 110
Ala Lys Ser Asn Ile Val Ser Gln Val Tyr Leu Asn Gly Asp Lys Thr
        115                 120                 125
Lys Pro Val Thr Leu Thr Ile Thr Leu Asn Gly Thr Gln Glu Thr Gly
    130                 135                 140
Asp Thr Thr Pro Ser Ala Tyr Ser Met Ser Phe Ser Trp Asp Trp Ser
145                 150                 155                 160
Gly His Asn Tyr Ile Asn Glu Ile Phe Ala Thr Ser Ser Tyr Thr Phe
                165                 170                 175
Ser Tyr Ile Ala Gln Glu
            180

<210> SEQ ID NO 41
<211> LENGTH: 338
<212> TYPE: PRT
<213> ORGANISM: human adenovirus protein

<400> SEQUENCE: 41

Ala Pro Lys Gly Ala Pro Asn Pro Cys Glu Trp Asp Glu Ala Ala Thr
1               5                   10                  15
Ala Leu Glu Ile Asn Leu Glu Glu Asp Asp Asn Glu Asp
                20                  25                  30
Val Asp Glu Gln Ala Glu Gln Gln Lys Thr His Val Phe Gly Gln Ala
            35                  40                  45
Pro Tyr Ser Gly Ile Asn Ile Thr Lys Glu Gly Ile Gln Ile Gly Val
        50                  55                  60
Glu Gly Gln Thr Pro Lys Tyr Ala Asp Lys Thr Phe Gln Pro Glu Pro
65                  70                  75                  80
```

-continued

```
Gln Ile Gly Glu Ser Gln Trp Tyr Glu Thr Glu Ile Asn His Ala Ala
             85                  90                  95

Gly Arg Val Leu Lys Lys Thr Thr Pro Met Lys Pro Cys Tyr Gly Ser
            100                 105                 110

Tyr Ala Lys Pro Thr Asn Glu Asn Gly Gly Gln Gly Ile Leu Val Lys
            115                 120                 125

Gln Gln Asn Gly Lys Leu Glu Ser Gln Val Glu Met Gln Phe Phe Ser
        130                 135                 140

Thr Thr Glu Ala Thr Ala Gly Asn Gly Asp Asn Leu Thr Pro Lys Val
145                 150                 155                 160

Val Leu Tyr Ser Glu Asp Val Asp Ile Glu Thr Pro Asp Thr His Ile
                165                 170                 175

Ser Tyr Met Pro Thr Ile Lys Glu Gly Asn Ser Arg Glu Leu Met Gly
                180                 185                 190

Gln Gln Ser Met Pro Asn Arg Pro Asn Tyr Ile Ala Phe Arg Asp Asn
            195                 200                 205

Phe Ile Gly Leu Met Tyr Tyr Asn Ser Thr Gly Asn Met Gly Val Leu
    210                 215                 220

Ala Gly Gln Ala Ser Gln Leu Asn Ala Val Val Asp Leu Gln Asp Arg
225                 230                 235                 240

Asn Thr Glu Leu Ser Tyr Gln Leu Leu Leu Asp Ser Ile Gly Asp Arg
                245                 250                 255

Thr Arg Tyr Phe Ser Met Trp Asn Gln Ala Val Asp Ser Tyr Asp Pro
            260                 265                 270

Asp Val Arg Ile Ile Glu Asn His Gly Thr Glu Asp Glu Leu Pro Asn
        275                 280                 285

Tyr Cys Phe Pro Leu Gly Gly Val Ile Asn Thr Glu Thr Leu Thr Lys
        290                 295                 300

Val Lys Pro Lys Thr Gly Gln Glu Asn Gly Trp Glu Lys Asp Ala Thr
305                 310                 315                 320

Glu Phe Ser Asp Lys Asn Glu Ile Arg Val Gly Asn Asn Phe Ala Met
                325                 330                 335

Glu Ile
```